United States Patent [19]

Fodor et al.

[11] Patent Number: 5,424,186
[45] Date of Patent: Jun. 13, 1995

[54] VERY LARGE SCALE IMMOBILIZED POLYMER SYNTHESIS

[75] Inventors: Stephen P. A. Fodor, Palo Alto; Lubert Stryer, Stanford, both of Calif.; Michael C. Pirrung, Durham, N.C.; J. Leighton Read, Palo Alto, Calif.

[73] Assignee: Affymax Technologies N.V., Netherlands Antilles

[21] Appl. No.: 805,727

[22] Filed: Dec. 6, 1991

Related U.S. Application Data

[63] Continuation-in-part of Ser. No. 492,462, Mar. 7, 1990, Pat. No. 5,143,854, and a continuation-in-part of Ser. No. 624,120, Dec. 6, 1990, which is a continuation-in-part of Ser. No. 49,246, Dec. 6, 1990, and Ser. No. 362,901, Jun. 7, 1989, abandoned, said Ser. No. 492,462, is a continuation-in-part of Ser. No. 362,901, Jun. 7, 1989.

[51] Int. Cl.$^6$ .......................... C12Q 1/68; C07H 1/00
[52] U.S. Cl. ............................. 435/6; 436/518; 436/527; 436/528; 436/809; 436/25.3; 436/25.31; 436/25.32
[58] Field of Search .................. 530/333–337; 436/518, 527–532, 809; 435/6; 357/4; 427/2; 536/25.3, 25.31

[56] References Cited

U.S. PATENT DOCUMENTS

| | | | |
|---|---|---|---|
| 4,562,157 | 12/1985 | Lowe et al. | 435/291 |
| 4,631,211 | 12/1986 | Houghten | 428/35 |
| 4,713,326 | 12/1987 | Dattagupta et al. | 435/6 |
| 4,833,092 | 5/1989 | Geysen | 436/518 X |
| 5,079,600 | 1/1992 | Schnur et al. | 357/4 |
| 5,112,962 | 5/1992 | Letsinger et al. | 536/27 |
| 5,143,854 | 9/1992 | Pirrung et al. | 436/518 |
| 5,235,028 | 8/1993 | Barany et al. | 528/335 |

OTHER PUBLICATIONS

Ajayaghosh et al, Tetrahedron, vol. 44, No. 21, pp. 6661–6666, 1988.
Hellberg et al, Int. J. Peptide Protein Res., vol. 37, pp. 414–424, 1991.
Haridasan et al., "Peptide Synthesis Using Photolytically Cleavable 2-Nitrobenzyloxycarbonyl Protecting Group," *Proc. Indian Natl. Sci. Acad., Part A* (1987) 53:717–728.
Sze/McGillis, *VLSI Technology*, Chapter 7, pp. 267–301, McGraw-Hill, 1983.
Geysen et al., "Strategies for epitope analysis using peptide synthesis," *J. Immunol. Meth.* (1987) 102:259–274.
Furka et al., "More Peptides by Less Labor," Abstract No. 288 from *Xth International Symposium on Medicinal Chemistry*, Budapest, Hungary, Aug. 15–19, 1988.
Fodor et al., "Light-Directed, Spatially Addressable Parallel Chemical Synthesis," *Science* (1991) 251:767–773.
Kleinfeld et al., "Controlled Outgrowth of Dissociated Neurons on Patterned Substrates," *J. of Neuroscience*, 8(11):4098–4120, Nov. 1988.

*Primary Examiner*—Esther M. Kepplinger
*Assistant Examiner*—Lora M. Green
*Attorney, Agent, or Firm*—Kevin R. Kaster; Vern Norviel

[57] ABSTRACT

A method for synthesizing oligonucleotides on a solid substrate. The method provides for the irradiation of a first predefined region of the substrate without irradiation of a first predefined region of the substrate. The irradiation of a second predefined region of the substrate. The irradiation step removes a protecting group therefrom. The substrate is contacted with a first nucleotide to couple the nucleotide to the substrate in the first predefined region. By repeating these steps, an array of diverse oligonucleotides is formed on the substrate.

17 Claims, 42 Drawing Sheets

|  | P | A | S | G |  |
|---|---|---|---|---|---|
| L | LPGFL | LAGFL | LSGFL | LGGFL |  |
| F | FPGFL | FAGFL | FSGFL | FGGFL | L SET |
| W | WPGFL | WAGFL | WSGFL | WGGFL |  |
| Y | YPGFL | YAGFL | YSGFL | YGGFL |  |

FIG. 15A.

|  | p | a | s | G |  |
|---|---|---|---|---|---|
| Y | YpGFL | YaGFL | YsGFL | YGGFL |  |
| f | fpGFL | faGFL | fsGFL | fGGFL | D SET |
| w | wpGFL | waGFL | wsGFL | wGGFL |  |
| y | ypGFL | yaGFL | ysGFL | yGGFL |  |

FIG. 15B.

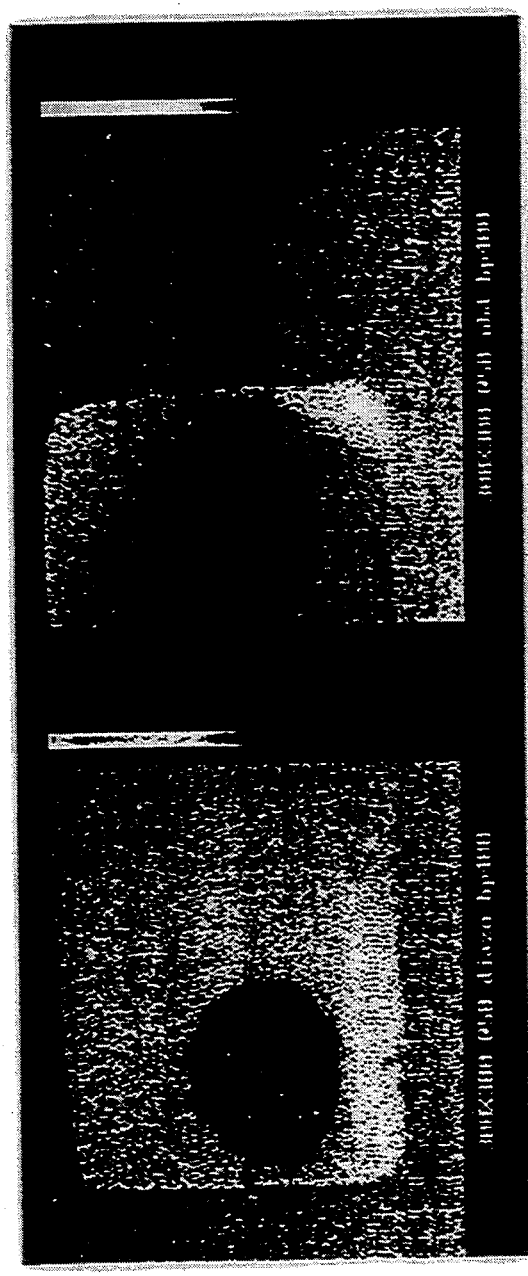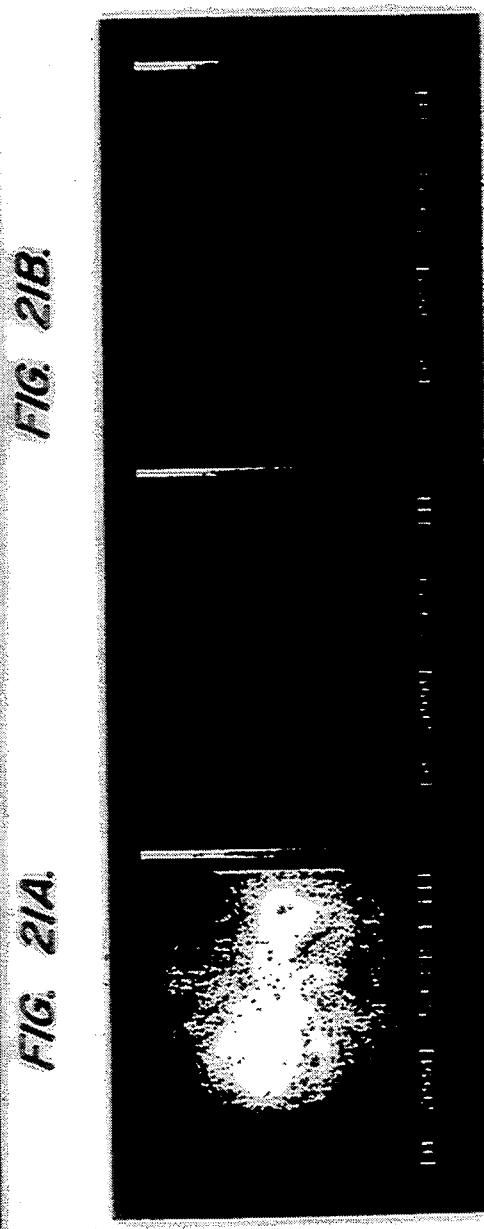
FIG. 21A. FIG. 21B.
FIG. 39A. FIG. 39B. FIG. 39C.

FIG. 29.

| STEP | AREA PHOTOLYZED | MASK | COUPLE |
|---|---|---|---|
| 1 | 100% | ▨ | T |
| 2 | 100% | · | V |
| 3 | 100% | · | V |
| 4 | 100% | · | K |
| 5 | 50% | □▨ | F |
| 6 TO 25 | Y20 | 20 STEPS { □ (NOT OVERLAPPING, ←W) □ □ } | G,A,R,K,C,M,S D,E,N,Q,F,H W,Y,L,P,V,I,T |
| 26 | 50% | ▨□ | Q |
| 27 | 100% | ▨ | R |

WILL GENERATE AN ARRAY OF 4 CLASSES OF PEPTIDES:

(1) RXKVVT
(2) RQXKVVT
(3) RQXFKVVT
(4) RXFKVVT

WHERE X REPRESENTS SUBSTITUTION OF ALL 20 L-AMINO ACIDS

FIG. 31.

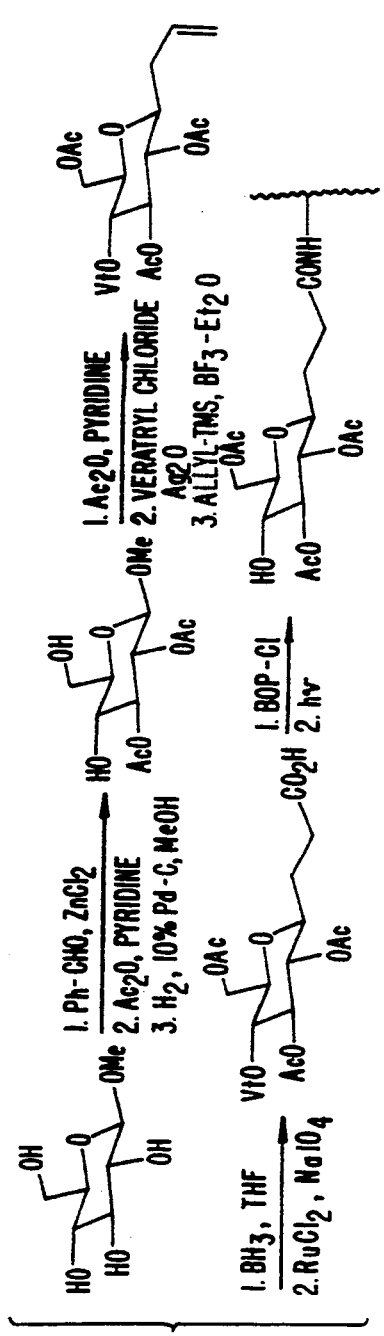
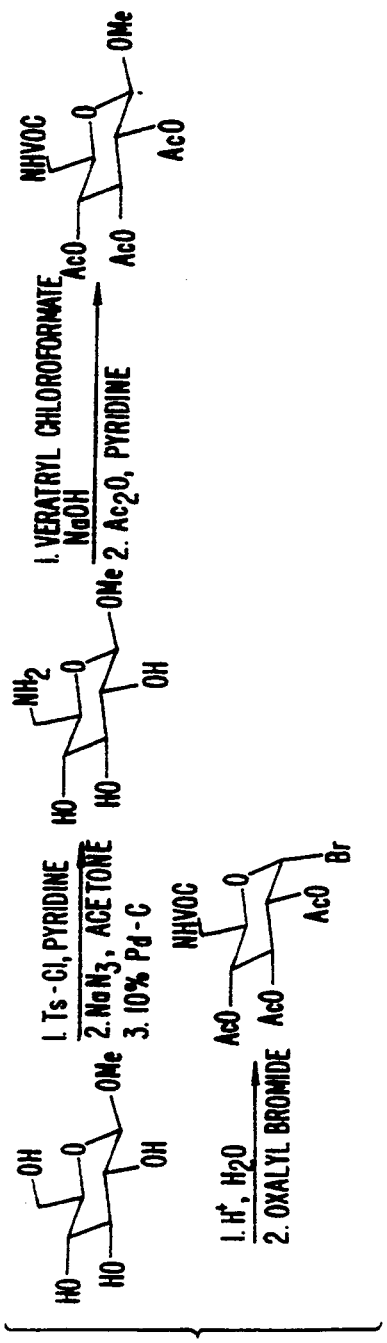
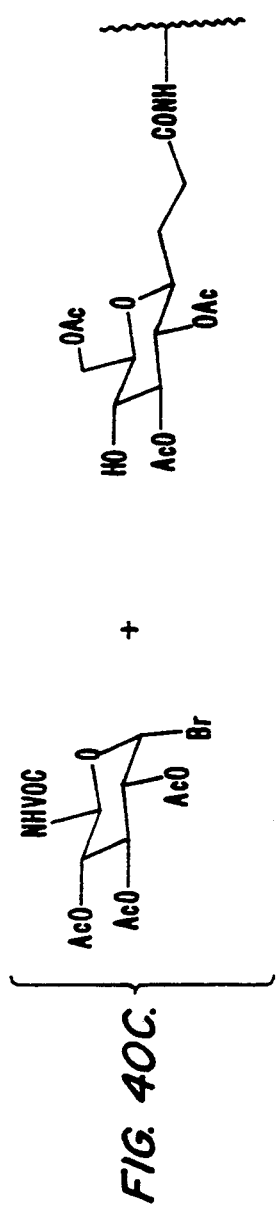
FIG. 40A.
FIG. 40B.
FIG. 40C.

+

WHERE R = AMINO ACID SIDE CHAIN OR OTHER DERIVATIVES
R' = ALKYL
P = PHOTO LABILE PROTECTING GROUP

HCl OR AcOH
IN DMF

─(AA)n  SLIDE

NaBH$_4$ OR NaCNBH$_3$

R" = H OR METHYL

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Tyr  Gly  Gly  Phe  Leu
    1                        5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Pro  Gly  Gly  Phe  Leu
    1                        5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Tyr  Pro  Gly  Gly  Phe  Leu
    1                            5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Tyr  Gly  Ala  Phe  Leu  Ser
1                    5

( 2 ) INFORMATION FOR SEQ ID NO:5:

( i ) SEQUENCE CHARACTERISTICS:
            ( A ) LENGTH: 5 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:5:

Tyr  Gly  Ala  Phe  Ser
1                    5

( 2 ) INFORMATION FOR SEQ ID NO:6:

( i ) SEQUENCE CHARACTERISTICS:
            ( A ) LENGTH: 5 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:6:

Tyr  Gly  Ala  Phe  Leu
1                    5

( 2 ) INFORMATION FOR SEQ ID NO:7:

( i ) SEQUENCE CHARACTERISTICS:
            ( A ) LENGTH: 6 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:7:

Tyr  Gly  Gly  Phe  Leu  Ser
1                    5

( 2 ) INFORMATION FOR SEQ ID NO:8:

( i ) SEQUENCE CHARACTERISTICS:
            ( A ) LENGTH: 4 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:8:

Tyr  Gly  Ala  Phe
1

( 2 ) INFORMATION FOR SEQ ID NO:9:

( i ) SEQUENCE CHARACTERISTICS:

( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:9:

Tyr Gly Ala Leu Ser
1                 5

( 2 ) INFORMATION FOR SEQ ID NO:10:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:10:

Tyr Gly Gly Phe Ser
1                 5

( 2 ) INFORMATION FOR SEQ ID NO:11:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:11:

Tyr Gly Ala Leu
1

( 2 ) INFORMATION FOR SEQ ID NO:12:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

Tyr Gly Ala Phe Leu Phe
1                 5

( 2 ) INFORMATION FOR SEQ ID NO:13:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:13:

Tyr Gly Ala Phe Phe
1                 5

( 2 ) INFORMATION FOR SEQ ID NO:14:

( i ) SEQUENCE CHARACTERISTICS:
( A ) LENGTH: 5 amino acids
( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:14:

Tyr Gly Gly Leu Ser
1               5

( 2 ) INFORMATION FOR SEQ ID NO:15:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:15:

Gly Gly Phe Leu
1

( 2 ) INFORMATION FOR SEQ ID NO:16:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:16:

Tyr Gly Ala Phe Ser Phe
1               5

( 2 ) INFORMATION FOR SEQ ID NO:17:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:17:

Tyr Gly Ala Phe Leu Ser Phe
1               5

( 2 ) INFORMATION FOR SEQ ID NO:18:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:18:

Tyr Gly Ala Phe Met Gln
1               5

( 2 ) INFORMATION FOR SEQ ID NO:19:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear (ii) MOLECULE TYPE: peptide (xi) SEQUENCE DESCRIPTION: SEQ ID NO:19:

Tyr Gly Ala Phe Met
1               5

(2) INFORMATION FOR SEQ ID NO:20:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Tyr Gly Ala Phe Gln
1               5

(2) INFORMATION FOR SEQ ID NO:21:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Tyr Gly Gly Phe Met
1               5

(2) INFORMATION FOR SEQ ID NO:22:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Tyr Ala Gly Phe Leu
1               5

(2) INFORMATION FOR SEQ ID NO:23:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Tyr Ser Gly Phe Leu
1               5

(2) INFORMATION FOR SEQ ID NO:24:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:24:

Tyr Pro Gly Phe Leu
1               5

( 2 ) INFORMATION FOR SEQ ID NO:25:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:25:

Leu Gly Gly Phe Leu
1               5

( 2 ) INFORMATION FOR SEQ ID NO:26:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:26:

Phe Gly Gly Phe Leu
1               5

( 2 ) INFORMATION FOR SEQ ID NO:27:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:27:

Leu Ala Gly Phe Leu
1               5

( 2 ) INFORMATION FOR SEQ ID NO:28:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:28:

Phe Ala Gly Phe Leu
1               5

( 2 ) INFORMATION FOR SEQ ID NO:29:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:29:

Trp Gly Gly Phe Leu
1               5

( 2 ) INFORMATION FOR SEQ ID NO:30:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

Tyr Gly Ala Gly Phe
1               5

( 2 ) INFORMATION FOR SEQ ID NO:31:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

Arg Gln Phe Lys Val Val Thr
1               5

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

Arg Xaa Lys Val Val Thr
1               5

( 2 ) INFORMATION FOR SEQ ID NO:33:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

Arg Gln Xaa Lys Val Val Thr
1               5

( 2 ) INFORMATION FOR SEQ ID NO:34:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:34:

Arg Gln Xaa Phe Lys Val Val Thr (2) INFORMATION FOR SEQ ID NO:35:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:35:

Arg Xaa Phe Lys Val Val Thr
   1               5

(2) INFORMATION FOR SEQ ID NO:36:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:36:

Lys Val Val Thr
   1

VERY LARGE SCALE IMMOBILIZED POLYMER SYNTHESIS

CROSS-REFERENCE TO RELATED APPLICATIONS

This application is a continuation-in-part of U.S. appliction Ser. No. 492,462, filed Mar. 7, 1990 now U.S. Pat. No. 5,143,854 (which is a continuation-in-part of U.S. application Ser. No. 362,901, filed Jun. 7, 1989, now abandoned) and U.S. application Ser. NO. 624,120, filed Dec. 6, 1990 (which is a continuation-in-part of U.S. application Ser. Nos. 07/492,462 and 07/362,901), which applications are incorporated herein by reference for all purposes.

This application is also related to the following U.S. applications, all of which are incorporated herein by reference for all purposes: U.S. Ser. Nos. 626,730 and 624,114, now abandoned, both filed on Dec. 6, 1990; U.S. Ser. Nos. 796,243, 796,947, now U.S. Pat. No. 5,324,463, and 796,727, now U.S. Pat. No. 5,242,974 all filed on Nov. 22, 1991; and PCT application No. WO 90/15070, which was published Dec. 13, 1990.

COPYRIGHT NOTICE

The file of this patent contains at least one drawing executed in color. Copies of this patent with color drawing(s) will be provided by the Patent and Trademark Office upon request and payment of the necessary fee.

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

MICROFICHE APPENDIX

This specificaiton includes microfiche appendices 1, 2 and 3, having 5 sheets with 348 frames.

BACKGROUND OF THE INVENTION

The present invention relates to the field of polymer synthesis. More specifically, the invention provides a reactor system, a masking strategy, photoremovable protecting groups, data collection and processing techniques, and applications for light directed synthesis of diverse polymer sequences on substrates.

Prior methods of preparing large numbers of different polymers have been painstakingly slow when used at a scale sufficient to permit effective rational or random screening. For example, the "Merrifield" method (J. Am. Chem. Soc. (1963) 85:2149–2154, which is incorporated herein by reference for all purposes) has been used to synthesize peptides on a solid support. In the Merrifield method, an amino acid is covalently bonded to a support made of an insoluble polymer. Another amino acid with an alpha protecting group is reacted with the covalently bonded amino acid to form a dipeptide. After washing, the protecting group is removed and a third amino acid with an alpha protecting group is added to the dipeptide. This process is continued until a peptide of a desired length and sequence is obtained. Using the Merrifield method, it is not economically practical to synthesize more than a handful of peptide sequences in a day.

To synthesize larger numbers of polymer sequences, it has also been proposed to use a series of reaction vessels for polymer synthesis. For example, a tubular reactor system may be used to synthesize a linear polymer on a solid phase support by automated sequential addition of reagents. This method still does not enable the synthesis of a sufficiently large number of polymer sequences for effective economical screening, i.e., for purposes of drug discovery.

Methods of preparing a plurality of polymer sequences are also known in which a foraminous container encloses a known quantity of reactive particles, the particles being larger in size than foramina of the container. The containers may be selectively reacted with desired materials to synthesize desired sequences of product molecules. As with other methods known in the art, this method cannot practically be used to synthesize a sufficient variety of polypeptides for effective screening.

Other techniques have also been described. These methods include the synthesis of peptides on 96 plastic pins which fit the format of standard microtiter plates. Unfortunately, while these techniques have been somewhat useful, substantial problems remain. For example, these methods continue to be limited in the diversity of sequences which can be economically synthesized and screened.

From the above, it is seen that an improved method and apparatus for synthesizing a variety of chemical sequences at known locations is desired.

SUMMARY OF THE INVENTION

Methods, apparatus, and compositions for synthesis and use of diverse polymer sequences on a substrate are disclosed, as well as applications thereof.

In one preferred embodiment, linker molecules are provided on a substrate. A terminal end of the linker molecules is provided with a reactive functional group protected with a photoremovable protective group. Using lithographic methods, the photoremovable protecting group is exposed to light and removed from the linker molecules in the first selected regions. The substrate is then washed or otherwise contacted with a first monomer that reacts with exposed functional groups on the linker molecules. In a preferred embodiment, the monomer is an amino acid containing a photoremovable protecting group at its amino or carboxy terminus and the linker molecule terminates in an amino or carboxy acid group bearing a photoremovable protective group.

A second set of selected regions is, thereafter, exposed to light and the photoremovable protecting group on the linker molecule/protected amino acid is removed at the second set of regions. The substrate is then contacted with a second monomer containing a photoremovable protecting group for reaction with exposed functional groups. This process is repeated to selectively apply monomers until polymers of a desired length and desired chemical sequence are obtained. Photolabile groups are then optionally removed and the sequence is, thereafter, optionally capped. Side chain protective groups, if present, are also removed.

By using the lithographic techniques disclosed herein, it is possible to direct light to relatively small and precisely known locations on the substrate. It is, therefore, possible to synthesize polymers of a known chemical sequence at known locations on the substrate. The general version of this technique is termed Very Large Scale Immobilized Polymer Synthesis (VLSIPS TM).

The resulting substrate will have a variety of uses including, for example, screening large numbers of polymers for biological activity. To screen for biological activity, the substrate is exposed to one or more receptors such as an antibody whole cells, receptors on vesicles, lipids, or any one of a variety of other receptors. The receptors are preferably labeled with, for example, a fluorescent marker, radioactive marker, or a labeled antibody reactive with the receptor. The location of the marker on the substrate is detected with, for example, photon detection or autoradiographic techniques. Through knowledge of the sequence of the material at the location where binding is detected, it is possible to quickly determine which sequence binds with the receptor and, therefore, the technique can be used to screen large numbers of peptides. Other possible applications of the inventions herein include diagnostics in which various antibodies for particular receptors would be placed on a substrate and, for example, blood sera would be screened for immune deficiencies. Still further applications include, for example, selective "doping" of organic materials in semiconductor devices, i.e., the introduction of selected impurities into the device and the like.

According to one aspect of the invention, an improved reactor system for synthesis of diverse polymer sequences on a substrate is provided. According to this embodiment the invention provides for a reactor for contacting reaction fluids to a substrate; a system for delivering selected reaction fluids to the reactor; a translation stage for moving a mask or substrate from at least a first relative location relative to a second relative location; a light for illuminating the substrate through a mask at selected times; and an appropriately programmed digital computer for selectively directing a flow of fluids from the reactor system, selectively activating the translation stage, and selectively illuminating the substrate so as to form a plurality of diverse polymer sequences on the substrate at predetermined locations.

The invention also provides a technique for selection of linker molecules using the VLSIPS TM synthesis technique. According to this aspect of the invention, the invention provides a method of screening a plurality of linker polymers for use in binding affinity studies. The invention includes the steps of forming a plurality of linker polymers on a substrate in selected regions, the linker polymers are formed by the steps of recursively: (1) on a surface of a substrate, irradiating a portion of the selected regions to remove a protecting group, and contacting the surface with a monomer; (2) contacting the plurality of linker polymers with a ligand; and (3) contacting the ligand with a labeled receptor.

According to another aspect of the invention, improved photoremovable protecting groups are provided. According to this aspect of the invention a compound having the formula:

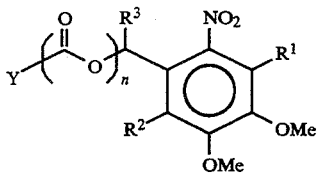

wherein n=0 or 1; Y is selected from the group consisting of an oxygen of the carboxyl group of a natural or unnatural amino acid, an amino group of a natural or unnatural amino acid, or the C-5' oxygen group of a natural or unnatural deoxyribonucleic or ribonucleic acid; $R^1$ and $R^2$ independently are a hydrogen atom, a lower alkyl, aryl, benzyl, halogen, hydroxyl, alkoxyl, thiol, thioether, amino, nitro, carboxyl, formate, formamido, sulfido, or phosphido group; and $R^3$ is a alkoxy, alkyl, aryl, hydrogen, or alkenyl group is provided.

The invention also provides improved masking techniques for VLSIPS. According to one aspect of the masking technique, the invention provides an ordered method for forming a plurality of polymer sequences by sequential addition of reagents comprising the step of serially protecting and deprotecting portions of the plurality of polymer sequences for addition of other portions of the polymer sequences using a combinatorial synthesis strategy.

Improved data collection equipment and techniques are also provided. According to one embodiment, the instrumentation provides a system for determining affinity of a receptor to a ligand comprising: means for applying light to a surface of a substrate, the substrate comprising a plurality of ligands at predetermined locations, the means for applying light providing simultaneous illumination at a plurality of the predetermined locations; and an array of detectors for detecting fluorescence at the plurality of predetermined locations. The invention further provides for improved data analysis techniques including the steps of exposing fluorescently labelled receptors to a substrate, the substrate comprising a plurality of ligands in regions at known locations; at a plurality of data collection points within each of the regions, determining an amount of fluorescence from the data collection points; removing the data collection points deviating from a predetermined statistical distribution; and determining a relative binding affinity of the receptor from remaining data collection points.

Protected amino acid N-carboxy anhydrides for use in polymer synthesis are also disclosed. According to this aspect of the invention, a compound having the following formula is provided:

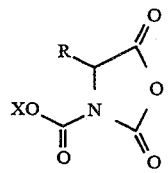

where R is a side chain of a natural or unnatural amino acid and X is a photoremovable protecting group.

A further understanding of the nature and advantages of the inventions herein may be realized by reference to the remaining portions of the specification and the attached drawings.

BRIEF DESCRIPTION OF THE DRAWINGS

FIGS. 15A and 15B illustrate the mapping of 16 sequences synthesized on two different glass slides;

FIGS. 21A and 21B are fluorescence plots generated with fluorescence energy-transfer substrate assays;

FIG. 29 is a coordinate map for the ten-step binary synthesis;

FIG. 31 illustrates a strategy for producing an array of peptides related to the dynorphin B sequence;

FIG. 39A-39C are fluorescence plots demonstrating hybridization, dehybridization and rehybridization between immobilized poly A and poly T;

FIGS. 40A-40E illustrate a synthesis strategy for forming polysaccharides in accordance with the present invention.

DESCRIPTION OF THE PREFERRED EMBODIMENTS

CONTENTS

Figure 1:
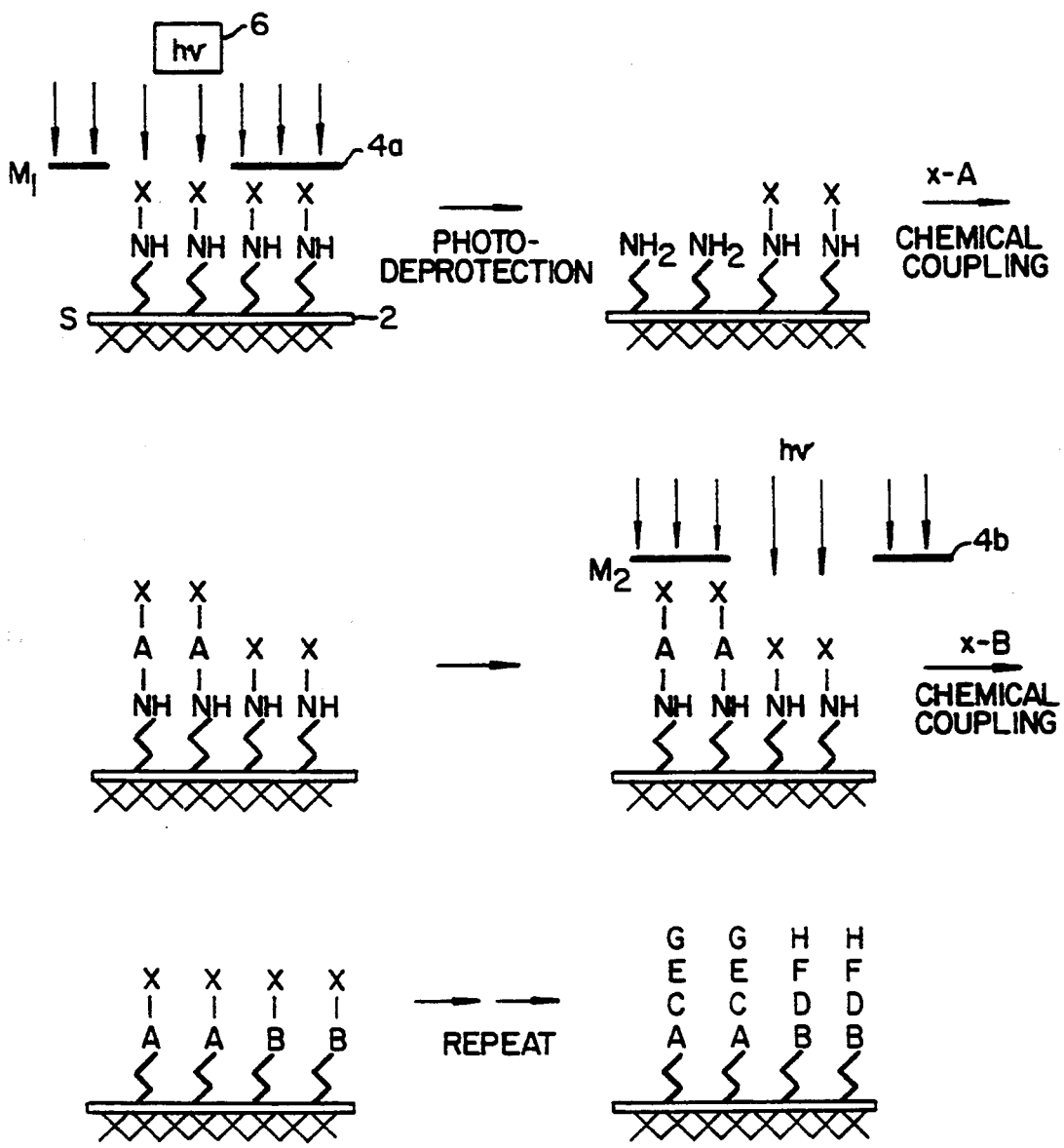
FIGS. 1 to 7 illustrate masking, irradiation, and coupling of monomers.

I. Definitions
II. General
   A. Deprotection and Addition
      1. Example - Polymer Synthesis
      2. Example
      3. Example - Slide Preparation
      4. Example - Synthesis of a Dimer of an Aminopropyl Group and a Fluorescent Group
      5. Example - Removal of NVOC and Attachment of a Marker
      6. Example - Use of a Mask in Removal of NVOC
      7. Example
      8. Example
   B. Antibody recognition
      1. Example - Attachment of YGGFL and Subsequent Exposure to Herz Antibody and Goat Antimouse
      2. Example
      3. Example - Monomer-by-Monomer Formation of YGGFL and Subsequent Exposure to Labeled Antibody
      4. Example - Monomer-by-Monomer Synthesis of YGGFL and YPGGFL
      5. Example - Synthesis of an Array of Sixteen Different Amino Acid Sequnces and Estimation of Relative Binding Affinity to Herz Antibody
      6. Example
      7. Example
   C. Fluorescence Energy-Transfer Substrate Assays
III. Synthesis
   A. Reactor System
   B. Binary Synthesis Strategy
      1. Example
      2. Example
      3. Example
      4. Example
      5. Example
      6. Example
      7. Example
      8. Example
      9. Example
      10. Example
   C. Linker Selection
   D. Protecting Groups
      1. Use of Photoremovable Protecting Groups During Solid-Phase Synthesis of Peptides
      2. Use of Photoremovable Protecting Groups During Solid-Phase Synthesis of Oligonucleotides
   E. Amino Acid N-Carboxy Anhydrides Protected with a Photoremovable Group
IV. Data Collection
   A. Data Collection System
   B. Data Analysis
   C. Alternative Embodiments
V. Other Representative Applications A. Oligonucleotide Synthesis
   1. Example
   2. Example
   3. Example
B. Oligosaccharide Synthesis
   1. Example
C. Caged Binding Member System
D. Fingerprinting for Quality Control
E. β-Amino Acid and D-Amino Acid Monomers
F. Reduced Amide Bonds
VI. Conclusion

I. Definitions

Certain terms used herein are intended to have the following general definitions:

1. Complementary: Refers to the topological compatibility or matching together of interacting surfaces of a ligand molecule and its receptor. Thus, the receptor and its ligand can be described as complementary, and furthermore, the contact surface characteristics are complementary to each other.

2. Epitope: The portion of an antigen molecule which is delineated by the area of interaction with the subclass of receptors known as antibodies.

3. Ligand: A ligand is a molecule that is recognized by a particular receptor. Examples of ligands that can be investigated by this invention include, but are not restricted to, agonists and antagonists for cell membrane receptors, toxins and venoms, viral epitopes, hormones (e.g., steroids, etc.), hormone receptors, opiates, peptides, enzymes, enzyme substrates, cofactors, drugs, lectins, sugars, oligonucleotides, nucleic acids, oligosaccharides, proteins, and monoclonal antibodies.

4. Monomer: A member of the set of small molecules which can be joined together to form a polymer. The set of monomers includes but is not restricted to, for example, the set of common L-amino acids, the set of D-amino acids, the set of natural or synthetic amino acids, the set of nucleotides and the set of pentoses and hexoses. As used herein, monomer refers to any member of a basis set for synthesis of a polymer. For example, dimers of the 20 naturally occurring L-amino acids form a basis set of 400 monomers for synthesis of polypeptides. Different basis sets of monomers may be used in any of the successive steps in the synthesis of a polymer. Furthermore, each of the sets may include protected members which are modified after synthesis.

5. Peptide: A polymer in which the monomers are alpha amino acids and which are joined together through amide bonds, alternatively referred to as a polypeptide. In the context of this specification it should be appreciated that the amino acids may, for example, the L-optical isomer or the D-optical isomer. Peptides are often two or more amino acid monomers long, and often 4 or more amino acids long, often 5 or more amino acids long, often 10 or more amino acids long, often 15 or more amino acids long, and often 20 or more amino acid monomers long, for example. Standard abbreviations for amino acids are used (e.g., P for proline). These abbreviations are included in Stryer, *Biochemistry*, Third Ed., 1988, which is incorporated herein by reference for all purposes.

6. Radiation: Energy which may be selectively applied including energy having a wavelength of between $10^{-14}$ and $10^4$ meters including, for example, electron beam radiation, gamma radiation, x-ray radiation, ultraviolet radiation, visible light, infrared radiation, microwave radiation, and radio waves. "Irradiation" refers to the application of radiation to a surface.

7. Receptor: A molecule that has an affinity for a given ligand. Receptors may be naturally-occurring or synthetic molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells, or other materials), drugs, polynucleotides, nucleic acids, peptides, cofactors, lectins, sugars, polysaccharides, cells, cellular membranes, and organelles. Receptors are sometimes referred to in the art as antiligands. As the term receptors is used herein, no difference in meaning is intended. A "Ligand Receptor Pair" is formed when two macromolecules have combined through molecular recognition to form a complex.

Other examples of receptors which can be investigated by this invention include but are not restricted to:

a) Microorganism receptors: Determination of ligands which bind to receptors, such as specific transport proteins or enzymes essential to survival of microorganisms, is useful for a new class of antibiotics. Of particular value would be antibiotics against opportunistic fungi, protozoa, and those bacteria resistant to the antibiotics in current use.

b) Enzymes: For instance, determining the binding site of enzymes such as the enzymes responsible for cleaving neurotransmitters provides useful information. Determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the development of vaccines of which the immunogen is based on one or more of such sequences or lead to the development of related diagnostic agents or compounds useful in therapeutic treatments such as for auto-immune diseases (e.g., by blocking the binding of the "self" antibodies). "Antibody" as used herein can also include antibody fragments, such as Fab fragments, which are composed of a light chain and the variable region of a heavy chain.

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, in which the functionality is capable of chemically modifying the bound reactant. Catalytic polypeptides are described in, for example, U.S. application Ser. No. 404,920 (U.S. Pat. No.

5,215,899), which is incorporated herein by reference for all purposes.

f) Hormone receptors: For instance, the receptors for insulin and growth hormone. Determination of the ligands which bind with high affinity to a receptor is useful in the development of, for example, an oral replacement of the daily injections which diabetics must take to relieve the symptoms of diabetes, and in the other case, a replacement for the scarce human growth hormone which can only be obtained from cadavers or by recombinant DNA technology. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

8. Substrate: A material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or the like. According to other embodiments, small beads may be provided on the surface which may be released upon completion of the synthesis.

9. Protecting group: A material which is chemically bound to a monomer unit and which may be removed upon selective exposure to an activator such as electromagnetic radiation and, especially ultraviolet and visible light. Examples of protecting groups with utility herein include those comprising nitropiperonyl, pyrenylmethoxy-carbonyl, nitroveratryl, nitrobenzyl, dimethyl dimethoxybenzyl, 5-bromo-7-nitroindolinyl, o-hydroxy-α-methyl cinnamoyl, and 2-oxymethylene anthraquinone.

10. Predefined Region: A predefined region is a localized area on a surface which is, was, or is intended to be activated for formation of a polymer. The predefined region may have any convenient shape, e.g., circular, rectangular, elliptical, wedgeshaped, etc. For the sake of brevity herein, "predefined regions" are sometimes referred to simply as "regions."

11. Substantially Pure: A polymer is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor. Preferably the region is sufficiently pure such that the predominant species in the predefined region is the desired sequence. According to preferred aspects of the invention, the polymer is 5% pure, more preferably more than 10% pure, preferably more than 20% pure, more preferably more than 80% pure, more preferably more than 90% pure, more preferably more than 95% pure, where purity for this purpose refers to the ratio of the number of ligand molecules formed in a predefined region having a desired sequence to the total number of molecules formed in the predefined region.

12. Activator: An energy source adapted to render a group active and which is directed from a source to a predefined location on a substrate. A primary illustration of an activator is light. Other examples of activators include ion beams, electric fields, magnetic fields, electron beams, x-ray, and the like.

13. Combinatorial Synthesis Strategy: An ordered strategy for parallel synthesis of diverse polymer sequences by sequential addition of reagents which may be represented by a reactant matrix, and a switch matrix, the product of which is a product matrix. A reactant matrix is a 1 column by m row matrix of the building blocks to be added. The switch matrix is all or a subset of the binary numbers, preferably ordered, between 1 and m arranged in columns. In preferred embodiments, a "binary strategy" is one in which at least two successive steps illuminate half of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A conbinatorial "masking" strategy is a synthesis which uses light or other deprotecting or activating agents to remove protecting groups from materials for addition of other materials such as amino acids. In some embodiments, selected columns of the switch matrix are arranged in order of increasing binary numbers in the columns of the switch matrix.

14. Linker: A molecule or group of molecules attached to a substrate and spacing a synthesized polymer from the substrate for exposure/binding to a receptor.

15. Abbreviations: The following abbreviations are intended to have the following meanings:

BOC: benzyloxycarbonyl.
BOP: benzotriazol-1-yloxytris-(dimethylamino). phosphonium hexafluorophosphate.
CCD: charge coupled device.
DCC: dicyclohexylcarbodiimide.
DCM: dichloromethane; methylene chloride.
DDZ: dimethoxydimethylbenzyloxy.
DIEA: N,N-diisopropylethylamine.
DMAP: 4-dimethylaminopyridine.
DMF: dimethyl formamide.
DMT: dimethoxytrityl.
FMOC: fluorenylmethyloxycarbonyl.
HBTU: 2-(1H-benzotriazol-1-yl) -1,1,3,3-tetramethyluronium hexafluorophosphate.
HOBT: 1-hydroxybenzotriazole hydrate.
NMP: N-methylpyrrolidone.
NV: nitroveratryl.
NVOC: 6-nitroveratryloxycarbonyl.
PG: protective group.
TFA: trifluoracetic acid.
THF: tetrahydrofuran.

II. General

The present invention provides synthetic strategies and devices for the creation of large scale chemical diversity. Solid-phase chemistry, photolabile protecting groups, and photolithography are brought together to achieve light-directed spatially-addressable parallel chemical synthesis in preferred embodiments.

The invention is described herein for purposes of illustration primarily with regard to the preparation of peptides and nucleotides, but could readily be applied in the preparation of other polymers. Such polymers include, for example, both linear and cyclic polymers of nucleic acids, polysaccharides, phospholipids, and peptides having either $\alpha$-, $\beta$-, or $\omega$-amino acids, heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure. It will be recognized further, that illustrations herein are primarily with reference to C- to N-terminal synthesis, but the invention could readily be applied to N- to C-terminal synthesis without departing from the scope of the invention. Methods for forming cyclic and reversed polarity peptides and other polymers are described in copending U.S. application Ser. No. 796,727 U.S. Pat. No. 5,242,974 filed on Nov. 22, 1991 and previously incorporated herein by reference.

The prepared substrate may, for example, be used in screening a variety of polymers as ligands for binding with a receptor, although it will be apparent that the invention could be used for the synthesis of a receptor for binding with a ligand. The substrate disclosed herein will have a wide variety of other uses. Merely by way of example, the invention herein can be used in determining peptide and nucleic acid sequences which bind to proteins, finding sequence-specific binding drugs, identifying epitopes recognized by antibodies, and evaluation of a variety of drugs for clinical and diagnostic applications, as well as combinations of the above.

The invention preferably provides for the use of a substrate "S" with a surface. Linker molecules "L" are optionally provided on a surface of the substrate. The purpose of the linker molecules, in some embodiments, is to facilitate receptor recognition of the synthesized polymers.

Optionally, the linker molecules may be chemically protected for storage purposes. A chemical storage protecting group such as t-BOC (t-butoxycarbonyl) may be used in some embodiments. Such chemical protective groups would be chemically removed upon exposure to, for example, acidic solution and would serve to protect the surface during storage and be removed prior to polymer preparation.

On the substrate or a distal end of the linker molecules, a functional group with a protecting group $P_0$ is provided. The protecting group $P_0$ may be removed upon exposure to radiation, electric fields, electric currents, or other activators to expose the functional group.

In a preferred embodiment, the radiation is ultraviolet (UV), infrared (IR), or visible light. As more fully described below, the protecting group may alternatively be an electrochemically-sensitive group which may be removed in the presence of an electric field. In still further alternative embodiments, ion beams, electron beams, or the like may be used for deprotection.

A. Deprotection and Addition

Concurrently or after exposure of a known region of the substrate to light, the surface is contacted with a first monomer unit $M_1$ which reacts with the functional group which has been exposed by the deprotection step. The first monomer includes a protecting group $P_1$. $P_1$ may or may not be the same as $P_0$.

Accordingly, after a first cycle, known first regions of the surface may comprise the sequence:

$$S\text{-}L\text{-}M_1\text{-}P_1$$

while remaining regions of the surface comprise the sequence:

$$S\text{-}L\text{-}P_0.$$

Thereafter, second regions of the surface (which may include the first region) are exposed to light and contacted with a second monomer $M_2$ (which may or may not be the same as $M_1$) having a protecting group $P_2$. $P_2$ may or may not be the same as $P_0$ and $P_1$. After this second cycle, different regions of the substrate may comprise one or more of the following sequences:

$$S\text{—}L\text{—}M_1\text{—}M_2\text{—}P_2$$
$$S\text{—}L\text{—}M_2\text{—}P_2$$
$$S\text{—}L\text{—}M_1\text{—}P_1 \text{ and/or}$$
$$S\text{—}L\text{—}P_0.$$

The above process is repeated until the substrate includes desired polymers of desired lengths. By controlling the locations of the substrate exposed to light and the reagents exposed to the substrate following exposure, the location of each sequence will be known.

Thereafter, the protective groups are removed from some or all of the substrate and the sequences are, optionally, capped with a capping unit C. The process results in a substrate having a surface with a plurality of polymers of the following general formula:

$$S\text{-}[L]\text{-}(M_i)\text{-}(M_j)\text{-}(M_k) \ldots (M_x)\text{-}[C]$$

where square brackets indicate optional groups, and $M_i \ldots M_x$ indicates any sequence of monomers. The number of monomers could cover a wide variety of values, but in a preferred embodiment they will range from 2 to 100.

In some embodiments a plurality of locations on the substrate polymers are to contain a common monomer subsequence. For example, it may be desired to synthesize a sequence $S\text{-}M_1\text{-}M_2\text{-}M_3$ at first locations and a sequence $S\text{-}M_4\text{-}M_2\text{-}M_3$ at second locations. The process would commence with irradiation of the first locations followed by contacting with $M_1$-P, resulting in the sequence $S\text{-}M_1\text{-}P$ at the first location. The second locations would then be irradiated and contacted with $M_4$-P, resulting in the sequence $S\text{-}M_4\text{-}P$ at the second locations. Thereafter both the first and second locations would be irradiated and contacted with the dimer $M_2\text{-}M_3$, resulting in the sequence $S\text{-}M_1\text{-}M_2\text{-}M_3$ at the first locations and $S\text{-}M_4\text{-}M_2\text{-}M_3$ at the second locations. Of course, common subsequences of any length could be utilized including those in a range of 2 or more monomers, 2 to 100 monomers, 2 to 20 monomers, and a most preferred range of 2 to 3 monomers.

According to other embodiments, a set of masks is used for the first monomer layer and, thereafter, varied light wavelengths are used for selective deprotection. For example, in the process discussed above, first regions are first exposed through a mask and reacted with a first monomer having a first protecting group $P_1$, which is removable upon exposure to a first wavelength of light (e.g., IR). Second regions are masked and reacted with a second monomer having a second protecive group $P_2$ which is removable upon exposure to a second wavelength of light (e.g. UV). Thereafter, masks become unnecessary in the synthesis because the entire substrate may be exposed alternatively to the first and second wavelengths of light in the deprotection cycle.

The polymers prepared on a substrate according to the above methods will have a variety of uses including, for example, screening for biological activity. In such screening activities, the substrate containing the sequences is exposed to an unlabeled or labeled receptor such as an antibody, receptor on a cell, phospholipid vesicle, or any one of a variety of other receptors. In one preferred embodiment the polymers are exposed to a first, unlabeled receptor of interest and, thereafter, exposed to a labeled receptor-specific recognition element, which is, for example, an antibody. This process will provide signal amplification in the detection stage.

The receptor molecules may bind with one or more polymers on the substrate. The presence of the labeled receptor and, therefore, the presence of a sequence which binds with the receptor is detected in a preferred embodiment through the use of autoradiography, detection of fluorescence with a charge-coupled device, fluorescence microscopy, or the like. The sequence of the polymer at the locations where the receptor binding is detected may be used to determine all or part of a sequence which is complementary to the receptor.

Use of the invention herein is illustrated primarily with reference to screening for biological activity. The invention will, however, find many other uses. For example, the invention may be used in information storage (e.g., on optical disks), production of molecular electronic devices, production of stationary phases in separation sciences, production of dyes and brightening agents, photography, and in immobilization of cells, proteins, lectins, nucleic acids, polysaccharides and the like in patterns on a surface via molecular recognition of specific polymer sequences. By synthesizing the same compound in adjacent, progressively differing concentrations, a gradient will be established to control chemotaxis or to develop diagnostic dipsticks which, for example, titrate an antibody against an increasing amount of antigen. By synthesizing several catalyst molecules in close proximity, more efficient multistep conversions may be achieved by "coordinate immobilization." Coordinate immobilization also may be used for electron transfer systems, as well as to provide both structural integrity and other desirable properties to materials such as lubrication, wetting, etc.

According to alternative embodiments, molecular biodistribution or pharmacokinetic properties may be examined. For example, to assess resistance to intestinal or serum proteases, polymers may be capped with a fluorescent tag and exposed to biological fluids of interest.

FIG. 1 is a flow chart illustrating the process of forming chemical compounds according to one embodiment of the invention. Synthesis occurs on a solid support 2. A pattern of illumination through a mask 4a using a light source 6 determines which regions of the support are activated for chemical coupling. In one preferred embodiment activation is accomplished by using light to remove photolabile protecting groups from selected areas of the substrate.

After deprotection, monomers indicated by "A" in FIG. 1, each bearing a photolabile protecting group (indicated by "X"), are exposed to the surface of the substrate and react with regions that were addressed by light in the preceding step. The substrate is then illuminated through a second mask 4b, which activates another region for reaction with a second protected monomer "B." The process is then repeated using desired masks and mask orientations in combination with selected monomers. The pattern of masks used in these illuminations and the sequence of reactants define the ultimate products and their locations, resulting in diverse sequences at predefined locations, as shown with the sequences ACEG and BDFH in the lower portion of FIG. 1. Preferred embodiments of the invention take advantage of combinatorial masking strategies to form a large number of compounds in a small number of chemical steps.

A high degree of miniaturization is possible because the density of compounds is determined largely with regard to spatial addressability of the activator, in one case the diffraction of light. Each compound is physically accessible and its position is precisely known. Hence, the array is spatially-addressable and its interactions with other molecules can be assessed.

In a particular embodiment shown in FIG. 1, the substrate contains amino groups that are blocked with a photolabile protecting group. Amino acid sequences are made accessible for coupling to a receptor by removal of the photoprotecting groups.

When a polymer sequence to be synthesized is, for example, a polypeptide, amino groups at the ends of linkers attached to a glass substrate are derivatized with, for example, nitroveratryloxycarbonyl (NVOC), a photoremovable protecting group. The linker molecules may be, for example, aryl acetylene, ethylene glycol oligomers containing from 2-10 monomers, diamines, diacids, amino acids, or combinations thereof. Photodeprotection is effected by illumination of the substrate through, for example, a mask wherein the pattern has transparent regions with dimensions of, for example, less than 1 cm$^2$, 10$^{-1}$ cm$^2$, 10$^{-2}$ cm$^2$, 10$^{-1}$ cm$^2$, 10$^{-4}$ cm$^2$, 10$^{-5}$ cm$^2$, 10$^{-6}$ cm$^2$, 10$^{-7}$ cm$^2$, 10$^{-8}$ cm$^2$, or 10$^{-10}$ cm$^2$. In a preferred embodiment, the regions are between about 10×10 μm and 500×500 μm. According to some embodiments, the masks are arranged to produce a checkerboard array of polymers, although any one of a variety of geometric configurations may be utilized.

1. Example - Polymer Synthesis

Figure 2:
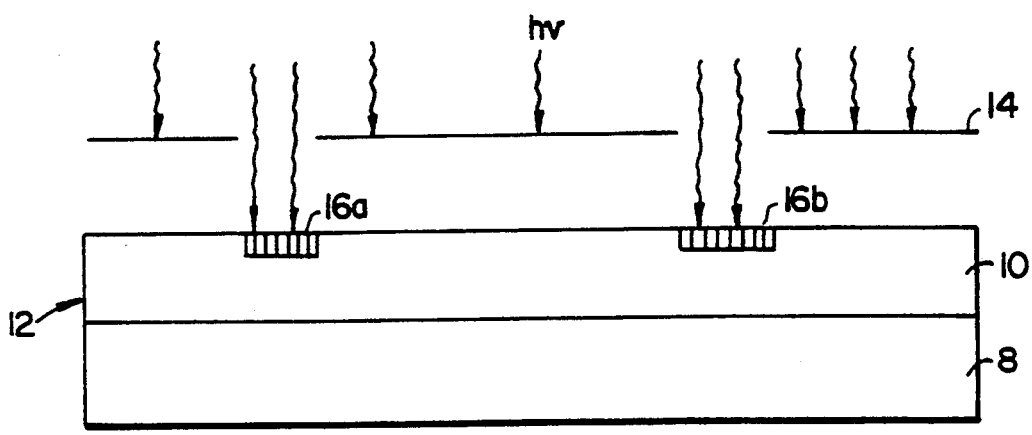

FIG. 2 illustrates one embodiment of the invention disclosed herein in which a substrate 8 is shown in cross-section. Essentially, any conceivable substrate may be employed in the invention. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is preferably flat but may take on a variety of alternative surface configurations. For example, the substrate may contain raised or depressed regions on which the synthesis takes place. The substrate and its surface preferably form a rigid support on which to carry out the reactions described herein. The substrate and its surface are also chosen to provide appropriate light-absorbing characteristics. For instance, the substrate may be a polymerized Langmuir Blodgett film, functionalized glass, Si, Ge, GaAs, GaP, SiO$_2$, SIN$_4$, modified silicon, any of the different crystal lattices made with silicon or gallium arsenide that are commercially available and used in semiconductor manufacturing, or any one of a wide variety of gels or polymers such as (poly)tetrafluoroethylene, (poly)vinylidenedifluoride, polystyrene, polycarbonate, or combinations thereof. Other substrate materials will be readily apparent to those of skill in the art upon review of this disclosure. In a preferred embodiment the substrate is flat-glass or single-crystal silicon with surface relief features of less than 10 Å.

According to some embodiments, the surface of the substrate is etched using well known techniques to provide for desired surface features. For example, by way of the formation of trenches, v-grooves, mesa structures, or the like, the synthesis regions may be more closely placed within the focus point of impinging light, be provided with reflective "mirror" structures for maximization of light collection from fluorescent sources, or the like.

Surfaces on the solid substrate will usually, though not always, be composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In some embodiments the surface may provide for the use of caged binding members which are attached firmly to the surface of the substrate. Preferably, the surface will contain reactive groups, which could be carboxyl, amino, hydroxyl, or the like. Most preferably, the surface will be optically transparent and will have surface Si-OH functionalities, such as are found on silica surfaces.

The surface 10 of the substrate is preferably provided with a layer of linker molecules 12, although it will be understood that the linker molecules are not required elements of the invention. The linker molecules are preferably of sufficient length to permit polymers in a completed substrate to interact freely with molecules exposed to the substrate. The linker molecules should be 6-50 atoms long to provide sufficient exposure. The linker molecules may be, for example, aryl acetylene, ethylene glycol oligomers containing 2-10 monomer units, diamines, diacids, amino acids, or combinations thereof. Other linker molecules may be used in light of this disclsoure.

According to alternative embodiments, the linker molecules are selected based upon their hydrophilic/-hydrophobic properties to improve presentation of synthesized polymers to certain receptors. For example-, in the case of a hydrophilic receptor, hydrophilic linker molecules will be preferred so as to permit the receptor to more closely approach the synthesized polymer.

According to another alternative embodiment, linker molecules are also provided with a photocleavable group at an intermediate position. The photocleavable group is preferably cleavable at a wavelength different from the protective group. This enables removal of the various polymers following completion of the synthesis by way of exposure to the different wavelengths of light. One can also modify the linker molecule with a photocleavable group, which, when removed, will induce a conformational change in the polymer attached to the linker.

The linker molecules can be attached to the substrate via carbon-carbon bonds using, for example, (poly)trifluorochloroethylene surfaces, or preferably, by siloxane bonds (using, for example, glass or silicon oxide surfaces). Siloxane bonds with the surface of the substrate may be formed in one embodiment via reactions of linker molecules bearing trichlorosilyl groups. The linker molecules may optionally be attached in an ordered array, i.e., as parts of the head groups in a polymerized Langmuir Blodgett film. In alternative embodiments, the linker molecules are adsorbed to the surface of the substrate.

The linker molecules and monomers used herein are provided with a functional group to which is bound a protective group. Preferably, the protecting group is on the distal or terminal end of the linker molecule opposite the substrate. The protecting group may be either a negative protecting group (i.e., the protecting group renders the linker molecules less reactive with a monomer upon exposure) or a positive protecting group (i.e., the protecting group renders the linker molecules more reactive with a monomer upon exposure). In the case of negative protective groups an additional step of reactivation will be required. In some embodiments, this will be done by heating. Those of skill in the art will also note that more than one functional group can be employed on either the linker or the monomer, i.e., to facilitate the synthesis of branched or "dendritic" structures.

The protecting group on the linker molecules may be selected from a wide variety of positive light-reactive groups preferably including nitro aromatic compounds such as o-nitrobenzyl derivatives or benzylsulfonyl. In a preferred embodiment, 6-nitroveratryloxycarbonyl (NVOC), 2-nitrobenzyloxycarbonyl (NBOC) or α,α-dimethyl-dimethoxybenzyloxycarbonyl (DDZ) is used. In one embodiment, a nitro aromatic compound containing a benzylic hydrogen ortho to the nitro group is used, i.e., a chemical of the form:

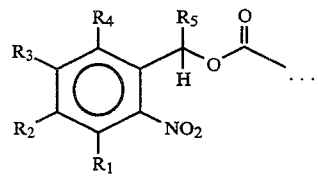

where $R_1$ is alkoxy, alkyl, halo, aryl, alkenyl, or hydrogen; $R_2$ is alkoxy, alkyl, halo, aryl, nitro, or hydrogen; $R_3$ is alkoxy, alkyl, halo, nitro, aryl, or hydrogen; $R_4$ is alkoxy, alkyl, hydrogen, aryl, halo, or nitro; and $R_5$ is alkyl, alkynyl, cyano, alkoxy, hydrogen, halo, aryl, or alkenyl. Other materials which may be used include o-hydroxy-α-methyl cinnamoyl derivatives.

In an alternative embodiment the positive reactive group is activated for reaction with reagents in solution. For example, a 5-bromo-7-nitro indoline group, when bound to a carbonyl, undergoes reaction upon exposure to light at 420 nm.

In a second alternative embodiment, the reactive group on the linker molecule is selected from a wide variety of negative light-reactive groups including a cinammate group.

Alternatively, the reactive group is activated or deactivated by electron beam lithography, x-ray lithography, or any other radiation. Suitable reactive groups for electron beam lithography include sulfonyl. Other methods may be used including, for example, exposure to a current source. Other reactive groups and methods of activation may be used in light of this disclosure.

As shown in FIG. 2, the linking molecules are preferably exposed to, for example, irradiation, such as light, through a suitable mask 14 using photolithographic techniques of the type known in the semiconductor industry and described in, for example, Sze, *VLSI Technology*, McGraw-Hill (1983), and Mead et al., *Introduction to VLSI Systems*, Addison-Wesley (1980), which are incorporated herein by reference for all purposes. The light may be directed at either the surface containing the protective groups or at the back of the substrate, so long as the substrate is transparent to the wavelength of light needed for removal of the protective groups. In the embodiment shown in FIG. 2, light is directed at the surface of the substrate containing the protective groups. FIG. 2 illustrates the use of such masking techniques as they are applied to a positive reactive group so as to activate linking molecules and expose functional groups in areas 16a and 16b.

The mask 14 is in one embodiment a transparent support material selectively coated with a layer of opaque material. Portions of the opaque material are removed, leaving opaque material in the precise pattern desired on the substrate surface. The mask is brought into close proximity with, imaged on, or brought directly into contact with the substrate surface as shown in FIG. 2. "Openings" in the mask correspond to locations on the substrate where it is desired to remove photoremovable protective groups from the substrate. Alignment may be performed using conventional alignment techniques in which alignment marks (not shown) are used to accurately overlay successive masks with previous patterning steps, or more sophisticated techniques may be used. For example, interferometric techniques such as the one described in Flanders et al., "A New Interferometric Alignment Technique," *App. Phys. Lett.* (1977) 31:426–428, which is incorporated herein by reference, may be used.

To enhance contrast of light applied to the substrate, it is desirable to provide contrast enhancement materials between the mask and the substrate according to some embodiments. This contrast enhancement layer may comprise a molecule which is decomposed by light such as quinone diazide or a material which is transiently bleached at the wavelength of interest. Transient bleaching of materials will allow greater penetration where light is applied, thereby enhancing contrast. Alternatively, contrast enhancement may be provided by way of a cladded fiber optic bundle.

The light may be from a conventional incandescent source, a laser, a laser diode, or the like. If non-collimated sources of light are used it may be desirable to provide a thick- or multi-layered mask to prevent spreading of the light onto the substrate. It may, further, be desirable in some embodiments to utilize groups which are sensitive to different wavelengths to control synthesis. For example, by using groups which are sensitive to different wavelengths, it is possible to select branch positions in the synthesis of a polymer or eliminate certain masking steps. Several reactive groups along with their corresponding wavelengths for deprotection are provided in Table 1.

TABLE 1

| Group | Approximate Deprotection Wavelength |
|---|---|
| Nitroveratryloxy carbonyl (NVOC) | UV (300–400 nm) |
| Nitrobenzyloxy carbonyl (NBOC) | UV (300–350 nm) |

TABLE 1-continued

| Group | Approximate Deprotection Wavelength |
|---|---|
| Dimethyl dimethoxybenzyloxy carbonyl | UV (280–300 nm) |
| 5-Bromo-7-nitroindolinyl | UV (420 nm) |
| o-Hydroxy-α-methyl cinnamoyl | UV (300–350 nm) |
| 2-Oxymethylene anthraquinone | UV (350 nm) |

Note that different photoprotected monomers, such as amino acids, can exhibit different photolysis rates. See, for example, "The Peptides, Analysis, Synthesis, Biology" Chapter 8, E. Gross and J. Meienhofer, Eds., Academic Press, Inc. (1980); and PCT application WO 89/10931. It may be desirable to utilize photoprotected monomers with substantially similar photolysis rates in a particular application. To obtain such a set of photoprotected monomers, one merely needs to select the appropriate photoprotecting group for each monomer in the set. In similar fashion, one can prepare a set of photoprotected monomers with substantially different photolysis rates (from monomer to monomer) by appropriate choice of photoprotecting groups.

While the invention is illustrated primarily herein by way of the use of a mask to illuminate selected regions the substrate, other techniques may also be used. For example, the substrate may be translated under a modulated laser or diode light source. Such techniques are discussed in, for example, U.S. Pat. No. 4,719,615 (Feyrer et al.), which is incorporated herein by reference. In alternative embodiments a laser galvanometric scanner is utilized. In other embodiments, the synthesis may take place on or in contact with a conventional liquid crystal (referred to herein as a "light valve") or fiber optic light sources. By appropriately modulating liquid crystals, light may be selectively controlled so as to permit light to contact selected regions of the substrate. Alternatively, synthesis may take place on the end of a series of optical fibers to which light is selectively applied. Other means of controlling the location of light exposure will be apparent to those of skill in the art.

The substrate may be irradiated either in contact or not in contact with a solution and is, preferably, irradiated in contact with a solution. The solution contains reagents to prevent the by-products formed by irradiation from interfering with synthesis of the polymer according to some embodiments. Such by-products might include, for example, carbon dioxide, nitrosocarbonyl compounds, styrene derivatives, indole derivatives, and products of their photochemical reactions. Alternatively, the solution may contain reagents used to match the index of refraction of the substrate. Reagents added to the solution may further include, for example, acidic or basic buffers, thiols, substituted hydrazines and hydroxylamines, reducing agents (e.g., NADH) or reagents known to react with a given functional group (e.g., aryl nitroso+glyoxylic acid→aryl formhydroxamate+$CO_2$).

Figure 3:
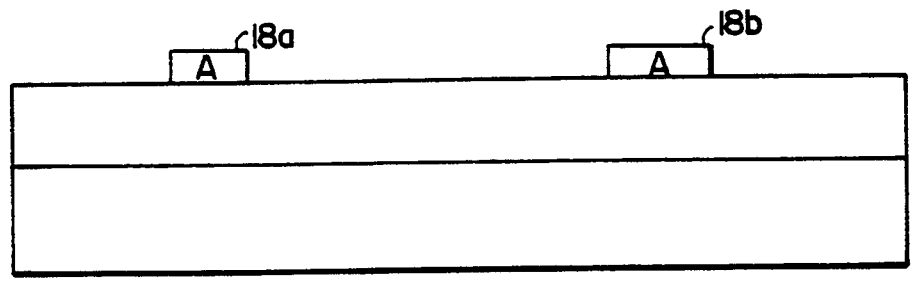

Either concurrently with or after the irradiation step, the linker molecules are washed or otherwise contacted with a first monomer, illustrated by "A" in regions 18a and 18b in FIG. 3. The first monomer reacts with the activated functional groups of the linker molecules which have been exposed to light. The first monomer, which is preferably an amino acid, is also provided with a photoprotective group. The photoprotecting group on the monomer may be the same as or different than the protecting group used in the linker molecules, and may be selected from any of the above-described protective groups. In one embodiment, the protective groups for the A monomer is selected from the group NBOC and NVOC.

Figure 4:
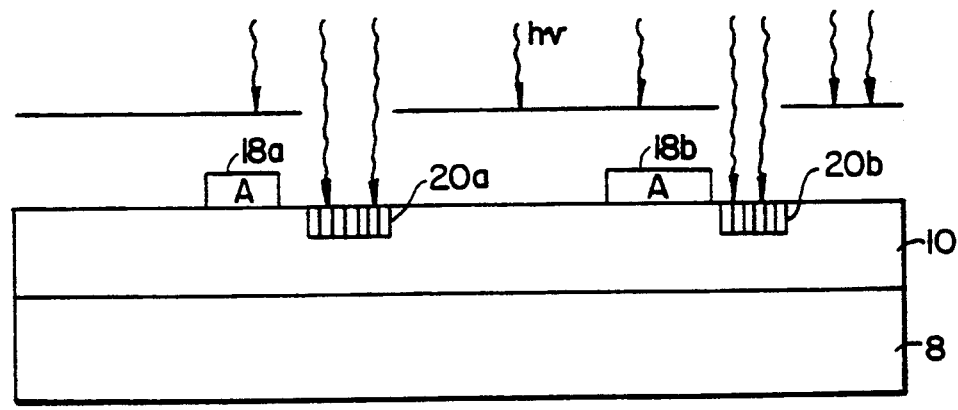

As shown in FIG. 4, the process of irradiating is thereafter repeated, with a mask repositioned so as to remove linkage protective groups and expose functional groups in regions 20a and 20b which are illustrated as being regions which were protected in the previous masking step. As an alternative to repositioning of the first mask, in many embodiments a second mask will be utilized. In other alternative embodiments, some steps may provide for illuminating a common region in successive steps. As shown in FIG. 4, it may be desirable to provide separation between irradiated regions. For example, separation of about 1-5 µm may be appropriate to account for alignment tolerances.

Figure 5:
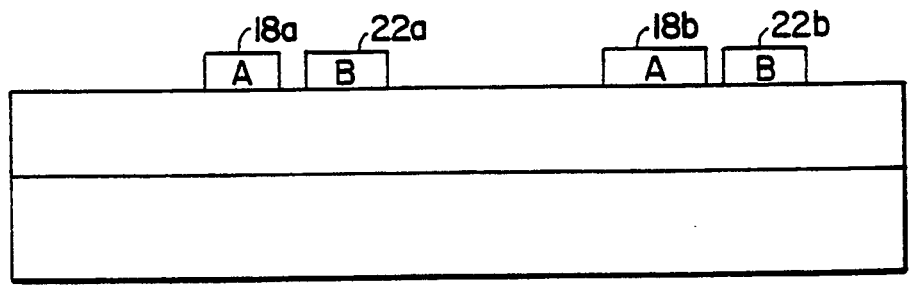
Figure 6:
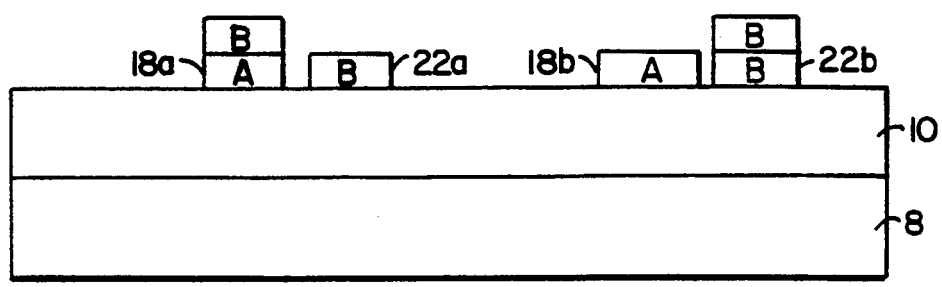

As shown in FIG. 5, the substrate is then exposed to a second protected monomer "B," producing B regions 22a and 22b. Thereafter, the substrate is again masked so as to remove the protective groups and expose reactive groups on A region 18a and B region 18b. The substrate is again exposed to monomer B, resulting in the formation of the structure shown in FIG. 6. The dimers B-A and B-B have been produced on the substrate.

Figure 7:
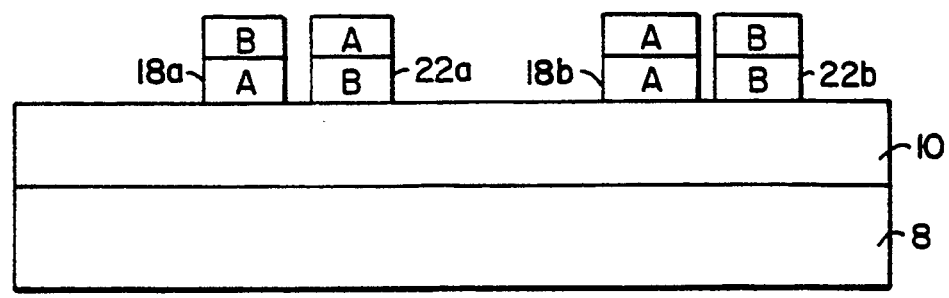

A subsequent series of masking and contacting steps similar to those described above with A (not shown) provides the structure shown in FIG. 7. The process provides all possible dimers of B and A, i.e., B-A, A-B, A-A, and B-B.

The substrate, the area of synthesis, and the area for synthesis of each individual polymer could be of any size or shape. For example, squares, ellipsoids, rectangles, triangles, circles, or portions thereof, along with irregular geometric shapes, may be utilized. Duplicate synthesis areas may also be applied to a single substrate for purposes of redundancy.

In some embodiments a single substrate supports more than about 10 different monomer sequences and perferable more than about 100 different monomer sequences, although in some embodiments more than about $10^3$, $10^4$, $10^5$, $10^6$, $10^7$, or $10^8$ different sequences are provided on a substrate. Of course, within a region of the substrate in which a monomer sequence is synthesized, it is preferred that the monomer sequence be substantially pure. In some embodiments, regions of the substrate contain polymer sequences which are at least about 1%, 5%, 10%, 15%, 20%, 25%, 30%, 35%, 40%, 45%, 50%, 60%, 70%, 80%, 90%, 95%, 96%, 97%, 98%, or 99% pure.

According to some embodiments, several sequences are intentionally provided within a single region so as to provide an initial screening for biological activity, after which materials within regions exhibiting significant binding are further evaluated.

2. Example

It is important to achieve good contrast between exposed and non-exposed regions on a substrate. Otherwise, unwanted products will be formed as, for example, when a monomer is added to a polymer in an unexposed or dark region. It has been determined that long exposure times will often result in more complete monomer coupling in activated regions. However, if the substrate is exposed for too long a period, the photolysis near the exposure edges will decrease, i.e., the contrast between exposed and unexposed regions will be reduced.

The deprotection of an NVOC-protected amine group was employed to model masking resolution.

The deprotection of the NVOC protected amine by ultraviolet light is a first order reaction of reactant A being converted to product B:

$$A \rightarrow B$$
$$\frac{dA}{dt} = kA$$

$$\ln A \bigg|\frac{A}{A_0} = \ln \frac{A}{A_0} = -kt$$

$$\frac{A}{A_0} = e^{-kt} = \%\ NVOC\ \text{protected amines after time}\ t$$

$$1 - \frac{A}{A_0} = 1 - e^{-kt} = \%\ \text{free amines at}\ t$$

where k is rate of photolysis=(physical constants)×I, and I is light intensity at 365 nm=13 mw/cm$^2$. A is the concentration of the reactant and $A_0$ is that concentration at t=0.

The dark areas were modelled as if they were being photolyzed with a fraction of the light intensity and a new rate of photolysis to the areas beyond the photolysis site was defined.

$$I' = CI$$
$$k' = Ck$$

$$r = \left(1 - \frac{A'}{A'_0}\right) = \frac{F_A}{F_B} = 1 - e^{-k't}$$

$$k' = \frac{-\ln(1 - r)}{t}$$

F is the height of the histogram used to analyze the experimental results. Thus, F is also the florescence intensity at a distance from the edge of photolysis.

Constrast was investigated by photolysis through a binary mask (12800 µm×x 6400 µm) for 660, 1320, and 9990 seconds. The contrast ratio was measured (as function of distance from the photolysis edge) as the ratio of the work height of the histogram in the dark area to the height of the histogram in the light area, i.e. FA/FB. The results are presented below.

| N | time | 0 µM | 50 µm | 100 µm | 200 µm |
|---|------|------|-------|--------|--------|
| 1 | 660 sec. | 1 | 0.4 | 0.1 | 0.01 |
| 2 | 1320 sec. | 1 | 0.7 | 0.3 | 0.03 |
| 3 | 9900 sec. | 1 | 0.92 | 0.7 | 0.39 |

Thus, it can be seen that the photolysis fidelity is a function of both the time of exposure and the distance from the edge.

2. Example - Slide Preparation

Before attachment of reactive groups it is preferred to clean the substrate which is, in a preferred embodiment, a glass substrate such as a microscope slide or cover slip. According to one embodiment the slide is soaked in an alkaline bath consisting of, for example, 1 liter of 95% ethanol with 120 ml of water and 120 grams of sodium hydroxide for 12 hours. The slides are then washed under running water and allowed to air dry, and rinsed once with a solution of 95% ethanol.

The slides are then aminated with, for example, aminopropyltriethoxysilane for the purpose of attaching amino groups to the glass surface on linker molecules, although any omega functionalized silane could also be used for this purpose. In one embodiment 0.1% aminopropyltriethoxysilane is utilized, although solutions with concentrations from $10^{-7}\%$ to 10% may be used, with about $10^{-3}\%$ to 2% preferred. A 0.1% mixture is prepared by adding to 100 ml of a 95% ethanol/5% water mixture, 100 microliters (μl) of aminopropyltriethoxysilane. The mixture is agitated at about ambient temperature on a rotary shaker for about 5 minutes. 500 μl of this mixture is then applied to the surface of one side of each cleaned slide. After 4 minutes, the slides are decanted of this solution and rinsed three times by dipping in, for example, 100% ethanol.

After the plates dry, they are placed in a 110°–120° C. vacuum oven for about 20 minutes, and then allowed to cure at room temperature for about 12 hours in an argon environment. The slides are then dipped into DMF (dimethylformamide) solution, followed by a thorough washing with dichloromethane.

The aminated surface of the slide is then exposed to about 500 μl of, for example, a 30 millimolar (mM) solution of NVOC-GABA (gamma amino butyric acid) - NHS (N-hydroxysuccinimide) in DMF for attachment of a NVOC-GABA to each of the amino groups.

The surface is washed with, for example, DMF, dichloromethane, and ethanol.

Any unreacted aminopropyl silane on the surface— that is, those amino groups which have not had the NVOC-GABA attached—are now capped with acetyl groups (to prevent further reaction) by exposure to a 1:3 mixture of acetic anhydride in pyridine for 1 hour. Other materials which may perform this residual capping function include trifluoroacetic anhydride, formicacetic anhydride, or other reactive acylating agents. Finally, the slides are washed again with DMF, methylene chloride, and ethanol.

3. Example - Synthesis of a Dimer of an AminopropylGroup and a Fluorescent Group In synthesizing the dimer of an aminopropyl group and a fluorescent group, a functionalized Durapore ™ membrane was used as a substrate. The Durapore ™ membrane was a polyvinylidine difluoride with aminopropyl groups. The aminopropyl groups were protected with the DDZ group by reaction of the carbonyl chloride with the amino groups, a reaction readily known to those of skill in the art. The surface bearing these groups was placed in a solution of THF and contacted with a mask bearing a checkerboard pattern of 1 mm opaque and transparent regions. The mask was exposed to ultraviolet light having a wavelength down to at least about 280 nm for about 5 minutes at ambient temperature, although a wide range of exposure times and temperatures may be appropriate in various embodiments of the invention. For example, in one embodiment, an exposure time of between about 1 and 5000 seconds may be used at process temperatures of between −70° and +50° C.

In one preferred embodiment, exposure times of between about 1 and 500 seconds at about ambient pressure are used. In some preferred embodiments, pressure above ambient is used to prevent evaporation.

The surface of the membrane was then washed for about 1 hour with a fluorescent label which included an active ester bound to a chelate of a lanthanide. Wash times will vary over a wide range of values from about a few minutes to a few hours. These materials fluoresce in the red and the green visible region. After the reaction with the active ester in the fluorophore was complete, the locations in which the fluorophore was bound could be visualized by exposing them to ultraviolet light and observing the red and the green fluorescence. It was observed that the derivatized regions of the substrate closely corresponded to the original pattern of the mask.

4. Example - Removal of NVOC and Attachment of a Fluorescent Marker

NVOC-GABA groups were attached as described above, except that the substrate was a glass slide. The entire surface of one slide was exposed to light so as to expose a free amino group at the end of the gamma amino butyric acid. This slide, and a duplicate which was not exposed, were then exposed to fluorescein isothiocyanate (FITC).

Figure 8A:
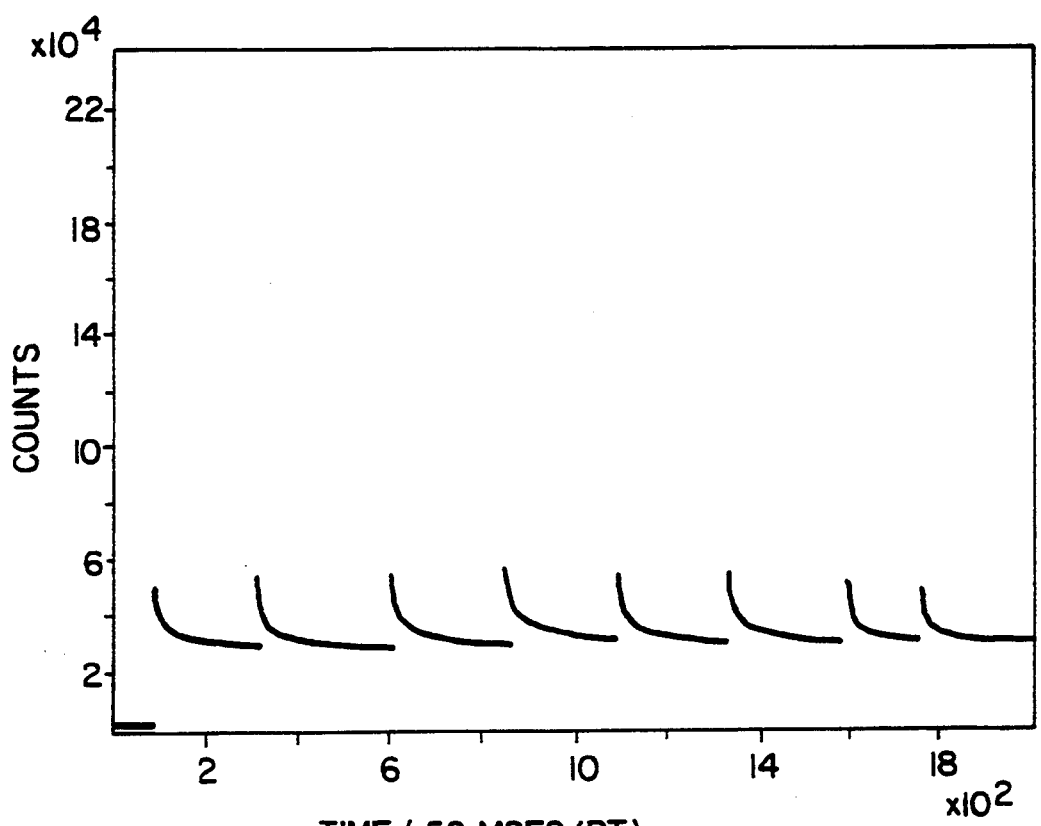
FIGS. 8A and 8B are fluorescence curves for NVOC slides not exposed and exposed to light respectively.
Figure 8B:
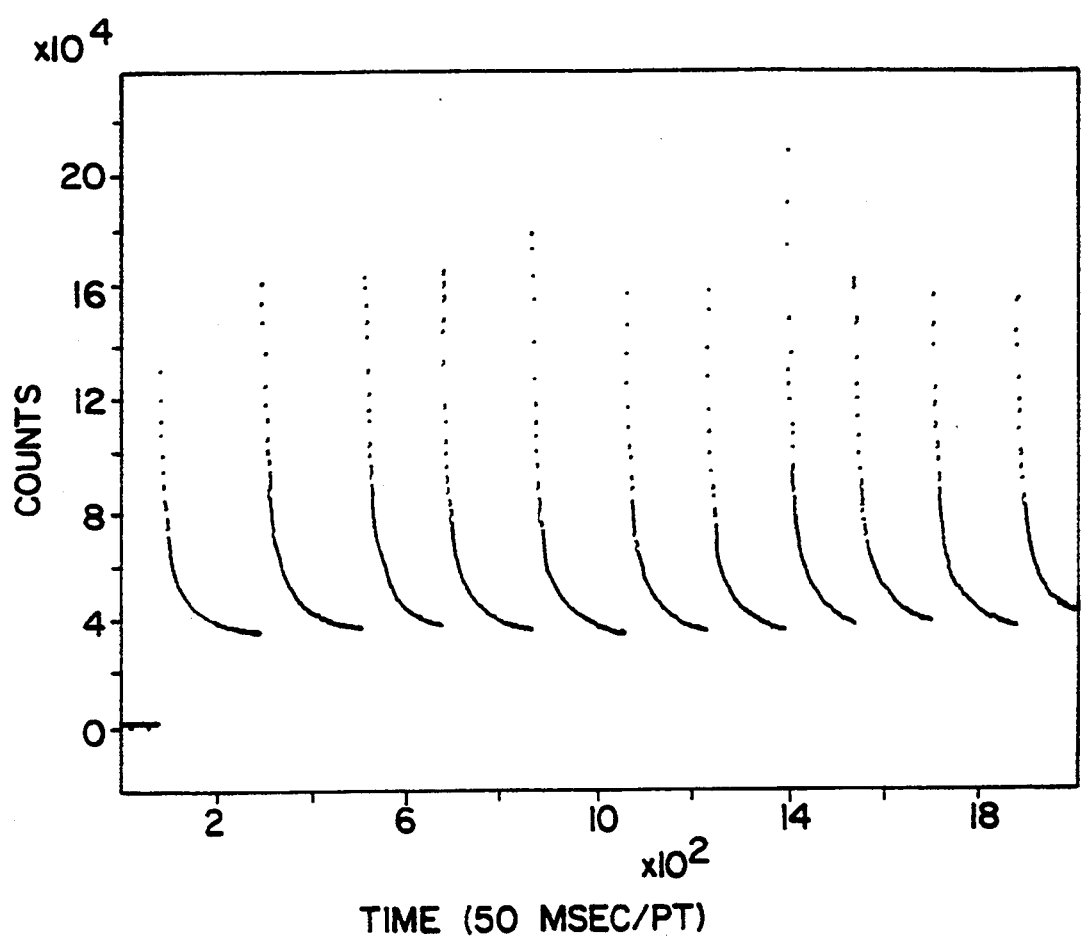

FIG. 8A illustrates the slide which was not exposed to light, but which was exposed to FITC. Fluorescence on the surface was measured by excitation using 488 nm laser light and photomultiplier detection through appropriate fluuorescein emission filters described in additional detail below. The units of the x axis are time (msec) and the units of the y axis are counts. The trace contains a certain amount of background fluorescence. The duplicate slide was exposed to 350 nm broadband illumination for about 1 minute (12 mW/cm$^2$, ∼350 nm illumination), washed and reacted with FITC. The fluorescence curves for this slide are shown in FIG. 8B. A large increase in the level of fluorescence is observed, which indicates photolysis has exposed a number of amino groups on the surface of the slides for attachment of a fluorescent marker.

5. Example - Use of a Mask in Removal of NVOC

The next experiment was performed with a 0.1% aminopropylated slide. Light from a Hg-Xe arc lamp was imaged onto the substrate through a laser-ablated chrome-on-glass mask in direct contact with the substrate.

Figure 9A:
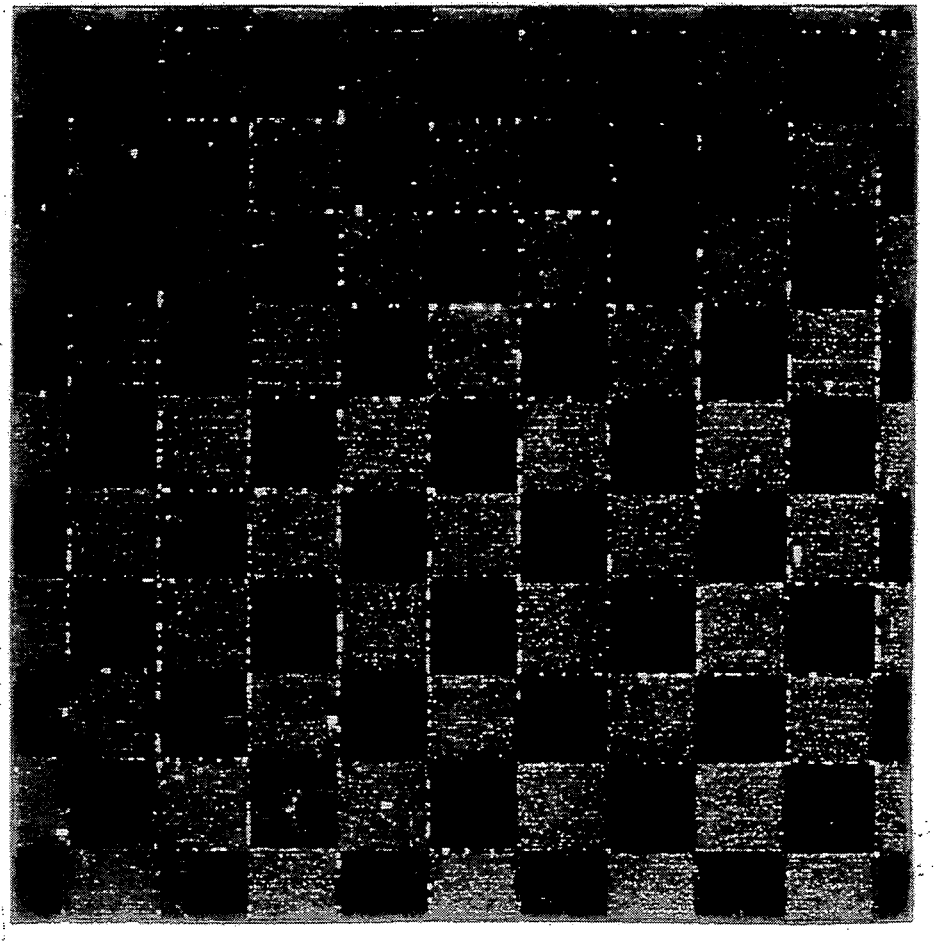
FIGS. 9A-9D are fluorescence plots of slides exposed through 100 μm, 50 μm, 20 μm and 10 μm masks.

This slide was illuminated for approximately 5 minutes, with 12 mW of 350 nm broadband light and then reacted with the 1 mM FITC solution. It was put on the laser detection scanning stage and a graph was plotted as a two-dimensional representation of position color-coded for fluorescence intensity. The fluorescence intensity (in counts) as a function of location is given on the color scale to the right of FIG. 9A for a mask having 100×100 μm squares.

Figure 9B:
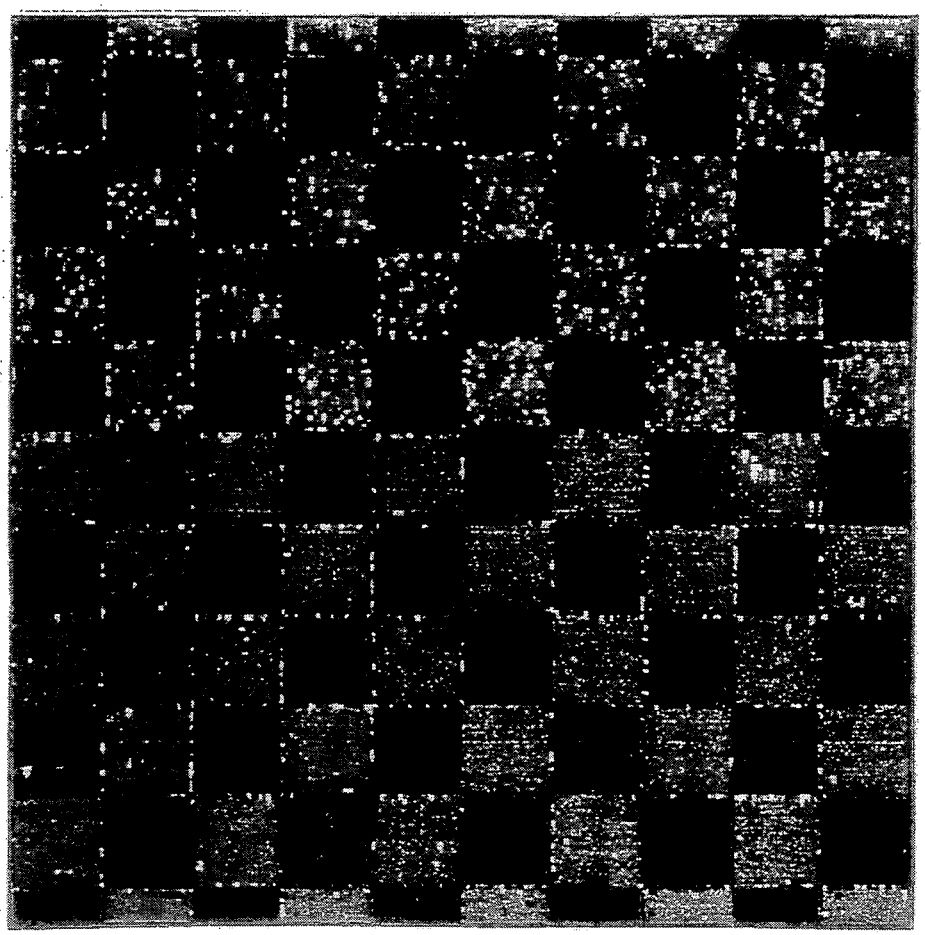
Figure 9C:
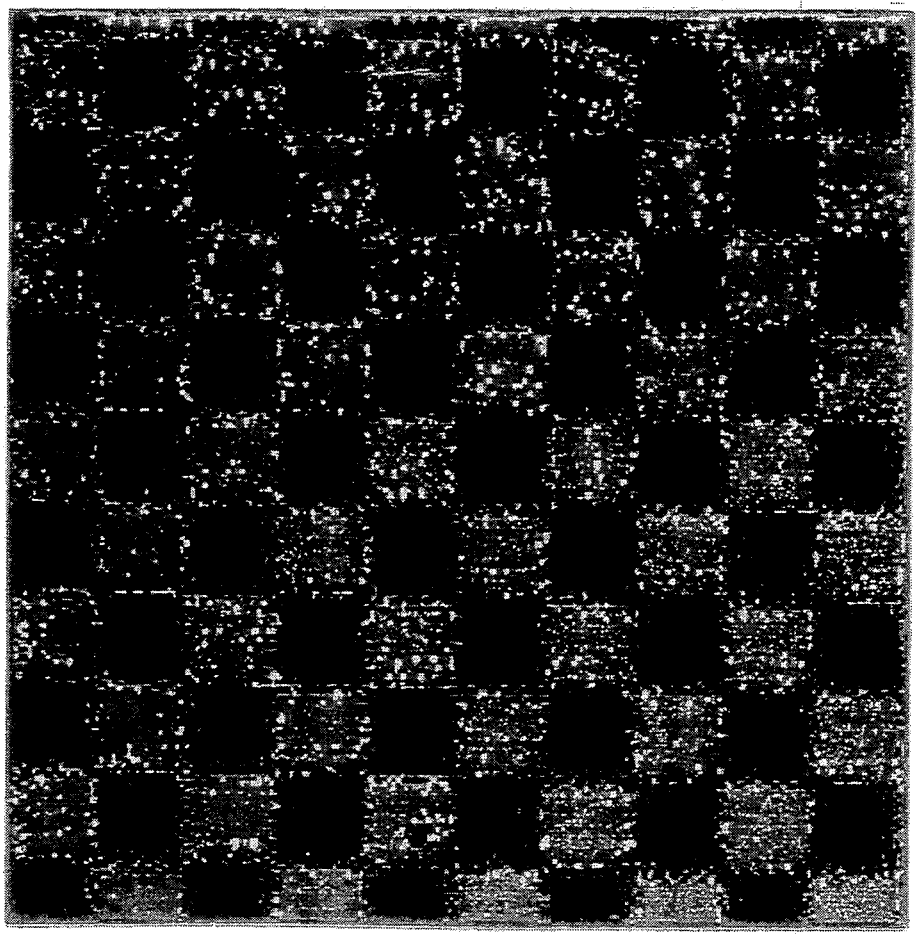
Figure 9D:
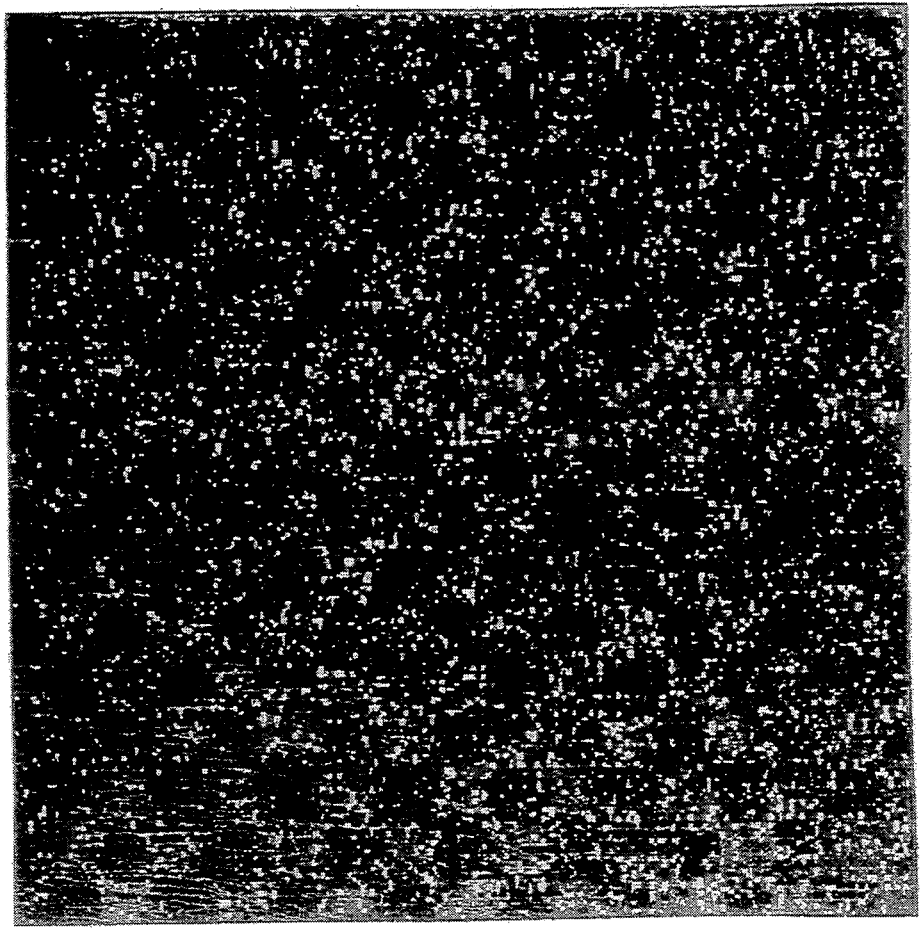

The experiment was repeated a number of times through various masks. The fluorescence pattern for a 50 μm mask is illustrated in FIG. 9B, for a 20 μm mask in FIG. 9C, and for a 10 μm mask in FIG. 9D. The mask pattern is distinct down to at least about 10 μm squares using this lithographic technique.

6. Example

In one example of the invention, free amino groups were fluorescently labelled by treatment of the entire substrate surface with fluorescein isothiocyanate (FITC) after photodeprotection. Glass microscope slides were cleaned, aminated by treatment with 0.1% aminopropyltriethoxysilane in 95% ethanol, and incubated at 110° C. for 20 min. The aminated surface of the slide was then exposed to a 30 mM solution of the N- hydroxysuccinimide ester of NVOC-GABA (nitroveratryloxycarbonyl-$\gamma$-amino butyric acid) in DMF. The NVOC protecting group was photolytically removed by imaging the 365 nm output from a Hg arc lamp through a chrome on glass 100 μm checkerboard mask onto the substrate for 20 min at a power density of 12 mW/cm$^2$. The exposed surface was then treated with 1 mM FITC in DMF. The substrate surface was scanned in an epifluorescence microscope (Zeiss Axioskop 20) using 488 nm excitation from an argon ion laser (Spectra-Physics model 2025). The fluorescence emission above 520 nm was detected by a cooled photomultiplier (Hamamatsu 943-02) operated in a photon counting mode. Fluorescence intensity was translated into a color display with red in the highest intensity and black in the lowest intensity areas. The presence of a high-contrast fluorescent checkerboard pattern of 100×100 μm elements revealed that free amino groups were generated in specific regions by spatially-localized photodeprotection.

7. Example

Slide preparation is illustrated below. Slides used in synthesis may be detergent cleaned, glass slides. Such glass slides may be, for example, 1"×3" smooth cut, 0.7 mm thick, anti-scratch coated, or 2Δ×3" smooth cut, 0.7 mm thick, anti-scratch coated from Erie Scientific. The slides are soaked in 10% Micro TM detergent (from Baxter), individually scrubbed, and immersed in deionized H$_2$O until all slides have been scrubbed. The slides are then subjected to 10 minute sonication in 70° C. "Micro" detergent and rinsed 10× with deionized H$_2$O. This process is followed by a 3 minute immersion in 70° C. 10% (w/v) NaOH. The slides are then rinsed 10× with deionized H$_2$O, followed by a 1 minute immersion in 1% HCl. The slides are then again rinsed 10× with deionized H$_2$O, followed by another 10 minute sonication in 70° C. deionized water and are rinsed 3–4× in deionized H$_2$O. The slides are then ethanol rinsed and dried with nitrogen or argon. The slides are then inspected visually for spots and scratches, preferably in a yellow light with a black background.

Alternatively or in addition, the slides are acid cleaned. The slides are loaded into teflon racks and subjected to a 30 minute immersion in Nochromix TM (Aldrich) solution with 36 g per liter of concentrated H$_2$SO$_4$, which is regenerated if discolored, filtered (glass fiber filter) to remove particulate matter, and provided with occasional agitation. The slides are then rinsed for 1 min. in deionized H$_2$O with vigorous agitation. The slides are then placed for 10 minutes in a rinse tank with 14 psi argon or nitrogen bubbling, a full open deionized water tap, and occasional agitation.

The slides are then immersed for 3 minutes in 70° C. 10%(w/v) NaOH, followed by a 1 minute rinse deionized H$_2$O with vigorous agitation, followed by 10 minutes in a rinse tank. The slides are then immersed for 1 min. in 1% HCl, and rinsed for 5 minutes in a rinse tank. The slides are then ethanol rinsed, dried with nitrogen or argon, and inspected visually for spots and scratches.

tBOC aminopropyl derivatization is illustrated below. The slides are loaded into plastic staining jars. Preferably the slides are completely dry, with 9 slides per jar. Silation reagents are then mixed as follows:

a pre-mix 1:10 mole ratio of tBOC-aminopropyltriethoxysilane:methyltriethoxysilane
tBOC-aminopropyltriethoxysilane:
MW=321.49
d=0.945 g/ml; and
methyltriethoxysilane:
MW=178.30
d=0.895 g/ml
1:10 ratio=1 ml tBOC-aminopropyl to 5.86 ml methyltriethoxysilane The reagents are kept anhydrous and stored under argon. The silation reagent is diluted to 1%(v/v) in dichloromethane (DCM), mixed well, and 60 ml per jar are added. The jars are capped and left overnight.

The silation solution is poured into a plastic container, rinsed with dichloromethane (DCM), and the slides are rinsed with toluene. The toluene is then poured off, and the slides are dried immediately with argon. The slides are loaded into glass drying racks, inspected for streaks, and allowed to stand for approximately 30 minutes.

The slides are then baked for 1 hour in 100° C. oven with the glass racks in metal trays covered with foil. The oven is preferably no hotter than 110° C. The slides are then cooled and numbered using an engraving tool.

Aminocaproic acid coupling is illustrated below. The tBOC-aminopropyl slides are loaded into glass staining jars with 15 slides per jar. The slides are then deprotected and neutralized with a 30 minute immersion in 50% TFA/DCM, a rinse for 2 minutes in DCM, and a rinse 2× in 5% DIEA/DCM; 5 minutes each, followed by a rinse with dichloromethane, and a rinse with ethanol. The slides are then dried with argon, and derivatized within one hour.

The volume of solution necessary is equal to 0.4 ml×# slides. The concentration of the solution is 100 mM NVOC-aminocaproic acid, 110 mM HOBT, 200 mM DIEA, and 100 mM BOC.

The slides are placed face up on glass plates, and 0.4 ml solution is layered per slide. The slides are then covered in plastic trays and allowed to sit for 2 hours. The slides are then rinsed with DMF or NMP, rinsed with DCM, and rinsed with EtOH.

The slides are capped with acetic anhydride by immersion for 1 hour in 25% acetic anhydride/pyridine and 0.1% DMAP. The slides are then rinsed with DMF or NMP, rinsed with DCM, and rinsed with EtOH. The slides are then dried with argon and stored in a light-tight container.

Biotinylation of NVOC-aminocaproic slides may be desirable in some instances (for example, see infra Section V.C.) and is achieved as follows. The slides are photolyzed in 5 mM H$_2$SO$_4$/dioxane with appropriate masking and a large area mercury illuminator with a 350–450 nm dichroic reflector and a 12 minute exposure at 12–13 mW/cm$^2$.

The slides are collected in dioxane until all slides have been exposed, washed 2× in 5% DIEA/DMF for 5 minutes each, and rinsed with DMF, DCM, and EtOH. The slides are then dried with argon, and are preferably derivatized within one hour.

The volume of solution necessary is equal to 0.4 ml×# slides. The concentration of the solutions is 100 mM Biotin, 110 mM HOBT, and 200 mM DIEA and 100 mM BOC. A heat gun is used to help dissolve biotin. 100 mM BOP (MW=442.29) is dissolved in 1/10th final volume NMP or DMF. The solutions are mixed, capped, and allowed to stand 10 minutes. The final volume is adjusted with NMP or DMF and the solutions are mixed well.

The slides are placed face up on glass plates, and 0.4 ml solution per slide is layered onto the slide. The slides are covered in plastic trays, allowed to sit for 2 hours, and rinsed with NMP or DMF, then rinsed with DCM, then rinsed with EtOH, and dried with argon.

FITC labeling of amines is achieved as follows. First the amines are deprotected and neutralized by photolyzing NVOC-aminocaproic slides. The photolysis takes place in 5 mM $H_2SO_4$/dioxane with appropriate masking using a large area illuminator with a 350–450 nm dichroic reflector, 12–13 mW/cm$^2$, and a 12 minute exposure. The slides are rinsed in dioxane, and then rinsed 2× in 5% DIEA/DMF; 5 minutes each. The slides are then rinsed with DMF.

Deprotected amines are labeled by immersing slides in 1 mM FITC/DMF for 1 hour, rinsing with DMF, rinsing with DCM, rinsing with ethanol, and drying slides with argon.

B. Antibody Recognition

In one preferred embodiment the substrate is used to determine which of a plurality of amino acid sequences is recognized by an antibody of interest.

For purposes of increasing the signal-to-noise ratio of the technique, some embodiments of the invention provide for exposure of the substrate to a first labeled or unlabeled receptor followed by exposure of a labeled, second receptor (e.g., an antibody) which binds at multiple sites on the first receptor. If, for example, the first receptor is an antibody derived from a first species of an animal, the second receptor is an antibody derived from a second species directed to epitopes associated with the first species. In the case of a mouse antibody, for example, fluorescently labeled goat antibody or antiserum which is antimouse may be used to bind at multiple sites on the mouse antibody, providing several times the fluorescence compared to the attachment of a single mouse antibody at each binding site. This process may be repeated again with additional antibodies (e.g., goat-mouse-goat, etc.) for further signal amplification.

1. Example - Attachment of YGGFL and Subsequent Exposure to Herz Antibody and Goat Antimouse In order to establish that receptors to a particular polypeptide sequence would bind to a surface-bound peptide and be detected, t-BOC protected Leu enkephalin was coupled to the surface and recognized by an antibody. A slide was derivatized with 0.1% amino propyl-triethoxysilane and protected with NVOC-6-amino caproic acid or NVOC-GABA. A 500 μm checkerboard mask was used to expose the slide in a flow cell using backside contact printing. The Leu enkephalin sequence ($H_2$N-tyrosine,glycine,glycine,-phenylalanine, leucine-$CO_2$H, otherwise referred to herein as YGGFL (Seq.ID No: 1) was attached via its carboxy end to the exposed amino groups on the surface of the slide. The peptide was added in DMF solution with the BOP/HOBT/DIEA coupling reagents and recirculated through the flow cell for 2 hours at room temperature, A first antibody, known as the Herz antibody, was applied to the surface of the slide for 45 minutes at 2 μg/ml in a supercocktail (containing 1% BSA and 1% ovalbumin also in this case). A second antibody, goat anti-mouse fluorescein conjugate, was then added at 2 μg/ml in the supercocktail buffer, and allowed to incubate for 2 hours.

Figure 10:
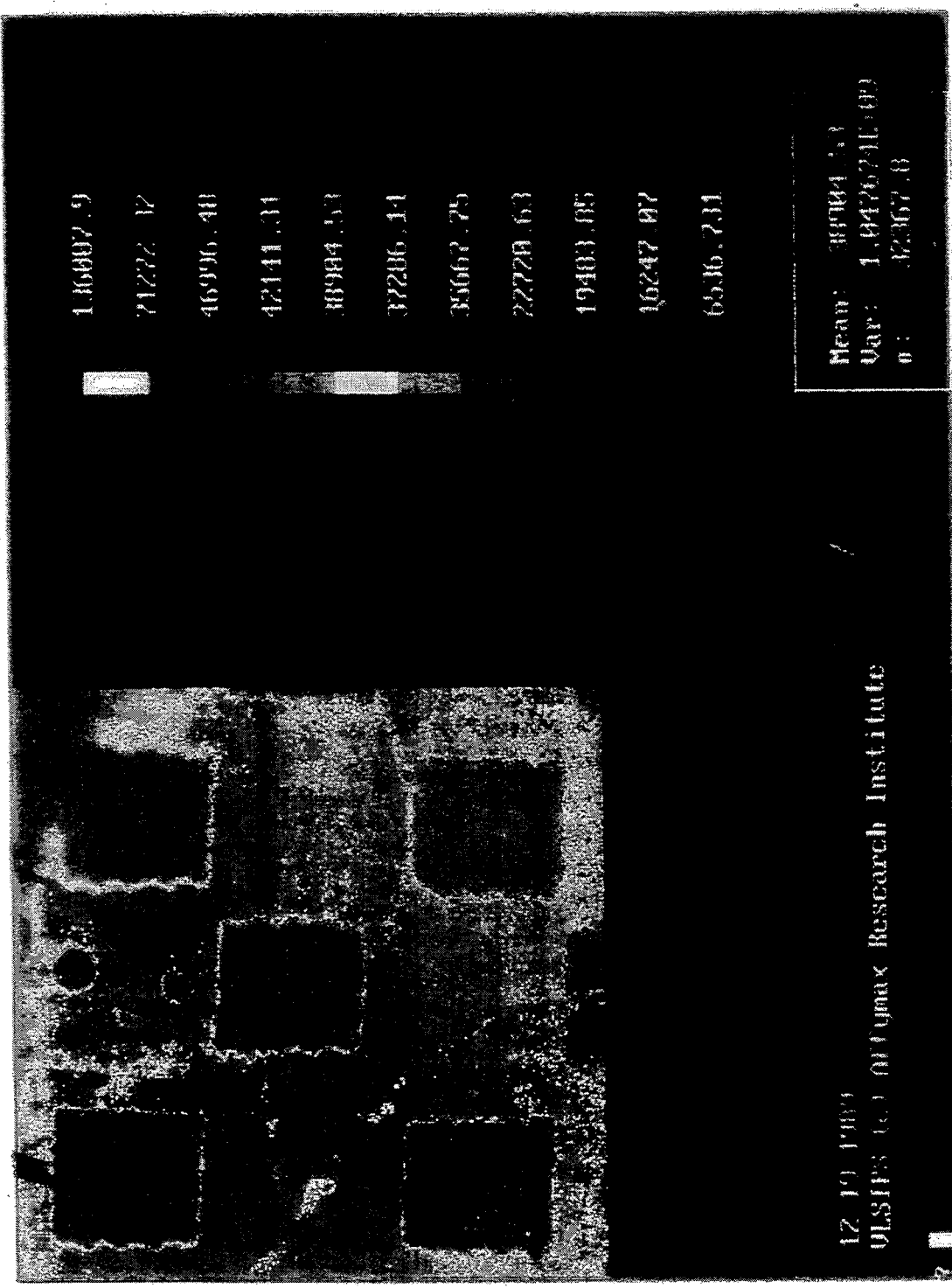
FIG. 10 illustrates fluorescence of a slide with the peptide YGGFL (SEQ ID NO: 1) on selected region of its surface which has been exposed to labeled Herz antibodies specific for the sequence.

The results of this experiment are obtained by taking a fluorescence scan obtained using a fluorescence detection system. Again, FIG. 10 illustrates fluorescence intensity as a function of position. The fluorescence scale is shown on the right, according to the color coding. This image was taken at 10 μm steps. This figure indicates that not only can deprotection be carried out in a well defined pattern, but also that (1) the method provides for successful coupling of peptides to the surface of the substrate, (2) the surface of a bound peptide is available for binding with an antibody, and (3) that the detection apparatus capabilities are sufficient to detect binding of a receptor.

2. Example

Figure 11:
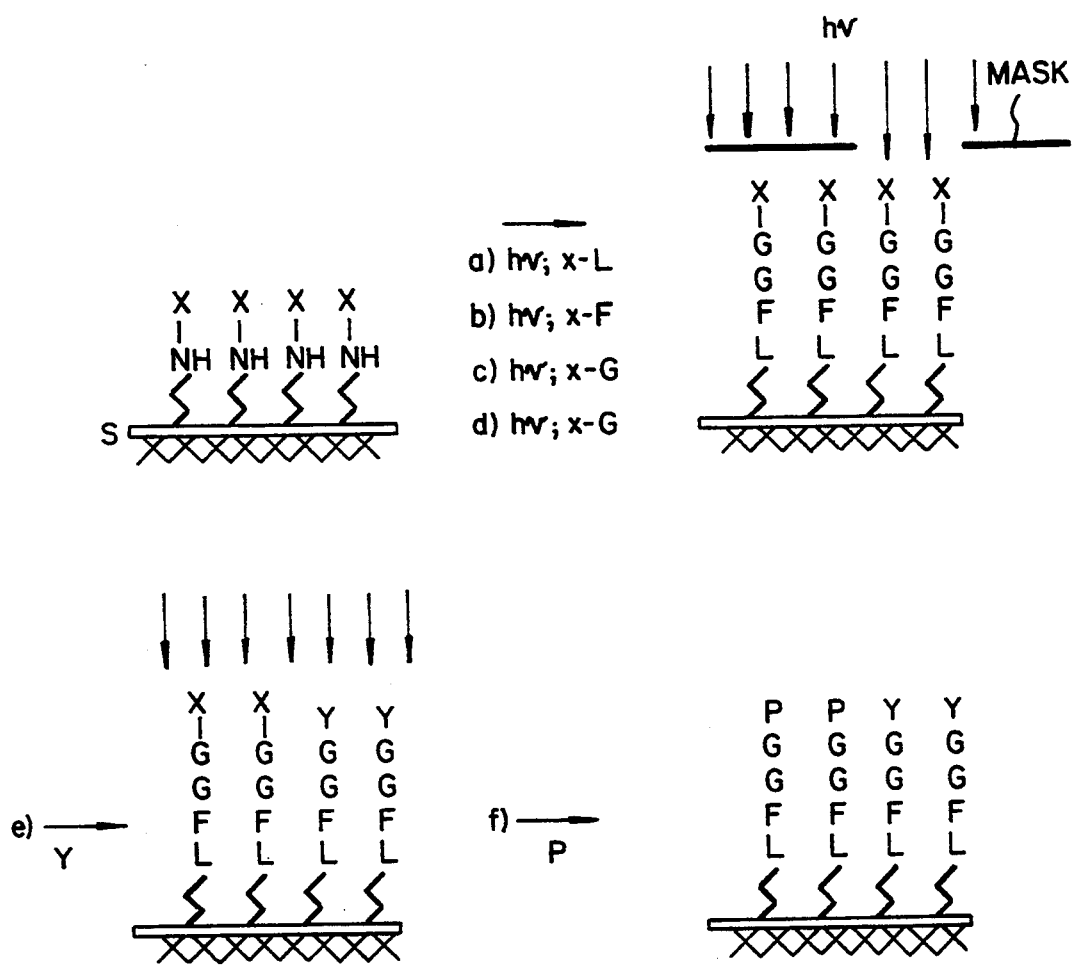
FIG. 11 schematically illustrates one example of light-directed peptide synthesis.

FIG. 11 is a flow chart illustrating another example of the invention. Carboxy-activated NVOC-leucine was allowed to react with an aminated substrate. The carboxy activated HOBT ester of leucine and other amino acids used in this synthesis was formed by mixing 0.25 mmol of the NVOC amino protected amino acid with 37 mg HOBT (1-hydroxybenzotriazole), 111 mg BOP (benzotriazolyl-n-oxy-tris (dimethylamino)-phosphoniumhexa-fluorophosphate) and 86 μl DIEA (diisopropylethylamine) in 2.5 ml DMF. The NVOC protecting group was removed by uniform illumination. Carboxy-activated NVOC-phenylalanine was coupled to the exposed amino groups for 2 hours at room temperature, and then washed with DMF and methylene chloride. Two unmasked cycles of photodeprotection and coupling with carboxy-activated NVOC-glycine were carried out. The surface was then illuminated through a chrome on glass 50 μm checkerboard pattern mask. Carboxy-activated Nα-tBOC-O-tButyl-L-tyrosine was then added. The entire surface was uniformly illuminated to photolyze the remaining NVOC groups. Finally, carboxy-activated NVOC-L-proline was added, the NVOC group was removed by illumination, and the t-BOC and t-butyl protecting groups were removed with TFA. After removal of the protecting groups, the surface consisted of a 50 μm checkerboard array of Tyr-Gly-Gly-Phe-Leu (YGGFL) and Pro-Gly-Gly-Phe-Leu (PGGFL). See also SEQ ID NO:1 and SEQ ID NO:2.

Figure 12:
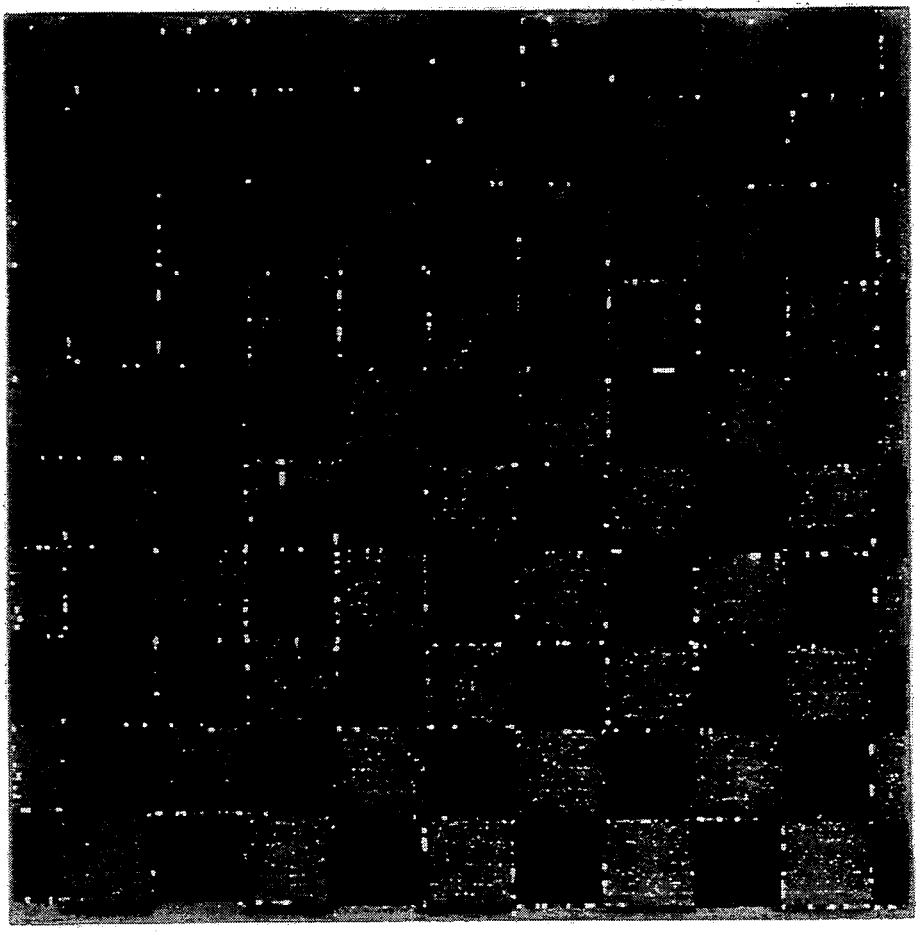
FIG. 12 is a fluorescence plot of YGGFL (SEQ ID NO: 1) and PGGFL synthesized in a 50 μm checkerboard pattern.

The array of pentapeptides was probed with a mouse monoclonal antibody directed against β-endorphin. This antibody (called 3E7) is known to bind YGGFL and YGGFM (see also SEQ ID NO:1 and SEQ ID NO:21) with nanomolar affinity and is discussed in Meo et al., *Proc. Natl. Acad. Sci. USA* (1983) 80:4084, which is incorporated by reference herein for all purposes. This antibody requires the amino terminal tyrosine for high affinity binding. The array of peptides formed as described in FIG. 11 was incubated with a 2 μg/ml mouse monoclonal antibody (3E7) known to recognize YGGFL. See also SEQ ID NO:1. 3E7 does not bind PGGFL. See also SEQ ID NO:2. A second incubation with fluoresceinated goat anti-mouse antibody labeled the regions that bound 3E7. The surface was scanned with an epi-fluorescence microscope. As shown in FIG. 12, results showed alternating bright and dark 50 μm squares indicating that YGGFL (SEQ ID NO:1) and PGGFL (SEQ ID NO:2) were synthesized in a geometric array determined by the mask. A high contrast (>12:1 intensity ratio) fluorescence checkerboard image shows that (a) YGGFL (SEQ ID NO:1) and PGGFL (SEQ ID NO:2) were synthesized in alternate 50 μm squares, (b) YGGFL (SEQ ID NO:1) attached to the surface is accessible for binding to antibody 3E7, and (c) antibody 3E7 does not bind to PGGFL (SEQ ID NO:2)

A three-dimensional representation of the fluorescence intensity data in a 2 square by 4 square rectangular portion of the checkerboard was also produced. It showed that the border between synthesis sites is sharp. The height of each spike in this display is linearly proportional to the integrated fluorescence intensity in a 2.5 μm pixel. The transition between PGGFL and YGGFL occurs within two spikes (5 μm). There is little variation in the fluorescence intensity of different YGGFL squares. The mean intensity of sixteen YGGFL synthesis sites was $2.03 \times 10^5$ counts and the standard deviation was $9.6 \times 10^3$ counts.

3. Example-Monomer-by-Monomer Formation of YGGFL and Subsequent Exposure to Labeled Antibody Monomer-by-monomer synthesis of YGGFL and GGFL in alternate squares was performed on a slide in a checkerboard pattern and the resulting slide was exposed to the Herz antibody. This experiment and the results thereof are illustrated in FIGS. 13A, 13B, 13C, and 13D.

Figure 13A:
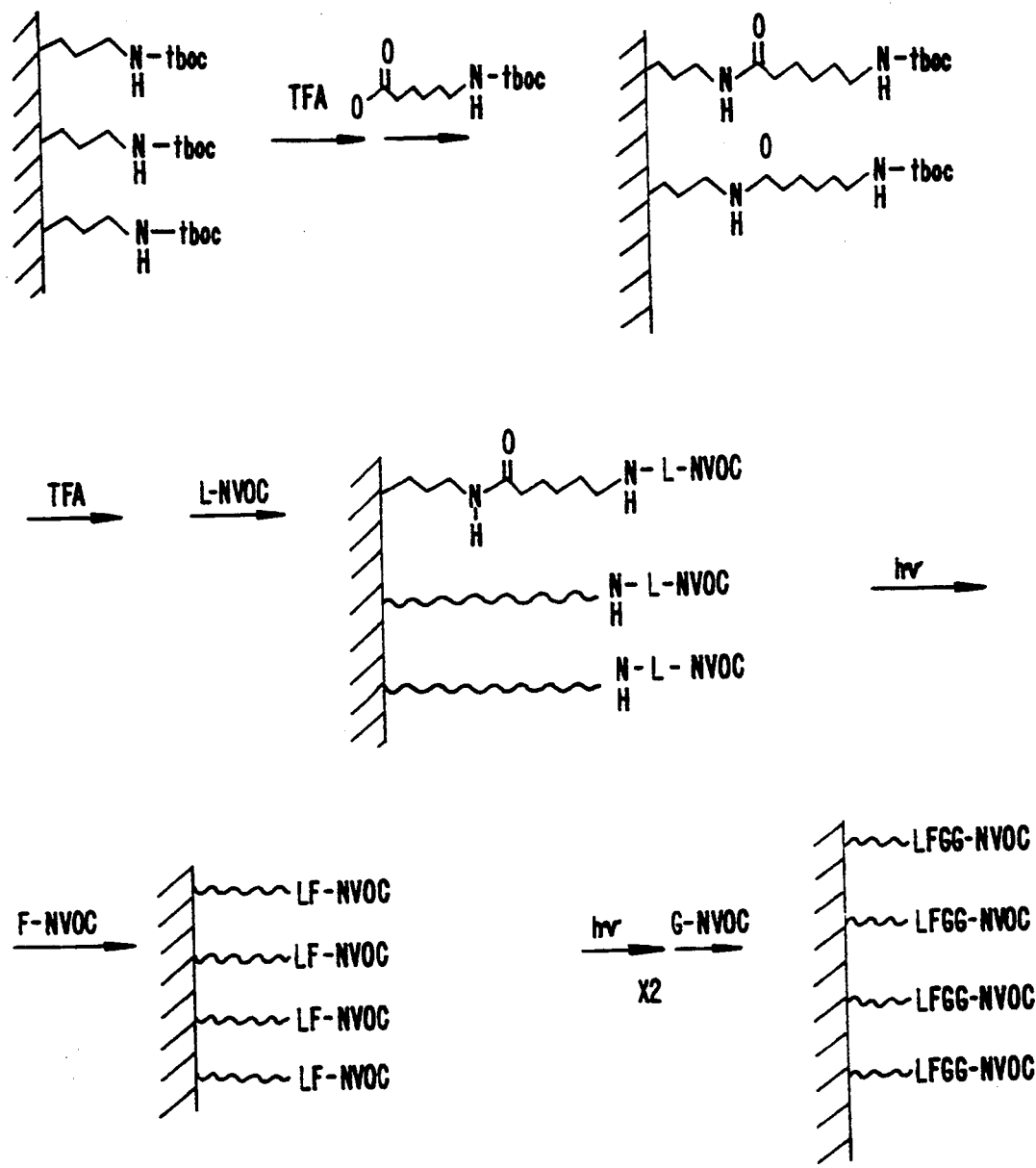
FIGS. 13A-13D illustrate formation and screening of a checkerboard pattern of YGGFL (SEQ ID NO: 1) and GGFL (SEQ ID NO: 15)

In FIG. 13A, a slide is shown which is derivatized with t-BOC-aminopropyl-triethoxysilane. The slide was treated with TFA to remove the t-BOC protecting group. t-BOC-6-aminocaproic acid was then coupled onto the aminopropyl groups. The aminocaproic acid serves as a spacer between the aminopropyl group and the peptide to be synthesized. The amino end of the spacer was deprotected and coupled to NVOC-Leucine. The entire slide was then illuminated with 12 mW of 325 nm broadband illumination. The slide was then coupled with NVOC-Phenylalanine and washed. The entire slide was again illuminated, then coupled to NVOC-Glycine and washed. The slide was again illuminated and coupled to NVOC-Glycine to form the sequence shown in the last portion of FIG. 13A.

Figure 13B:
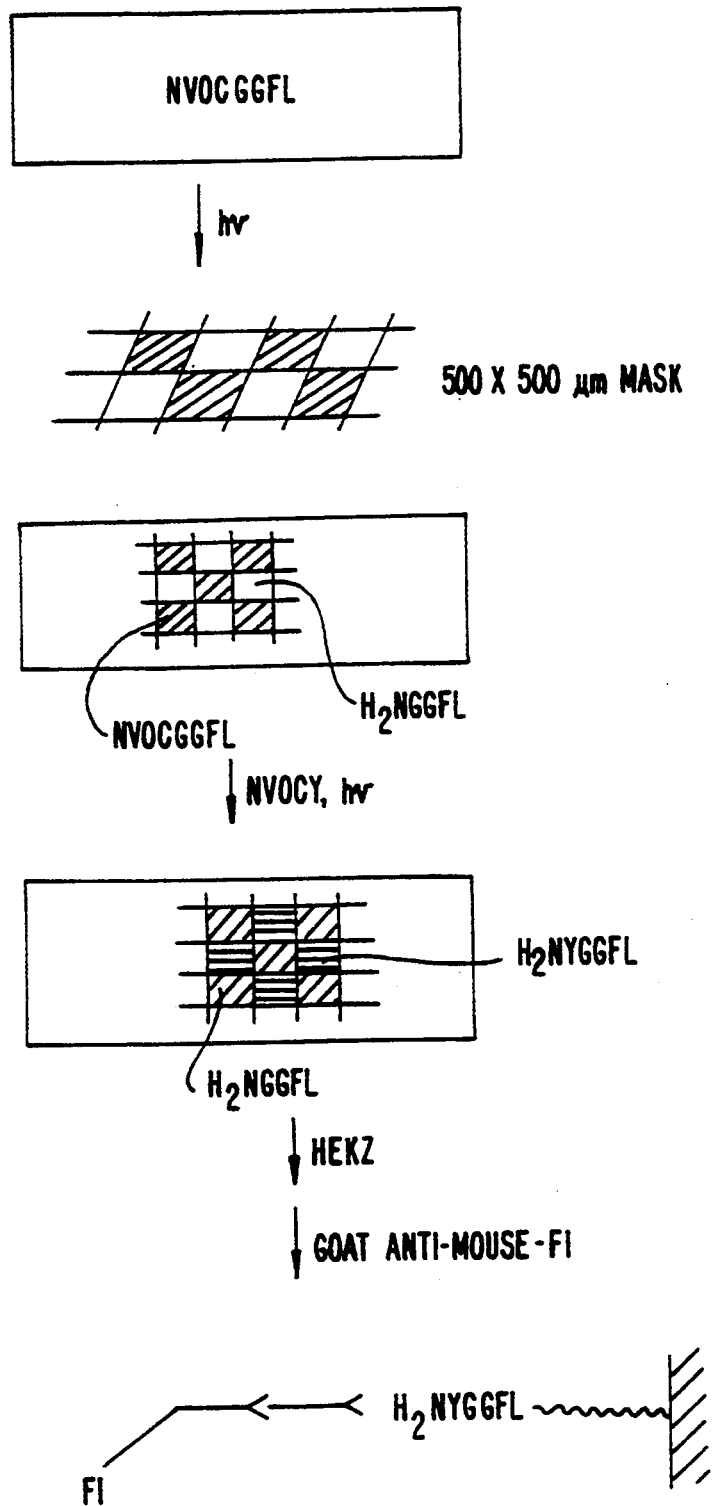

As shown in FIG. 13B, alternating regions of the slide were then illuminated using a projection print with a 500×500 μm checkerboard mask; thus, the amino group of Glycine was exposed only in the lighted areas. When the next coupling chemistry step was carried out, NVOC-Tyrosine was added, and it coupled only at those spots which had received illumination. The entire slide was then illuminated to remove all the NVOC groups, leaving a checkerboard of YGGFL in the lighted areas and in the other areas, GGFL (SEQ ID NO: 15). The Herz antibody (which recognizes the YGGFL, but not GGFL) was then added, followed by goat anti-mouse fluorescein conjugate.

Figure 13C:
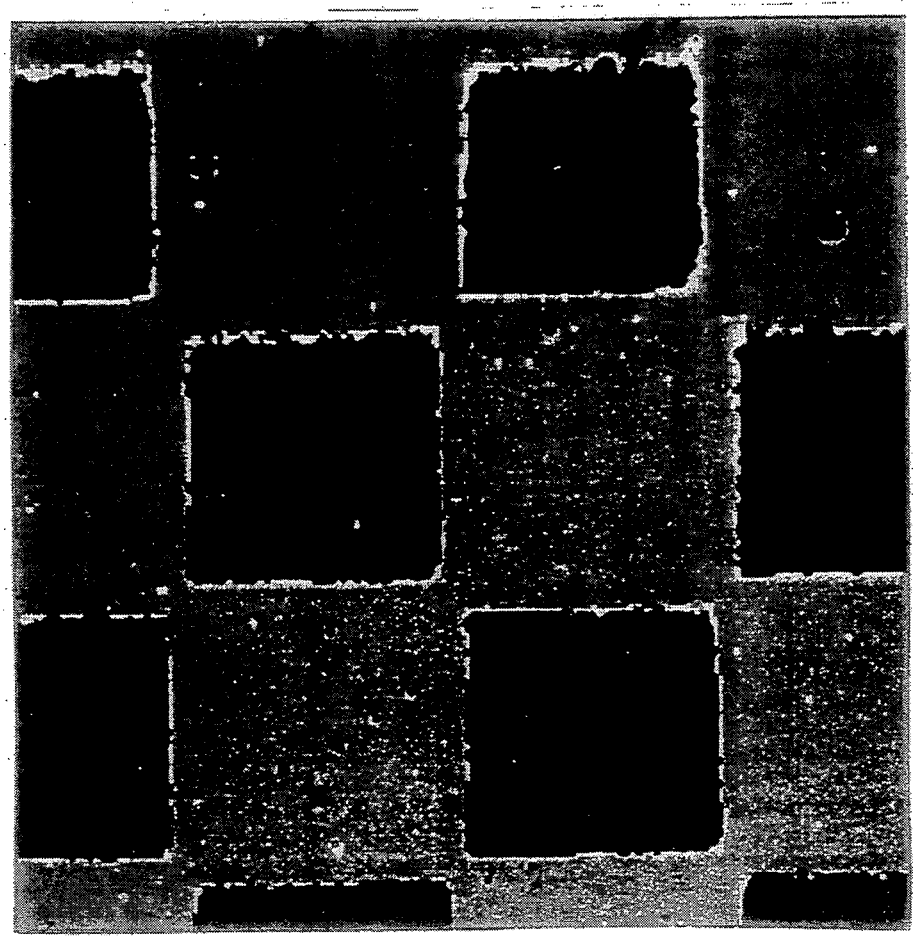

The resulting fluorescence scan is shown in FIG. 13C, and the color coding for the fluorescence intensity is again given on the right. Dark areas contain the tetrapeptide GGFL, which is not recognized by the Herz antibody (and thus there is no binding of the goat anti-mouse antibody with fluorescein conjugate), and in the red areas YGGFL is present. The YGGFL pentapeptide is recognized by the Herz antibody and, therefore, there is antibody in the lighted regions for the fluorescein-conjugated goat anti-mouse to recognize.

Figure 13D:
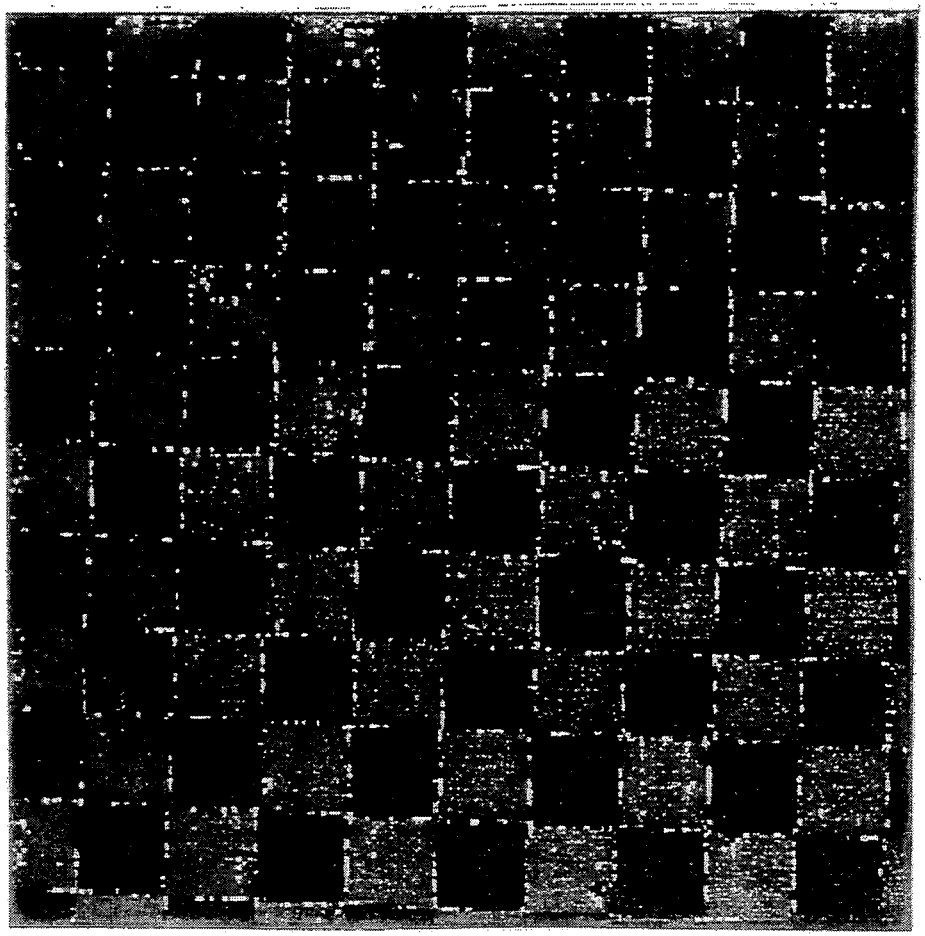

Similar patterns are shown for a 50 μm mask used in direct contact ("proximity print") with the substrate in FIG. 13D. Note that the pattern is more distinct and the corners of the checkerboard pattern are touching when the mask is placed in direct contact with the substrate (which reflects the increase in resolution using this technique).

4. Example - Monomer-by-Monomer Synthesis of YGGFL and YPGGFL

Figure 14:
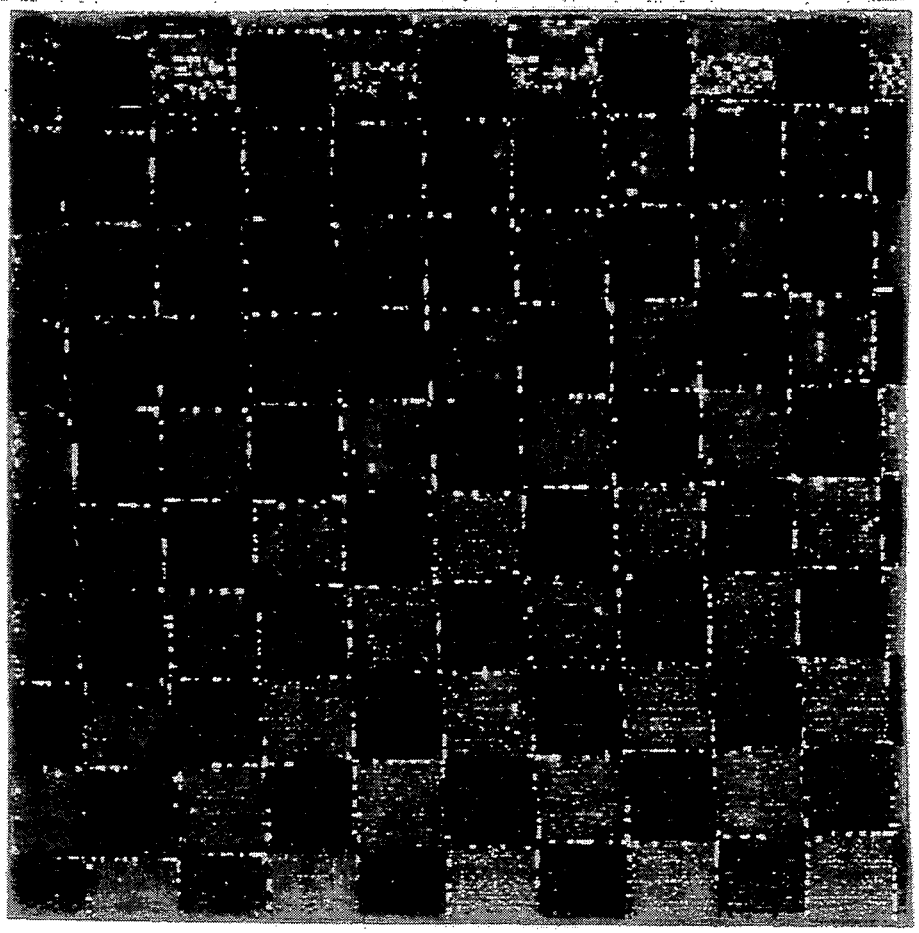
FIG. 14 is a fluorescence plot of YPGGFL (SEQ ID NO: 15) and YGGFL (SEQ ID NO: 1synthesized in a 50 μm checkerboard pattern.

In order to further demonstrate the operability of the invention, a 50 μm checkerboard pattern of alternating YGGFL and YPGGFL (SEQ ID NO: 3) was synthesized on a substrate using techniques like those set forth above. The resulting fluorescence plot is provided in FIG. 14. Again, it is seen that the antibody is clearly able to recognize the YGGFL sequence and does not bind significantly at the YPGGFL regions.

5. Example - Synthesis of an Array of Sixteen Different Amino Acid Sequences and Estimation of Relative Binding Affinity to Herz Antibody Using techniques similar to those set forth above, an array of 16 different amino acid sequences (replicated four times) was synthesized on each of two glass substrates. The sequences were synthesized by attaching the sequence NVOC-GFL across the entire surface of the slides. Using a series of masks, two layers of amino acids were then selectively applied to the substrate. Each region had dimensions of 0.25 cm ×0.0625 cm. The first slide contained amino acid sequences containing only L amino acids while the second slide contained selected D amino acids. FIGS. 15A and 15B illustrate a map of the various regions on the first and second slides, respectively. The patterns shown in FIGS. 15A and 15B were duplicated four times on each slide. The slides were then exposed to the Herz antibody and fluorescein-labeled goat anti-mouse.

Figure 16:
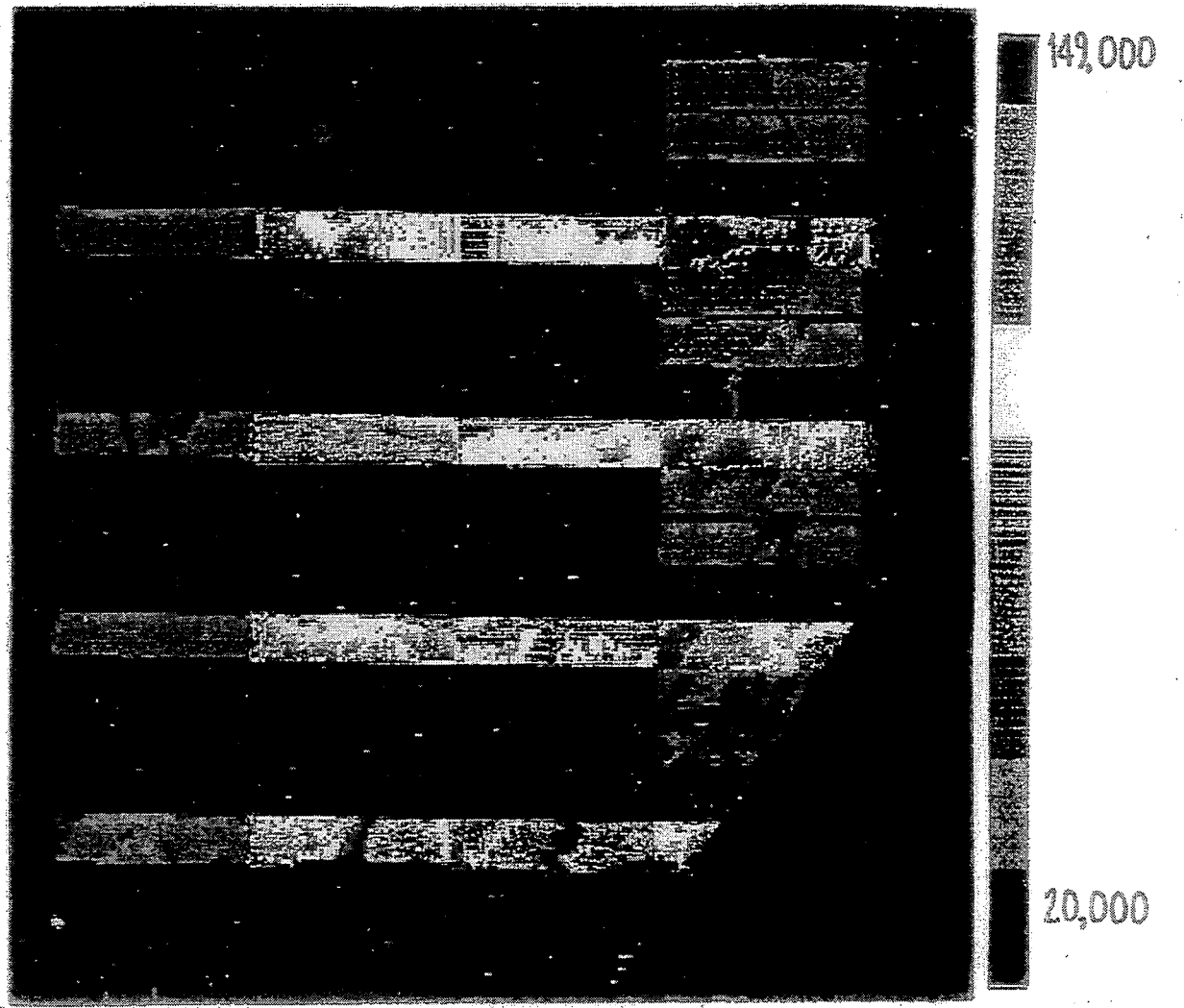
FIG. 16 is a fluorescence plot of the slide illustrated in FIG. 15A.

FIG. 16 is a fluorescence plot of the first slide, which contained only L amino acids. Red indicates strong binding (149,000 counts or more) while black indicates little or no binding of the Herz antibody (20,000 counts or less). The bottom right-hand portion of the slide appears "cut off" because the slide was broken during processing. The sequence YGGFL is clearly most strongly recognized. The sequences YAGFL and YSGFL also exhibit strong recognition of the antibody. By contrast, most of the remaining sequences show little or no binding. The four duplicate portions of the slide are extremely consistent in the amount of binding shown therein.

Figure 17:
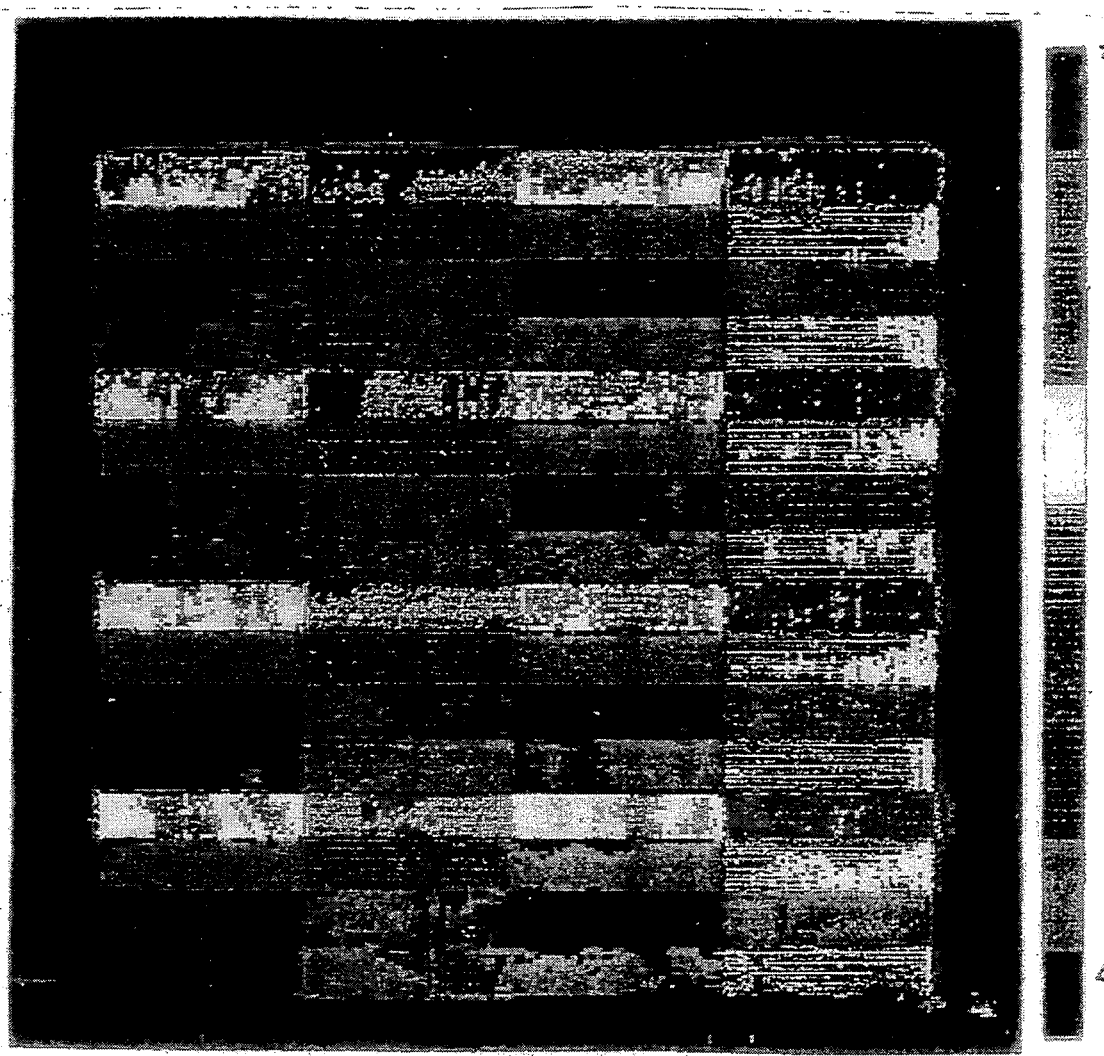
FIG. 17 is a fluorescence plot of the slide illustrated in FIG. 15B.

FIG. 17 is a fluorescence plot of the second slide. Again, strongest binding is exhibited by the YGGFL sequence. Significant binding is also detected to YaGFL(SEQ ID NO: 22), YsGFL(SEQ ID NO: 23), and YpGFL(SEQ ID NO: 24). The remaining sequences show less binding with the antibody. Note the low binding efficiency of the sequence yGGFL.

Table 2 lists the various sequences tested in order of relative fluorescence, which provides information regarding relative binding affinity. In the table, lower case letters represent D-amino acids.

TABLE 2

| Apparent Binding to Herz Ab | |
|---|---|
| L-a.a. Set | D-a.a. Set |
| YGGFL | YGGFL |
| YAGFL | YaGFL |
| YSGFL | YsGFL |
| LGGFL (SEQ ID NO: 25) | YpGFL |
| FGGFL (SEQ ID NO: 26) | fGGFL |
| YPGFL | yGGFL |
| LAGFL (SEQ ID NO: 27) | faGFL |
| FAGFL (SEQ ID NO: 28) | wGGFL |
| WGGFL (SEQ ID NO: 29) | yaGFL |
| | fpGFL |

TABLE 2-continued

| Apparent Binding to Herz Ab | |
|---|---|
| L-a.a. Set | D-a.a. Set |
| | waGFL |

6. Example

Figure 18:
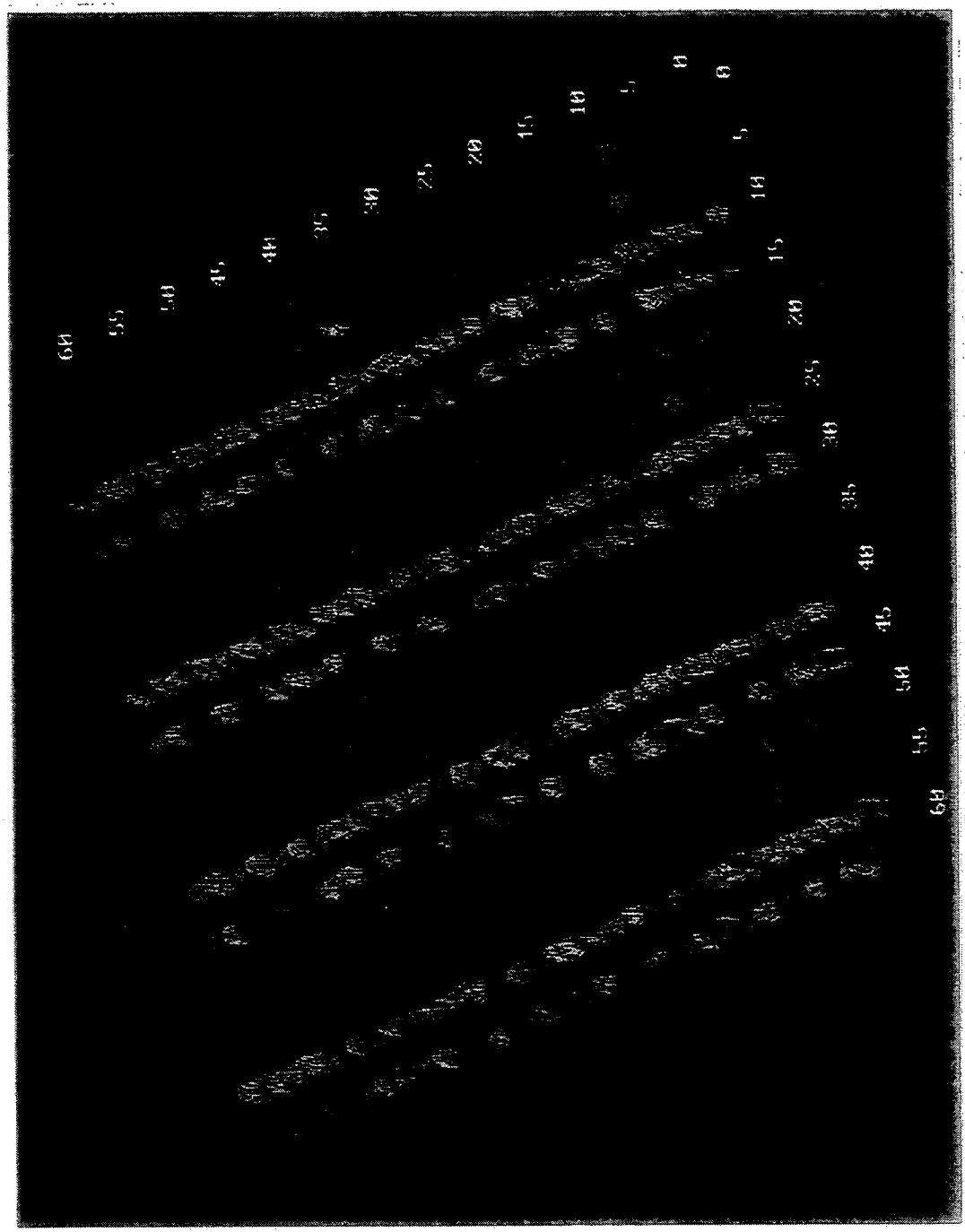
FIG. 18 is a fluorescence plot of an experiment which produced 4,096 compounds.

A 4096 compound experiment was conducted similarly to detailed Example 7. The building blocks used were: Y, G, P, A, F, W, G, F, M, Q, L, and S. Since G and F are repeated there are 4072 peptides. This chip was stained with Herz 3E7 IgG and then FITC-labelled goat anti-mouse IgG. A substrate used in this experiment was 700 μm thick. The results are shown in FIG. 18.

7. Example

In order to generate 65,536 different compounds (including one null compound) in a minimum number of chemical steps, a sixteen step binary masking strategy was used. The building blocks chosen were (from amino to carboxy): r, R, H, Q, P, F, Homophenylalanine, N, Ornithine, A, V, v, T, S, and G (lower case letters represent D-amino acids). This experiment shows that unnatural amino acids can be used as building blocks.

Once the masking strategy and the building blocks were chosen, the amino acids were weighed into cartridges obtained from ABI (Applied Biosystems Inc., Foster City, CA). For this experiment the flow cell volume was 0.5 ml, and thus 15 mg of HOBJ and 44 mg of BOP was used. During synthesis the amino acid were dissolved in 1.5 ml of solvent so that the flow cell was full of amino acid solution during coupling. The final amino acid concentration was 60 mM.

Next a process file was generated on the program "PS" (copy provided in Appendix 3). This was done by hitting F1 (if an IBM computer is being used to run the program) to "initialize masking sequence." "Binary process minimum movement" was chosen and then the program asked for input the building blocks in order of C terminus to N terminus. The first building block that was input that goes onto the chip first, in this case S. The program allows for input of the names in either one letter or three letter codes. Using a binary process with minimum movement, one does not have to select the mask that will be used, as the program will select the mask. For a sixteen-step binary synthesis the following masks are used in the order given: mask A offset 0, mask A offset 1, mask B offset 0, mask B offset 1, mask C offset 0, mask C offset 1, mask D offset 0, mask D offset 1, mask E offset 0, mask E offset 1, mask F offset 0, mask F offset 1, mask G offset 0, mask G offset 1, mask H offset 0, and mask H offset 1. The masking sequence was then saved to disk so that it could be used during data workup.

The exposure lamp was turned on and the shutter set for 11 minutes. The lamp power was set to about 12mW/cm$^2$ at 365 nm. The lamp was warmed up for about an hour before the experiment began. Meanwhile, the mask was cleaned with methanol and the mirror was aligned.

Next, the ABI peptide synthesizer was set up. Of course, other peptide synthesizers can be used, e.g., one commercially available from Milligen, Inc. All of the reagent bottles were filled and an empty cartridge was placed under the injector. The amino acid cartridges were then loaded from the N-terminus on the left to the C-terminus on the right. The synthesizer modules to be used were then entered through synthesizer interface. In this case the following sequence was used: HEBDCDFDCCD. This sequence is repeated sixteen times for a sixteen step synthesis.

H is the photolysis module. The slide was rinsed with p-dioxane and then rinsed twice in 5 mM $H_2SO_4$ in p-dioxane. The flow cell was then filled with 5 mM $H_2SO_4$ in p-dioxane for photolysis. A relay was sent to the personal computer telling it to open the lamp shutter. The shutter opens and remains open for 11 minutes. During this time a 5% DIEA in DMF solution was made in the peptide synthesizer's activator vessel. Module E begins before the photolysis is completed. The first part of module E starts the dissolution of the amino acid in the cartridge. A 7% DIEA/DMF solution was delivered to the cartridge and the solution was mixed by Argon bubbling. The cartridge is mixed for about six minutes. Next the carbridge solution was further diluted with anhydrous DMF and mixed some more. By this point the photolysis was completed.

Module B, the substrate activation module, first rinsed the slide with p-dioxane six times. Then it rinsed the slide with DMF. Next, an aliquot of the 5% DIEA/DMF solution made in the activator vessel was moved to the flow cell where it sats for 100 seconds. This step was repeated six times and the flow cell was drained.

Module D washed the slide with DMF and washed the slide with dichloromethane followed by ethanol. Hence, the slide was washed with DMF, dichloromethane and ethanol, and finally DMF again.

Next chemical coupling occurred using module F. The amino acid solution was taken from the cartridge and put into the flow cell where it sat for 1.5 hours. After coupling was completed, the slide was then washed using modules D, C, C, and D. This is the end of one synthesis cycle. As mentioned above, this sequence of modules was repeated fifteen more times for a sixteen step synthesis.

In use, the flow cell was set up and a substrate was chosen. In this case a 160 μm thick slide derivatized with an NVOC-6-aminocaproic acid linker was used. The slide was placed on the flow cell and the vacuum was turned on. The flow cell transfer lines were attached to the synthesizer. The slide and flow cell was checked for leaks using a methylene chloride wash. This also served to rinse the slide. Next, the outer surface of the slide were cleaned with methanol. The flow cell was then attached to the synthesis mount and placed flush against the mask.

The synthesis then began. "Begin synthesis" was pressed on "PS," (copy provided in Appendix 3) with the exposure time set to 660 seconds. After the mask moved to its first position, the ABI was started. This synthesis took about 48 hours, since each cycle was three hours.

Once the synthesis was completed, the slide underwent a final photolysis to remove all of the NVOC groups on the slide. Modules HIBDCD were used, with IA "wait" step. Since it is desirable to photolyze the entire slide, the flow cell with the attached substrate was taken off of the synthesis mount and physically placed under the lamp. After the photolysis was complete, it was put back so that the remaining modules would go smoothly. The flow cell was in a vertical position to ensure total coverage of the substrate with solutions.

The amino groups were capped by final photolysis with acetic anhydride. This process is called acetylation.

After final photolysis and capping, the side chain protecting groups on the amino acids were removed. The slide was taken off of the flow cell and treated with a trifluoracetic acid solution containing phenol, thioanisole, and ethanedithiol as scavengers. After sidegroup deprotection the slide was neutralized in a 5% DIEA/methylene chloride solution twice for five minutes each. The slide was then rinsed with methylene chloride, DMF, and ethanol.

Next, the slide was incubated with 3 ml of anti-dynorphin B antibody (8 micrograms/ml) and 1% BSA in PBS (containing 0.08% Tween 20 TM) for two hours. After rinsing twice with PBS, the slide was stained with FITC-labelled goat anti-mouse antibody (10 micrograms/ml) in 1% BSA/PBS for 1.5 hours. After the second staining, the slide was rinsed twice with PBS/Tween 20 TM and once with deionized water.

Next the slide was scanned using the fluorescence detection system. Scanning parameters depend on the type of image being scanned. In this case since each synthesis site is only 50 $\mu$m, the slide was scanned very slowly with a small increment size. Typical parameters were 3000×3000 @5 $\mu$m steps, 5 $\mu$m/ms, 220 $\mu$m/ms$^2$.

Figure 19:
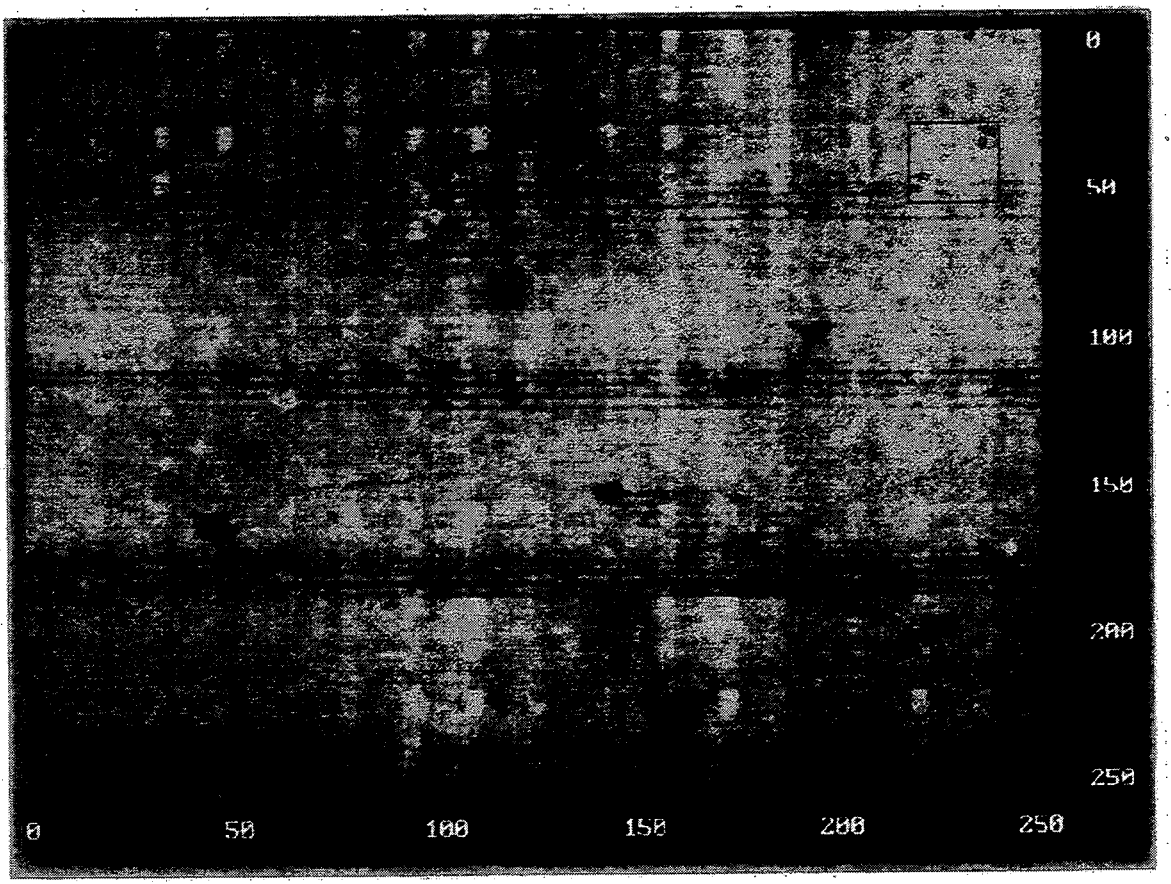
FIG. 19 is a fluorescence plot of a substrate on which 65,536 different compounds were formed.

Once the fluorescence images were obtained, the data file was converted to a tiff file and analyzed using a program called "avi" (attached as Appendix 1) which has a module that integrates each synthesis site. It then made a file containing fluorescence versus location information. Then another program called "pepserch" (attached as Appendix 2) was used to combine the fluorescence information with compound identity. In this experiment the largest peptide synthesis was 16 amino acids in length, and 65,536 (including the null) peptides (including monomers) were synthesized. The results are shown in FIG. 19.

C. Fluorescence Energy-Transfer Substrate Assays

A different application of the present invention tests for catalytic cleavage of various polymer sequences by an enzyme or other catalyst. For example, aspartyl proteases such as renin, HIV proteases, elastase, collagenase and some cathepsins can be tested against an array of peptides. According to this aspect of the invention, a variety of peptide sequences are synthesized on a solid substrate by the protection-deprotection strategy outlined above. The resulting array is probed with an enzyme which might cleave one or more peptide elements of the array-resulting in a detectable chain.

Figure 20A:
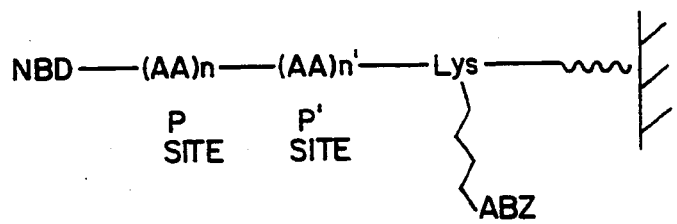
FIGS. 20A and 20B show a tripeptide used in a fluorescence energy-transfer substrate assay and that substrate after cleavage.
Figure 20B:
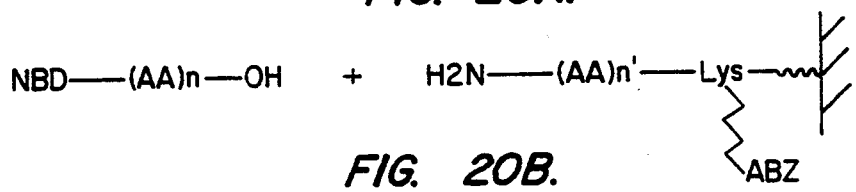

In one embodiment, the peptides to be tested have a fluorescence donor group such as 1-aminobenzoic acid (anthranilic acid or ABZ) or aminomethylcoumarin (AMC) located at one position on the peptide and a fluorescence quencher group such as lucifer yellow, methyl red or nitrobenzo-2-oxo-1,3-diazole (NBD) at a different position near the distal end of the peptide. Note, that some "donor" groups can also serve as "quencher" groups, depending on the relative excitation and emission frequencies of the particular pair selected. The intramolecular resonance energy transfer from the fluorescence donor molecule to the quencher will quench the fluorescence of the donor molecule. Upon cleavage, however, the quencher is separated from the donor group, leaving behind a fluorescent fragment. Plus, a scan of the surface with an epifluorescence microscope for example, will show bright regions where the peptide has been cleaved. As an example, FIG. 20A shows a tripeptide having a donor-quencher pair on a substrate. The fluorescence donor molecule, 1-aminobenzoic acid (ABZ), is coupled to the e-amino group of lysine (Lys) on the P' side of the substrate. The donor molecule could, of course, be attached to the $\alpha$-amine group. A fluorescence quencher, NBD caproic acid is coupled to the P side of the substrate molecule. Upon cleavage by a protease as shown in FIG. 20B, the quencher is released leaving the fluorescent type fragment still bound to the solid substrate for detection.

Figure 22A:
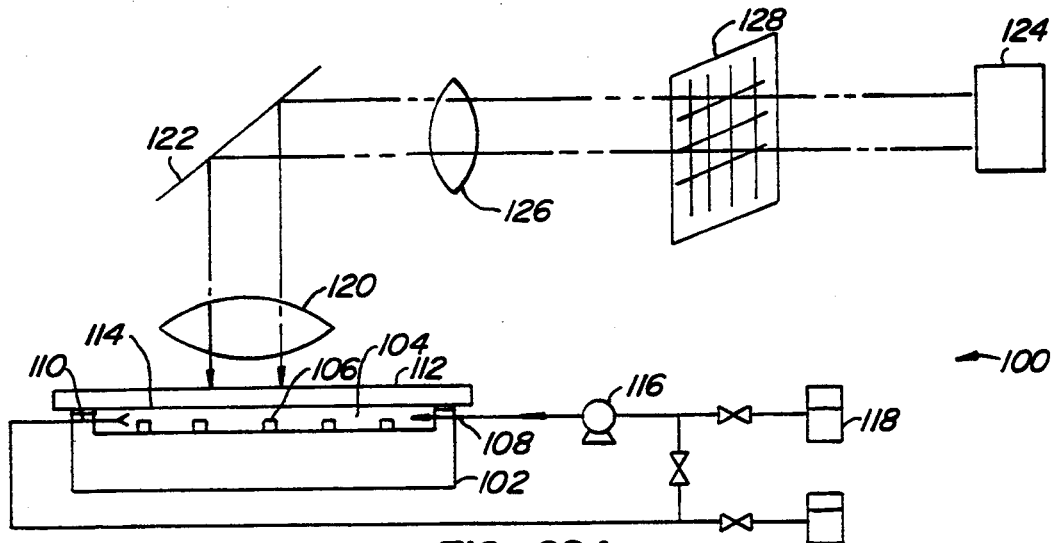
FIGS. 22A and 22B illustrate alternative embodiments of a reactor system for forming a plurality of polymers on a substrate.

FIG. 21 demonstrates the fluorescence donor-quencher resonance energy transfer assay for two quenchers. In FIG. 21A the bright outer circle is produced by fluorescence from benzyloxycarbonyl protected 1-aminobenzoic acid linked to a slide through lysine and a linker. The dark inner circle shows the quenching effect of methyl red. FIG. 21B shows a similar result, with the dark inner circle resulting from the quenching effect of NBD-caproic acid. III. Synthesis A. Reactor System FIG. 22a schematically illustrates a preferred embodiment of a reactor system 100 for synthesizing polymers on the prepared substrate in accordance with one aspect of the invention. The reactor system includes a body 102 with a cavity 104 on a surface thereof. In preferred embodiments the cavity 104 is between about 50 and 1000 $\mu$m deep with a depth of about 500 $\mu$m preferred.

The bottom of the cavity is preferably provided with an array of ridges 106 which extend both into the plane of the Figure and parallel to the plane of the Figure. The ridges are preferably about 50 to 200 $\mu$m deep and spaced at about 2 to 3 mm. The purpose of the ridges is to generate turbulent flow for better mixing. The bottom surface of the cavity is preferably light absorbing so as to prevent reflection of impinging light.

A substrate 112 is mounted above the cavity 104. The substrate is provided along its bottom surface 114 with a photoremovable protecting group such as NVOC with or without an intervening linker molecule. The substrate is preferably transparent to a wide spectrum of light, but in some embodiments is transparent only at a wavelength at which the protecting group may be removed (such as UV in the case of NVOC). The substrate in some embodiments is a conventional microscope glass slide or cover slip. The substrate is preferably as thin as possible, while still providing adequate physical support. Preferably, the substrate is less than about 1 mm thick, more preferably less than 0.5 mm thick, more preferably less than 0.1 mm thick, and can be less than 0.05 mm thick. In alternative preferred embodiments, the substrate is quartz, silicon, or other compounds such as a silicon nitride.

The substrate and the body serve to seal the cavity except for an inlet port 108 and an outlet port 110. The body and the substrate may be mated for sealing in some embodiments with one or more gaskets. According to one embodiment, the body is provided with two concentric gaskets and the intervening space is held at vacuum to ensure mating of the substrate to the gaskets.

Fluid is pumped through the inlet port into the cavity by way of a pump 116 which may be, for example, a model no. B-120-S made by Eldex Laboratories, from fluid supply 118. Selected fluids are circulated into the cavity by the pump, through the cavity, and out the outlet for recirculation or disposal. The reactor may be subjected to ultrasonic radiation and/or heated to aid in agitation in some embodiments.

Above the substrate 112, a lens 120 is provided which may be, for example, a 2" 100 mm focal length fused silica lens. For the sake of a compact system, a reflective mirror 122 may be provided for directing light from a light source 124 onto the substrate. Light source 124 may be, for example, a Hg(Xe) light source manufactured by Oriel and having model no. 66024. A second lens 126 may be provided for the purpose of projecting a mask image onto the substrate in combination with lens 620. This form of lithography is referred to herein as projection printing. As will be apparent from this disclosure, proximity printing and the like may also be used according to some embodiments.

Light from the light source is permitted to reach only selected locations on the substrate as a result of mask 128. Mask 128 may be, for example, a glass slide having etched chrome thereon. The mask 128 in one embodiment is provided with a grid of transparent locations and opaque locations. Such masks may be manufactured by, for example, Photo Sciences, Inc. Light passes freely through the transparent regions of the mask, but is reflected from or absorbed by other regions. Therefore, only selected regions of the substrate are exposed to light.

As discussed above, light valves (LCD's) may be used as an alternative to conventional masks to selectively expose regions of the substrate. Alternatively, fiber optic faceplates such as those available from Schott Glass, Inc, may be used for the purpose of contrast enhancement of the mask or as the sole means of restricting the region to which light is applied. Such faceplates would be placed directly above or on the substrate in the reactor shown in FIG. 22A. In still further embodiments, flys-eye lenses, tapered fiber optic faceplates, or the like, may be used for contrast enhancement.

In order to provide for illumination of regions smaller than a wavelength of light, more elaborate techniques may be utilized. For example, according to one preferred embodiment, light is directed at the substrate by way of molecular microcrystals on the tip of, for example, micropipettes. Such devices are disclosed in Lieberman et al., "A Light Source Smaller Than the Optical Wavelength," Science (1990) 247:59-61, which is incorporated herein by reference for all purposes.

In operation, the substrate is placed on the cavity and sealed thereto. All operations in the process of preparing the substrate are carried out in a room lit primarily or entirely by light of a wavelength outside of the light range at which the protecting group is removed. For example, in the case of NVOC, the room should be lit with a conventional dark room light which provides little or no UV light. All operations are preferably conducted at about room temperature.

A first, deprotection fluid (without a monomer) is circulated through the cavity. The solution preferably is of 5 mM sulfuric acid in dioxane solution which serves to keep exposed amino groups protonated and decreases their reactivity with photolysis by-products. Absorptive materials such as N,N-diethylamino 2,4-dinitrobenzene, for example, may be included in the deprotection fluid which serves to absorb light and prevent reflection and unwanted photolysis.

The slide is, thereafter, positioned in a light ray path from the mask such that first locations on the substrate are illuminated and, therefore, deprotected. In preferred embodiments the substrate is illuminated for between about 1 and 15 minutes with a preferred illumination time of about 10 minutes at 10–20 mW/cm$^2$ with 365 nm light. The slides are neutralized (i.e., brought to a pH of about 7) after photolysis with, for example, a solution of diisopropylethylamine (DIEA) in methylene chloride for about 5 minutes.

The first monomer is then placed at the first locations on the substrate. After irradiation, the slide is removed, treated in bulk, and then reinstalled in the flow cell. Alternatively, a fluid containing the first monomer, preferably also protected by a protective group, is circulated through the cavity by way of pump 116aF. If, for example, it is desired to attach the amino acid Y to the substrate at the first locations, the amino acid Y (bearing a protecting group on its s-nitrogen), along with reagents used to render the monomer reactive, and/or a carrier, is circulated from a storage container 118aF, through the pump, through the cavity, and back to the inlet of the pump.

The monomer carrier solution is, in a preferred embodiment, formed by mixing of a first solution (referred to herein as solution "A") and a second solution (referred to herein as solution "B"). Table 3 provides an illustration of a mixture which may be used for solution A.

Table 3 Representative Monomer Carrier Solution "A"

0.25 mMoles NVOC amino protected amino acid
37 mg HOBT (1-Hydroxybenzotriazole)
250 μl DMF (Dimethylformamide)
86 μl DIEA (Diisopropylethylamine)

The composition of solution B is illustrated in Table 4. Solutions A and B are mixed and allowed to react at room temperature for about 8 minutes, then diluted with 2 ml of DMF, and 500 μl are applied to the surface of the slide or the solution is circulated through the reactor system and allowed to react for about 2 hours at room temperature. The slide is then washed with DMF, methylene chloride and ethanol.

Table 4 Representative Monomer Carrier Solution "B"

250 μl DMF 111 mg BOP (Benzotriazolyl-n-oxy-tris(dimethylamino) phosphoniumhexafluorophosphate)

As the solution containing the monomer to be attached is circulated through the cavity, the amino acid or other monomer will react at its carboxy terminus with amino groups on the regions of the substrate which have been deprotected. Of course, while the invention is illustrated by way of circulation of the monomer through the cavity, the invention could be practiced by way of removing the slide from the reactor and submersing it in an appropriate monomer solution.

After addition of the first monomer, the solution containing the first amino acid is then purged from the system. After circulation of a sufficient amount of the DMF/dichloromethane such that removal of the amino acid can be assured (e.g., about 50×times the volume of the cavity and carrier lines), the mask or substrate is repositioned, or a new mask is utilized such that second regions on the substrate will be exposed to light and the light 124 is engaged for a second exposure. This will deprotect second regions on the substrate and the process is repeated until the desired polymer sequences have been synthesized.

The entire derivatized substrate is then exposed to a receptor of interest, preferably labeled with, for example, a fluorescent marker, by circulation of a solution or suspension of the receptor through the cavity or by contacting the surface of the slide in bulk. The receptor will preferentially bind to certain regions of the substrate which contain complementary sequences.

Antibodies are typically suspended in what is commonly referred to as "supercocktail," which may be, for example, a solution of about 1% BSA (bovine serum albumin), 0.05% Tween 20 TM in PBS (phosphate buffered saline) buffer. The antibodies are diluted into the supercocktail buffer to a final concentration of, for example, about 0.1 to 4 $\mu$g/ml.

Figure 22B:
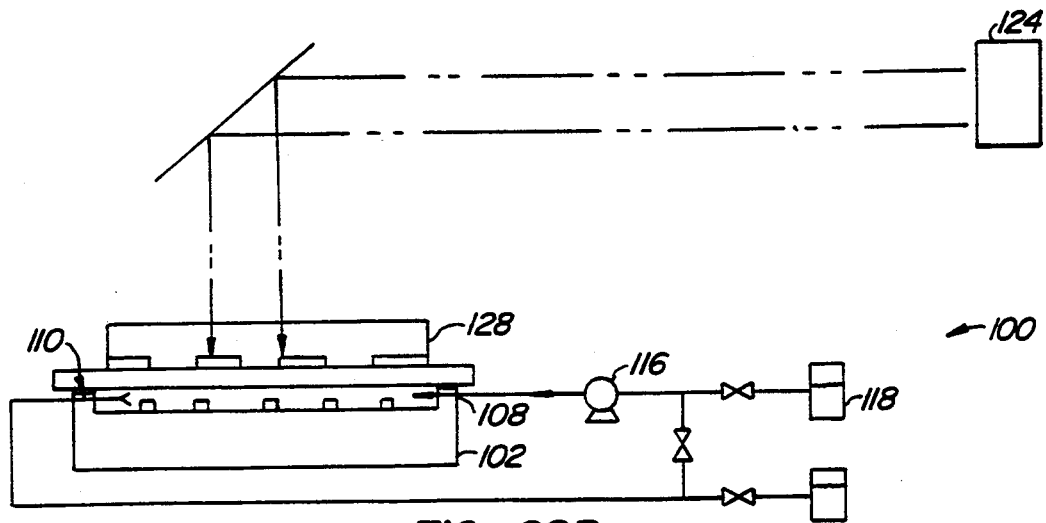

FIG. 22B illustrates an alternative preferred embodiment of the reactor shown in FIG. 22A. According to this embodiment, the mask 128 is placed directly in contact with the substrate. Preferably, the etched portion of the mask is placed face down so as to reduce the effects of light dispersion. According to this embodiment, the imaging lenses 120 and 126 are not necessary because the mask is brought into close proximity with the substrate.

Figure 23:
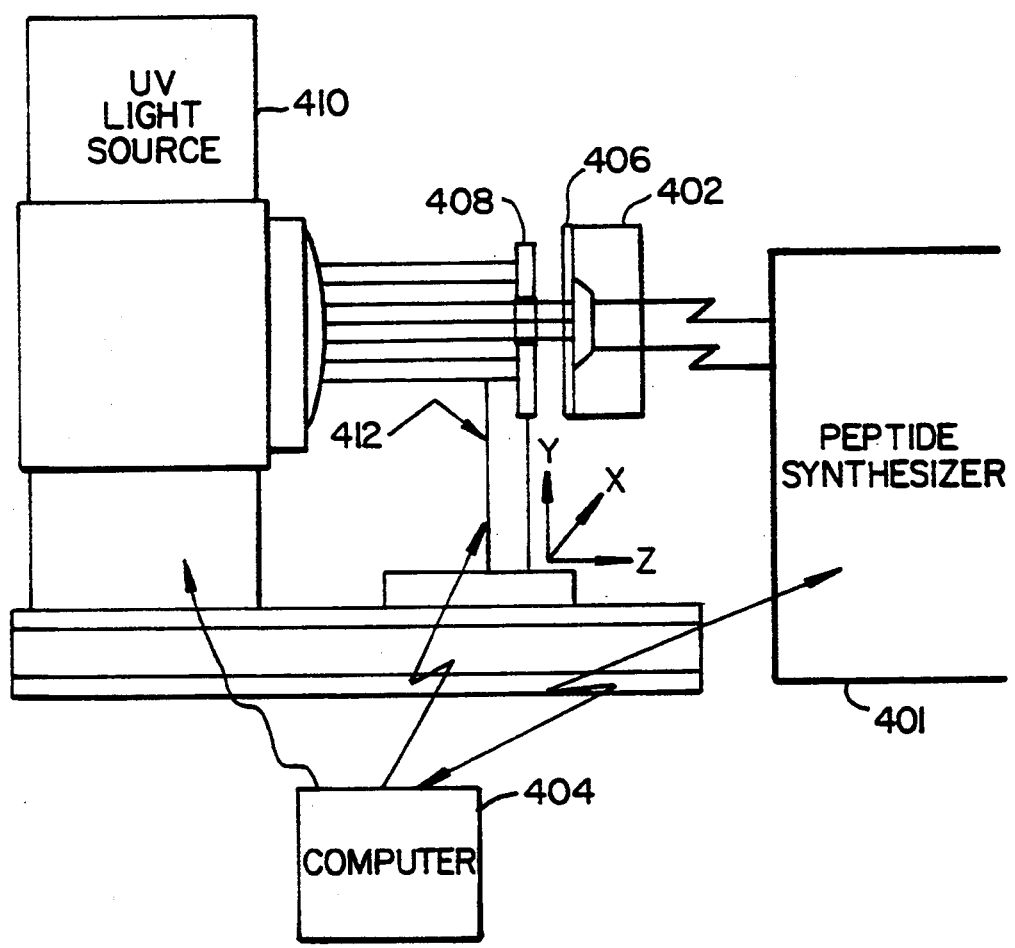
FIG. 23 schematically illustrates an automated system for synthesizing diverse polymer sequences.

FIG. 23 schematically illustrates a particularly preferred device used to synthesize diverse polymer sequences on a substrate. The device includes an automated peptide synthesizer 401. The automated peptide synthesizer is a device which flows selected reagents through a flow cell 402 under the direction of a computer 404. In a preferred embodiment the synthesizer is an ABI Peptide Synthesizer, model no. 431A. The computer may be selected from a wide variety of computers or discrete logic including for, example, an IBM PC-AT or similar computer linked with appropriate internal control systems in the peptide synthesizer. The PC is provided with signals from the ABI computer indicative of, for example, the beginning of a photolysis cycle. One can also modify the synthesizer with a board that links the contacts of relays in the computer in parallel with the switches to the keyboard of the control panel of the synthesizer to eliminate some of the-keystrokes that would otherwise be required to operate the synthesizer.

Substrate 406 is mounted on the flow cell, forming a cavity between the substrate and the flow cell. Selected reagents flow through this cavity from the peptide synthesizer at selected times, forming an array of peptides on the face of the substrate in the cavity. Mounted above the substrate, and preferably in contact with the substrate is a mask 408. Mask 408 is transparent in selected-regions to a selected wavelength of light and is opaque in other regions to the selected wavelength of light. The mask is illuminated with a light source 410 such as a UV light source. In one specific embodiment the light source 410 is a model no. 82420 made by Oriel. The mask is held and translated by an x-y translation stage 412 such as a translation stage made by Newport Corp. The computer coordinates action of the peptide synthesizer, translation stage, and light source. Of course, the invention may be used in some embodiments with translation of the substrate instead of the mask.

In operation, the substrate is mounted on the flow cell. The substrate, with its surface protected by a suitable photo removable protecting group, is exposed to light at selected locations by positioning the mask and directing light from a light source, through the mask, onto the substrate for a desired period of time (such as, for example, 1 sec to 60 min in the case of peptide synthesis). A selected peptide or other monomer/polymer is pumped through the reactor cavity by the peptide synthesizer for binding at the selected locations on the substrate. After a selected reaction time (such as about 1 sec to 300 min in the case of peptide reactions) the monomer is washed from the system, the mask is appropriately repositioned or replaced, and the cycle is repeated. In most embodiments of the invention, reactions may be conducted at or near ambient temperature. Agitation can be used to mix the reaction contents.

Figures 24A, 24B:
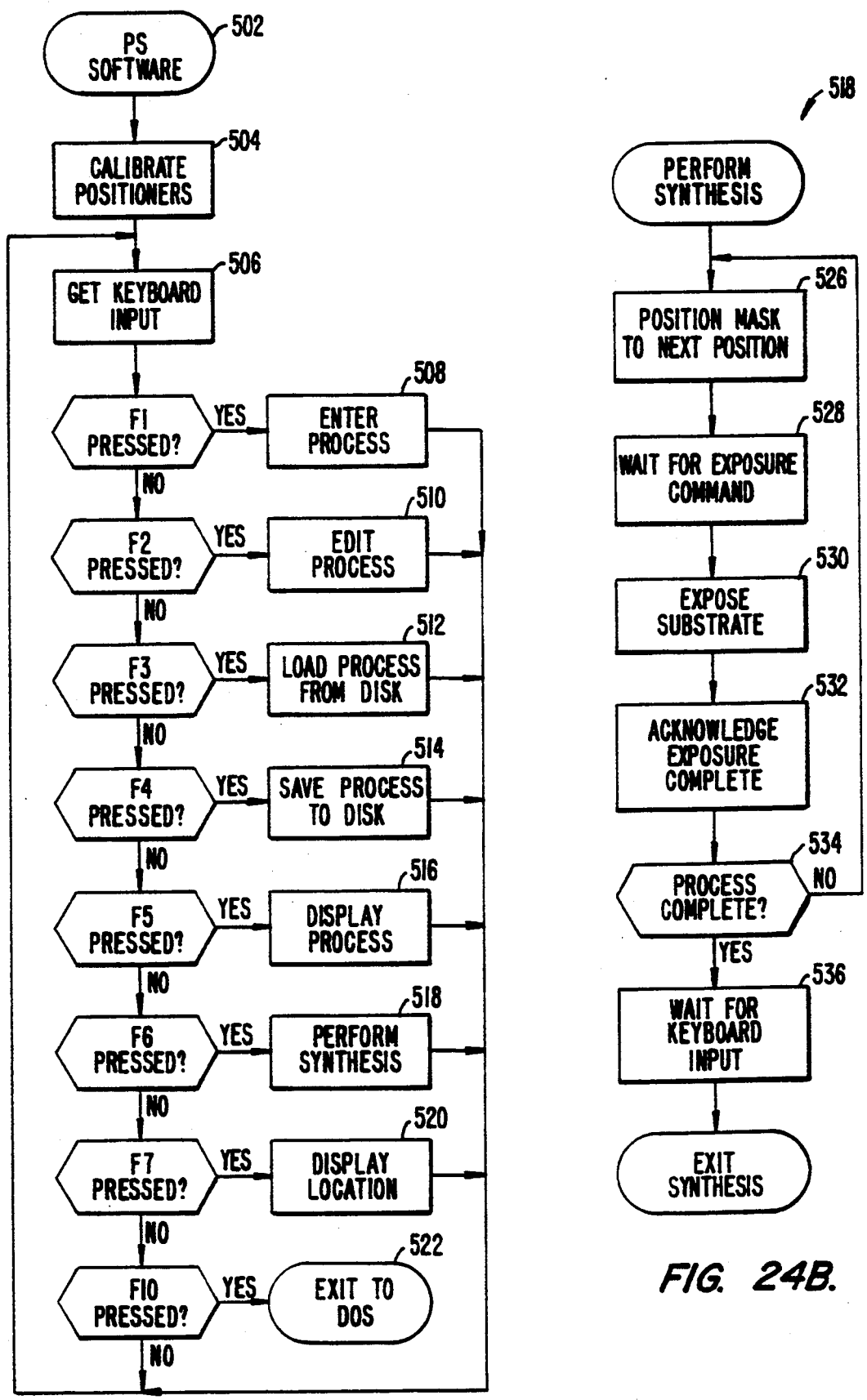
FIG. 24A and 24B illustrate operation of a program for polymer synthesis.

FIGS. 24A and 24B are flow charts of the software used in operation of the reactor system. At step 502 the peptide synthesis software (PS, attached as appendix 3) is initialized. At step 504 the system calibrates positioners on the x-y translation stage and begins a main loop. At step 506 the system determines which, if any, of the function keys on the computer have been pressed. If F1 has been pressed, the system prompts the user for input of a desired synthesis process. If the user enters F2, the system allows a user to edit a file for a synthesis process at step 510. If the user enters F3 the system loads a process from a disk at step 512. If the user enters F4 the system saves an entered or edited process to disk at step 514. If the user selects F5 the current process is displayed at step 516 while selection of F6 starts the main portion of the program, i.e., the actual synthesis according to the selected process. If the user selects F7 the system displays the location of the synthesized peptides, while pressing F10 returns the user to the disk operating system.

FIG. 4b illustrates the synthesis step 518 in greater detail. The main loop of the program is started in which the system first moves the mask to a next position at step 526. During the main loop of the program, necessary chemicals flow through the reaction cell under the direction of the on-board computer in the peptide synthesizer. At step 528 the system then waits for an exposure command and, upon receipt of the exposure command exposes the substrate for a desired time at step 530. When an acknowledgement of complete exposure is received at step 532 the system determines if the process is complete at step 534 and, if so, waits for additional keyboard input at step 536 and, thereafter, exits the perform synthesis process.

A computer program ("PS") used for operation of the system described above is written in Turbo C (Borland Int'l) and has been implemented in an IBM compatible system. The motor control software is adapted from software produced by Newport Corporation. It will be recognized that a large variety of programming languages could be utilized without departing from the scope of the invention herein. Certain calls are made to a graphics program in "Programmer Guide to PC and PS2 Video Systems" (Wilton, Microsoft Press, 1987), which is incorporated herein by reference for all purposes.

Alignment of the mask is achieved by one of two methods in preferred embodiments. In a first embodiment the system relies upon relative alignment of the various components, which is normally acceptable since x-y-z translation stages are capable of sufficient accuracy for the purposes herein. In alternative embodiments, alignment marks on-the substrate are coupled to a CCD device for appropriate alignment.

According to some embodiments, pure reagents are not added at each step, or complete photolysis of the protecting groups is not provided at each step. According to these embodiments, multiple products will be formed in each synthesis site. For example, if the monomers A and B are mixed during a synthesis step, A and B will bind to deprotected regions, roughly in proportion to their concentration in solution. Hence, a mixture of compounds will be formed in a synthesis region. A substrate formed with mixtures of compounds in various synthesis regions may be used to perform, for example, an initial screening of a large number of compounds, after which a smaller number of compounds in regions which exhibit high binding affinity are further screened. Similar results may be obtained by only partially photolyzing a region, adding a first monomer, re-photolyzing the same region, and exposing the region to a second monomer.

B. Combinatorial Synthesis Strategy

In preferred embodiments an ordered sequence of masks is utilized. In some embodiments it is possible to use as few as a single mask to synthesize all of the possible polymers of a given monomer set.

If, for example, it is desired to synthesize all 16 dinucleotides from four bases, a 1 cm square synthesis region is divided conceptually into 16 boxes, each 0.25 cm wide. Denote the four monomer units by A, B, C, and D. The first-reactions are carried out in four vertical columns, each 0.25 cm wide. The first mask exposes the left-most column of boxes, where A is coupled. The second mask exposes the next column, where B is coupled; followed by a third mask, for the C column; and a final mask that exposes the right-most column, for D. The first, second, third, and fourth masks may be a single "all-purpose" mask translated to different locations. Such an "all-purpose" mask can be useful in any synthesis strategy, whether binary or not.

The process is repeated in the horizontal direction for the second unit of the dimer. This time, the masks allow exposure of horizontal rows, again 0.25 cm wide. A, B, C, and D are sequentially coupled using masks that expose horizontal fourths of the reaction area. The resulting substrate contains all 16 dinucleotides of four bases.

The eight masks used to synthesize the dinucleotides or other dimers are related to one another by translation or rotation. In fact, one mask can be used in all eight steps if it is suitably rotated and translated. For example, in the example above, a mask with a single transparent region could be sequentially used to expose each of the vertical columns, translated 90°, and then sequentially used to allow exposure of the horizontal rows.

Tables 5 and 6 provide a simple computer program in Quick Basic for planning a masking program and a sample output, respectively, for the synthesis of a polymer chain of three monomers ("residues") having three different monomers in the first level, four different monomers in the second level, and five different monomers in the third level in a striped pattern. The output of the program is the number of cells, the number of "stripes" (light regions) on each mask, and the amount of translation required for each exposure of the mask.

TABLE 5

Mask Strategy Program

```
DEFINT A-Z
DIM b(20), w(20), l(500)
F$ = "LPT1:"
OPEN f$ FOR OUTPUT AS #1 jmax = 3            'Number of residues
b(1) = 3: b(2) = 4: b(3) = 5    'Number of building blocks
for res 1,2,3
g = 1: lmax(1) = 1

FOR j = 1 TO jmax: g= g * b(j): NEXT j
```

TABLE 5-continued

Mask Strategy Program

```
w(0) = 0: w(1) = g / b(1)

PRINT #1, "MASK2.BAS ", DATE$, TIME$: PRINT #1,
PRINT #1, USING "Number of residues=##"; jmax
FOR j = 1 TO jmax
PRINT #1, USING "    Residue ##    ## building blocks"; j; b(j)
NEXT j
PRINT #1, ""
PRINT #1, USING "Number of cells=####"; g: PRINT #1, FOR j = 2 TO jmax
lmax(j) = lmax(j − 1) * b(j − 1)
w(j) = w(j − 1) / b(j)
NEXT j FOR j = 1 TO jmax
PRINT #1, USING "Mask for residue ##"; j; PRINT #1,
PRINT #1, USING "    Number if stripes=###"; lmax(j)
PRINT #1, USING "    Width of each stripe=###"; w(j)
FOR l = 1 TO lmax(j)
a = 1 + (l − 1) * w(j − 1)
ae = a + w(j) − 1
PRINT #1, USING "    Stripe ## begins at location ### and
ends at ###"; l; a; ae
NEXT l
PRINT #1,
PRINT #1, USING "    For each of ## building blocks,
translate mask by ## cell(s)"; b(j); w(j),
PRINT #1, : PRINT #1, : PRINT #1,
NEXT j
```

© Copyright 1990, Affymax Technologies N.V.

TABLE 6

Masking Strategy Output

Number of residues= 3
    Residue 1    3 building blocks
    Residue 2    4 building blocks
    Residue 3    5 building blocks Number of cells= 60

Mask for residue 1

Number of sripes= 1
    Width of each stripe= 20
    Stripe  1 begins at location  1 and ends at 20

For each of 3 building blocks, translate mask by 20 cell(s)

Mask for residue 2

Number of stripes= 3
    Width of each stripe= 5
    Stripe  1 begins at location  1 and ends at  5
    Stripe  2 begins at location 21 and ends at 25
    Stripe  3 begins at location 41 and ends at 45

For each of 4 building blocks, translate mask by 5 cell(s)

Mask for residue 3

Number of stripes= 12
    Width of each stripe= 1
    Stripe  1 begins at location  1 and ends at  1
    Stripe  2 begins at location  6 and ends at  6
    Stripe  3 begins at location 11 and ends at 11
    Stripe  4 begins at location 16 and ends at 16
    Stripe  5 begins at location 21 and ends at 21
    Stripe  6 begins at location 26 and ends at 26
    Stripe  7 begins at location 31 and ends at 31
    Stripe  8 begins at location 36 and ends at 36
    Stripe  9 begins at location 41 and ends at 41
    Stripe 10 begins at location 46 and ends at 46
    Stripe 11 begins at location 51 and ends at 51
    Stripe 12 begins at location 56 and ends at 56

TABLE 6-continued

Masking Strategy Output

For each of 5 building blocks, translate mask by 1 cell(s)

© Copyright 1990, Affymax Technologies N.V.

In preferred embodiments of the invention herein a binary synthesis strategy is utilized. The binary synthesis strategy is illustrated herein primarily with regard to a masking strategy, although it will be applicable to other polymer synthesis strategies such as the pin strategy, and the like.

In a binary synthesis strategy, the substrate is irradiated with a first mask, exposed to a first building block, irradiated with a second mask, exposed to a second building block, etc. Each combination of masked irradiation and exposure to a building block is referred to herein as a "cycle."

In a preferred binary masking strategy, the masks for each cycle allow illumination of half of a region of interest on the substrate and no illumination of the remaining half of the region of interest. By "half" it is intended herein not to mean exactly one-half the region of interest, but instead a large fraction of the region of interest such as from about 30 to 70 percent of the region of interest. It will be understood that the entire masking strategy need not take a binary form; instead non-binary cycles may be introduced as desired between binary cycles.

In preferred embodiments of the binary masking strategy, a given cycle illuminates only about half of the region which was illuminated in a previous cycle, while not illuminating the remaining half of the illuminated portion from the previous cycle. Conversely, in such preferred embodiments, a given cycle illuminates half of the region which was not illuminated in the previous cycle and does not illuminate half the region which was not illuminated in a previous cycle.

The synthesis-strategy is most readily illustrated and handled in matrix notation. At each synthesis site, the determination of whether to add a given monomer is a binary process. Therefore, each product element $P_j$ in a product matrix P is given by the dot product of two vectors, a chemical reactant vector, (CRV) e.g., CRV=[A,B,C,D], and a binary vector $\sigma_j$. Inspection of the products in the example below for a four-step synthesis, shows that in one four-step synthesis $\sigma_1=[1,0,1,0]$, $\sigma_2=[1,0,0,1]$, $\sigma_3=[0,1,1,0]$, and $\sigma_4=[0,1,0,1]$, where a 1 indicates illumination and a 0 indicates no illumination. Therefore, it becomes possible to build a "switch matrix" S from the column vectors $\sigma_j$ (j=1,k where k is the number of products).

$$S = \begin{array}{cccc} \sigma_1 & \sigma_2 & \sigma_3 & \sigma_4 \\ 1 & 1 & 0 & 0 \\ 0 & 0 & 1 & 1 \\ 1 & 0 & 1 & 0 \\ 0 & 1 & 0 & 1 \end{array}$$

The outcome P of a synthesis is simply P=CS, the product of the chemical reactant matrix and the switch matrix.

The switch matrix for an n-cycle synthesis yielding k products has n rows and k columns. An important attribute of S is that each row specifies a mask. A two-dimensional mask $m_j$ for the jth chemical step of a synthesis is obtained directly from the jth row of S by placing the elements $s_{j1}, \ldots s_{jk}$ into, for example, a square format. The particular arrangement below provides a square format, although linear or other arrangements may be utilized.

$$S = \begin{array}{cccc} s_{11} & s_{12} & s_{13} & s_{14} \\ s_{21} & s_{22} & s_{23} & s_{24} \\ s_{31} & s_{32} & s_{33} & s_{34} \\ s_{41} & s_{42} & s_{43} & s_{44} \end{array} \qquad m_j = \begin{array}{cc} s_{j1} & s_{j2} \\ s_{j3} & s_{j4} \end{array}$$

Of course, compounds formed in a lightactivated synthesis can be positioned in any defined geometric array. A square or rectangular matrix is convenient but not required. The rows of the switch matrix may be transformed into any convenient array as long as equivalent transformations are used for each row.

For example, the masks in the four-step synthesis below are then denoted by:

$$m_1 = \begin{array}{cc}1 & 1\\0 & 0\end{array} \quad m_2 = \begin{array}{cc}0 & 0\\1 & 1\end{array} \quad m_3 = \begin{array}{cc}1 & 0\\1 & 0\end{array} \quad m_4 = \begin{array}{cc}0 & 1\\0 & 1\end{array}$$

where 1 denotes illumination (activation) and 0 denotes no illumination.

The matrix representation is used to generate a desired set of products and product maps in preferred embodiments. Each compound is defined by the product of the chemical vector and a particular switch vector. Therefore, for each synthesis address, one simply saves the switch vector, assembles all of them into a switch matrix, and extracts each of the rows to form the masks.

In some cases, particular product distributions or a maximal number of products are desired. For example, for CRV=[A,B,C,D], any switch vector ($\sigma_j$) consists of four bits. Sixteen four-bit vectors exist. Hence, a maximum of 16 different products can be made by sequential addition of the reagents [A,B,C,D]. These 16 column vectors can be assembled in 16! different ways to form a switch matrix. The order of the column vectors defines the masking patterns, and therefore, the spatial ordering of products but not their makeup. One ordering of these columns gives the following switch matrix (in which "null" ($\phi$) additions are included in brackets for the sake of completeness, although such null additions are elsewhere ignored herein):

```
    σ1                                            σ16  CRV
     1  1  1  1  1  1  1  1  0  0  0  0  0  0  0  0    A
    [0  0  0  0  0  0  0  0  1  1  1  1  1  1  1  1]   φ
S =  1  1  1  1  0  0  0  0  1  1  1  1  0  0  0  0    B
    [0  0  0  0  1  1  1  1  0  0  0  0  1  1  1  1]   φ
     1  1  0  0  1  1  0  0  1  1  0  0  1  1  0  0    C
    [0  0  1  1  0  0  1  1  0  0  1  1  0  0  1  1]   φ
     1  0  1  0  1  0  1  0  1  0  1  0  1  0  1  0    D
    [0  1  0  1  0  1  0  1  0  1  0  1  0  1  0  1]   φ
```

The columns of S according to this aspect of the invention are the binary representations of the numbers 15 to 0. The sixteen products of this binary synthesis are ABCD, ABC, ABD, AB, ACD, AC, AD, A, BCD, BC, BD, B, CD, C, D, and φ (null). Also note that each of the switch vectors from the four-step synthesis masks above (and hence the synthesis products) are present in the four bit binary switch matrix. (See columns 6, 7, 10, and 11). Note that if the desired compounds comprise only dimers, then one could extract the switch vectors for compounds AB, AC, AD, BC, BD, and CD for this synthesis.

This synthesis procedure provides an easy way for mapping the completed products. The products in the various locations on the substrate are simply defined by the columns of the switch matrix (the first column indicating, for example, that the product ABCD will be present in the upper left-hand location of the substrate). Furthermore, if only selected desired products are to be made, the mask sequence can be derived by extracting the columns with the desired sequences. For example, to form the product set ABCD, ABD, ACD, AD, BCD, BD, CD, and D, the masks are formed by use of a switch matrix with only the 1st, 3rd, 5th, 7th, 9th, 11th, 13th, and 15th columns arranged into the switch matrix:

$$S = \begin{matrix} 1 & 1 & 1 & 1 & 0 & 0 & 0 & 0 \\ 1 & 1 & 0 & 0 & 1 & 1 & 0 & 0 \\ 1 & 0 & 1 & 0 & 1 & 0 & 1 & 0 \\ 1 & 1 & 1 & 1 & 1 & 1 & 1 & 1 \end{matrix}$$

To form all of the polymers of length 4, the reactant matrix [ABCDABCDABCDABCD] is used. The switch matrix will be formed from a matrix of the binary numbers from 0 to $2^{16}$ arranged in columns. The columns having four monomers are then selected and arranged into a switch matrix. Therefore, it is seen that the binary switch matrix in general will provide a representation of all the products which can be made from an n-step synthesis, from which the desired products are then extracted.

The rows of the binary switch matrix will, in preferred embodiments, have the property that each masking step illuminates half of the synthesis area. Each masking step also factors the preceding masking step; that is, half of the region that was illuminated in the preceding step is again illuminated, whereas the other half is not. Half of the region that was not illuminated in the preceding step is also illuminated, whereas the other half is not. Thus, masking is recursive. The masks are constructed, as described previously, by extracting the elements of each row and placing them in a square array. For example, the four masks in S for a four-step synthesis are:

$$m_1 = \begin{matrix}1&1&1&1\\1&1&1&1\\0&0&0&0\\0&0&0&0\end{matrix} \quad m_2 = \begin{matrix}1&1&1&1\\0&0&0&0\\1&1&1&1\\0&0&0&0\end{matrix} \quad m_3 = \begin{matrix}1&1&0&0\\1&1&0&0\\1&1&0&0\\1&1&0&0\end{matrix} \quad m_4 = \begin{matrix}1&0&1&0\\1&0&1&0\\1&0&1&0\\1&0&1&0\end{matrix}$$

The recursive factoring of masks allows the products of a light-directed synthesis to be represented by a polynomial. (Some light activated syntheses can only be denoted by irreducible, i.e., prime polynomials.) For example, the polynomial corresponding to the top synthesis of FIG. 8a (discussed below) is $$P=(A+S)(C+D)$$

A reaction polynomial may be expanded as though it were an algebraic expression, provided that the order of joining of reactants $X_1$ and $X_2$ is preserved ($X_1X_2 \neq X_2X_1$), i.e., the products are not commutative. The product then is AC+AD+BC+BD. The polynomial explicitly specifies the reactants and implicitly specifies the mask for each step. Each pair of parentheses demarcates a round of synthesis. The chemical reactants of a round (e.g., A and B) react at nonoverlapping sites and hence cannot combine with one another. The synthesis area is divided equally among the elements of a round (e.g., A is directed to one-half of the area and B to the other half). Hence, the masks for a round (e.g., the masks $m_A$ and $m_B$) are orthogonal and form an orthonormal set. The polynomial notation also signifies that each element in a round is to be joined to each element of the next round (e.g., A with C, A with D, B with C, and B with D). This is accomplished by having $m_c$ overlap $m_A$ and $m_B$ equally, and likewise for $m_D$. Because C and D are elements of a round, $m_C$ and $m_D$ are orthogonal to each other and form an orthonormal set.

The polynomial representation of the binary synthesis described above, in which 16 products are made from 4 reactants, is $$P=(A+\phi)(B+\phi)(C+\phi)(D+\phi)$$

which gives ABCD, ABC, ABD, AB, ACD, AC, AD, A, BCD, BC, BD, B, CD, C, D, and $\phi$ when expanded (with the rule that $\phi X=X$ and $X\phi=X$, and remembering that joining is ordered). In a binary synthesis, each round contains one reactant and one null (denoted by $\phi$). Half of the synthesis area receives the reactant and the other half receives nothing. Each mask overlaps every other mask equally.

Binary rounds and non-binary rounds can be interspersed as desired, as in $$P=(A+\phi)(B)(C+D+\phi)(E+F+G)$$

The 18 compounds formed are ABCE, ABCF, ABCG, ABDE, ABDF, ABDG, ABE, ABF, ABG, BCE, BCF, BCG, BDE, BDF, BDG, BE, BF, and BG. The switch matrix S for this 7-step synthesis is $$S = \begin{matrix} 1&1&1&1&1&1&1&1&1&0&0&0&0&0&0&0&0&0 \\ 1&1&1&1&1&1&1&1&1&1&1&1&1&1&1&1&1&1 \\ 1&1&1&0&0&0&0&0&0&1&1&1&0&0&0&0&0&0 \\ 0&0&0&1&1&1&0&0&0&0&0&0&1&1&1&0&0&0 \\ 1&0&0&1&0&0&1&0&0&1&0&0&1&0&0&1&0&0 \\ 0&1&0&0&1&0&0&1&0&0&1&0&0&1&0&0&1&0 \\ 0&0&1&0&0&1&0&0&1&0&0&1&0&0&1&0&0&1 \end{matrix}$$

The round denoted by (B) places B in all products because the reaction area was uniformly activated (the mask for B consisted entirely of 1's).

The number of compounds k formed in a synthesis consisting of r rounds, in which the ith round has $b_i$ chemical reactants and $z_i$ nulls, is $$k=\Sigma(b_i+Z_i)$$

and the number of chemical steps n is $$n=\Sigma b_i$$

The number of compounds synthesized when b=a (the number of chemical building blocks) and z=0 in all rounds is $a^{n/a}$, compared with $2^n$ for a binary synthesis. For n=20 and a=5, 625 compounds (all tetramers) would be formed, compared with $1.049 \times 10^6$ compounds in a binary synthesis with the same number of chemical steps.

It should also be noted that rounds in a polynomial can be nested, as in $$(A+(B+\phi)(C+\phi))(D+\phi)$$

The products are AD, BCD, BD, CD, D, A, BC, B, C, and φ.

Binary syntheses are attractive for two reasons. First, they generate the maximal number of products ($2^n$) for a given number of chemical steps (n). For four reactants, 16 compounds are formed in the binary synthesis, whereas only 4 are made when each round has two reactants. A 10-step binary synthesis yields 1,024 compounds, and a 20-step synthesis yields 1,048,576. Second, products formed in a binary synthesis are a complete nested set with lengths ranging from 0 to n. All compounds that can be formed by deleting one or more units from the longest product (the n-mer) are present. Contained within the binary set are the smaller sets that would be formed from the same reactants using any other set of masks (e.g., AC, AD, BC, and BD formed in the synthesis shown in FIG. 5 are present in the set of 16 formed by the binary synthesis). In some cases, however, the experimentally achievable spatial resolution may not suffice to accommodate all the compounds that could be formed on a single substrate. Therefore, practical limitations may require one to select a particular subset of the possible switch vectors for a given synthesis.

1. Example

Figure 25:
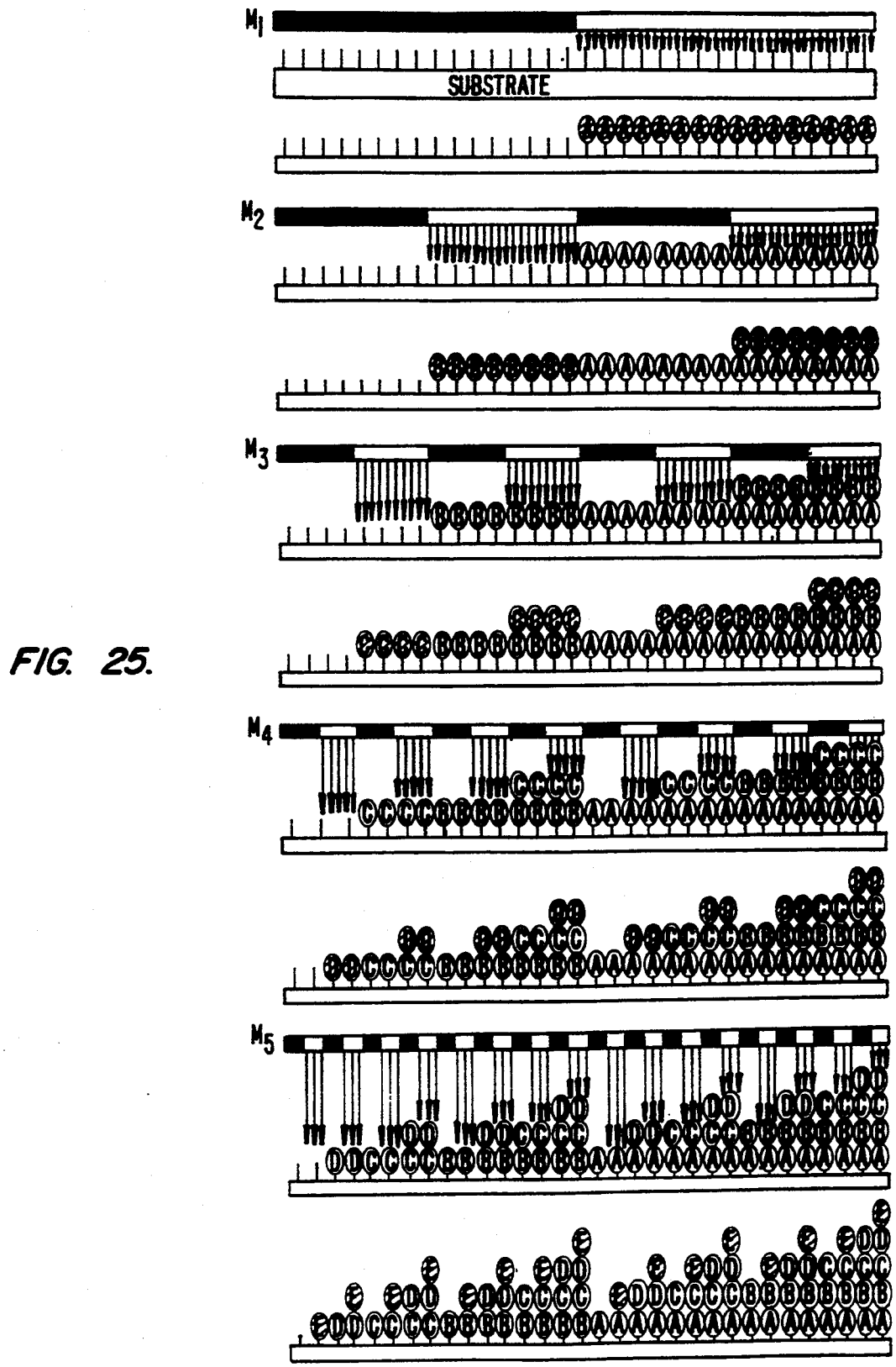
FIG. 25 is a schematic illustration of a "pure" binary masking strategy.

FIG. 25 illustrates a synthesis with a binary masking strategy. The binary masking strategy provides the greatest number of sequences for a given number of cycles. According to this embodiment, a mask $m_1$ allows illumination of half of the substrate. The substrate is then exposed to the building block A, which binds at the illuminated regions.

Thereafter, the mask $m_2$ allows illumination of half of the previously illuminated region, while it does not illuminate half of the previously illuminated region. The building block B is then added, which binds at the illuminated regions from $m_2$.

The process continues with masks $m_3$, $m_4$, and $m_5$, resulting in the product array shown in the bottom portion of the figure. The process generates 32 (2 raised to the power of the number of monomers) sequences with 5 (the number of monomers) cycles.

2. Example

Figure 26:
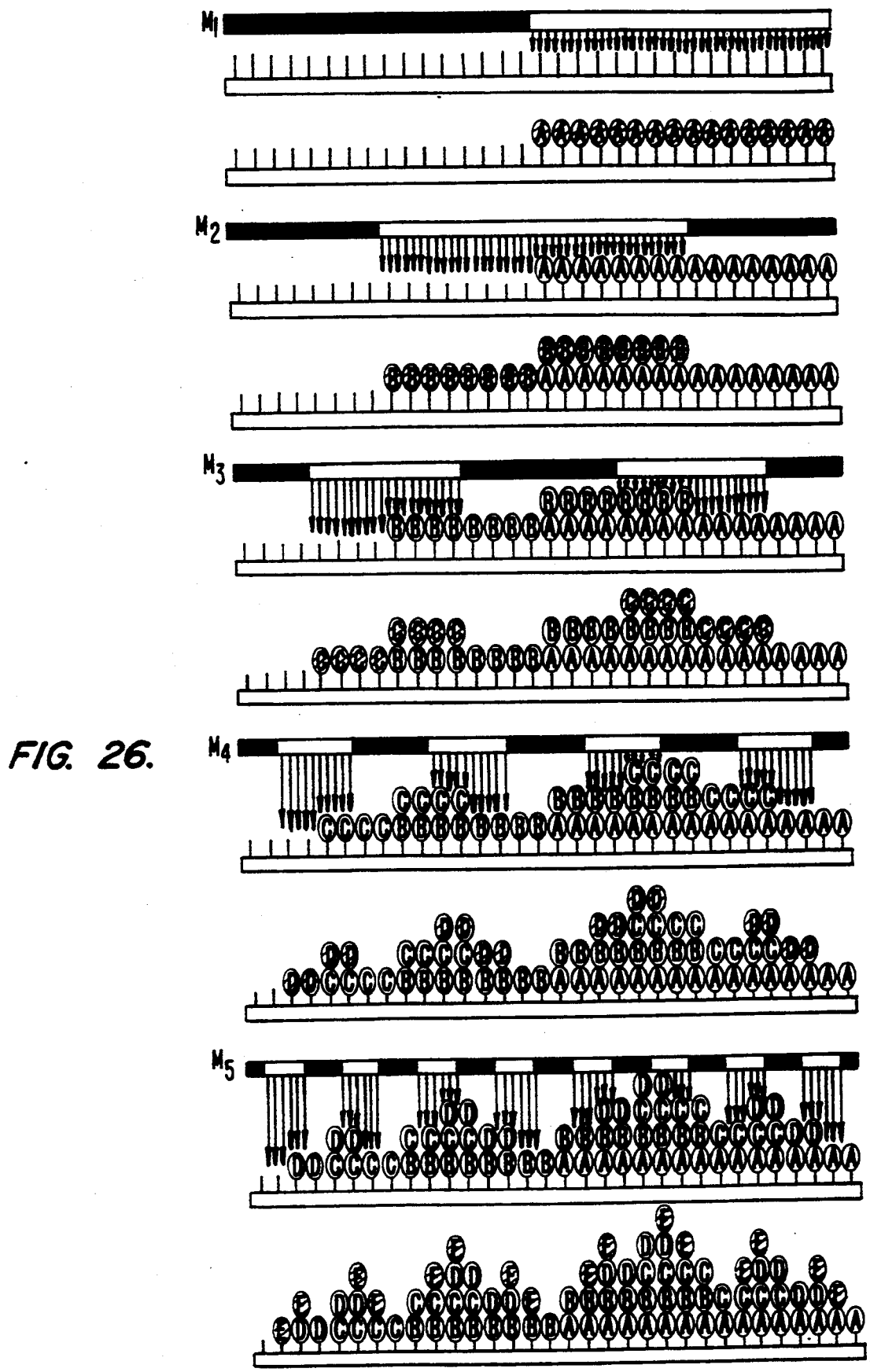
FIG. 26 is a schematic illustration of a gray code binary masking strategy.

FIG. 26 illustrates another preferred binary masking strategy which is referred to herein as the gray code masking strategy. According to this embodiment, the masks $m_1$ to $m_5$ are selected such that a side of any given synthesis region is defined by the edge of only one mask. The site at which the sequence BCDE is formed, for example, has its right edge defined by $m_5$ and its left side formed by mask $m_4$ (and no other mask is aligned on the sides of this site). Accordingly, problems created by misalignment, diffusion of light under the mask and the like will be minimized.

3. Example

Figure 27:
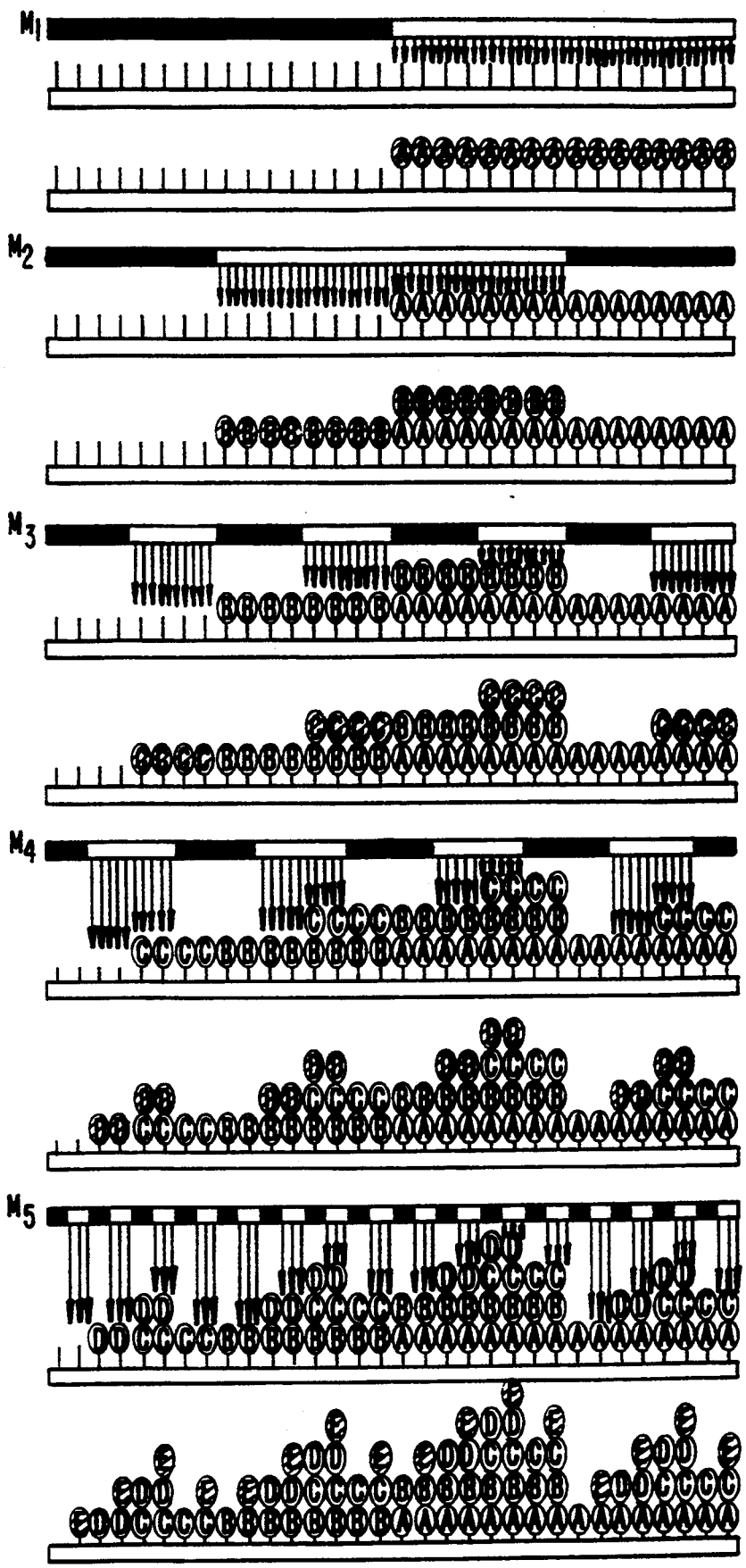
FIG. 27 is a schematic illustration of a modified gray code binary masking strategy.

FIG. 27 illustrates another binary masking strategy. According to this scheme, referred to herein as a modified gray code masking strategy, the number of masks needed is minimized. For example, the mask $m_2$ could be the same mask as $m_1$ and simply translated laterally. Similarly, the mask $m_4$ could be the same as mask $m_3$ and simply translated laterally.

4. Example

Figure 28A:
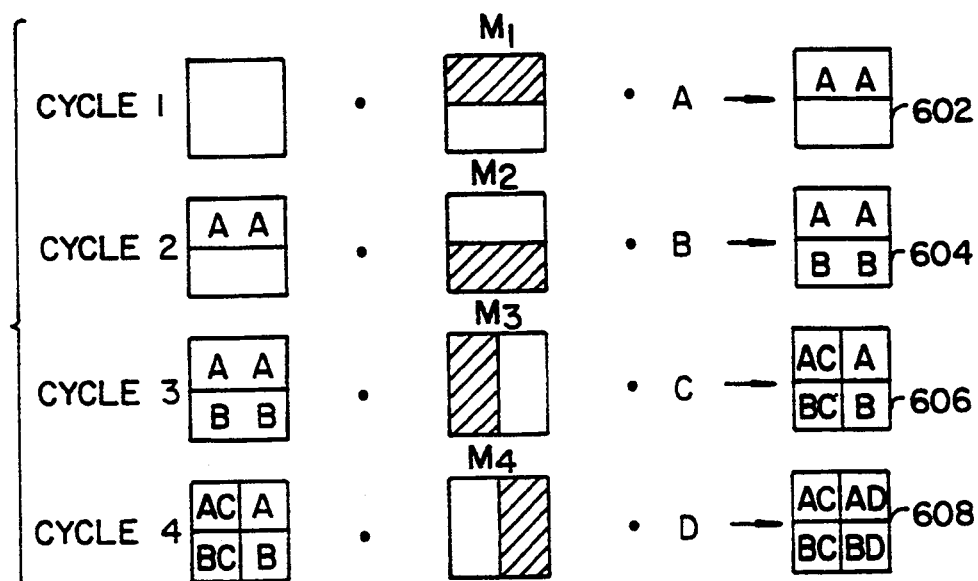
FIG. 28A schematically illustrates a masking strategy for a four step synthesis.

A four-step synthesis is shown in FIG. 28A. The reactants are the ordered set {A,B,C,D}. In the first cycle, illumination through $m_1$ activates the upper half of the synthesis area. Building block A is then added to give the distribution 602. Illumination through mask $m_2$ (which activates the lower half), followed by addition of B yields the next intermediate distribution 604. C is added after illumination through $m_3$ (which activates the left half) giving the distribution 604, and D after illumination through $m_4$ (which activates the right half), to yield the final product pattern 608 (AC,AD,BC,BD).

5. Example

Figure 28B:
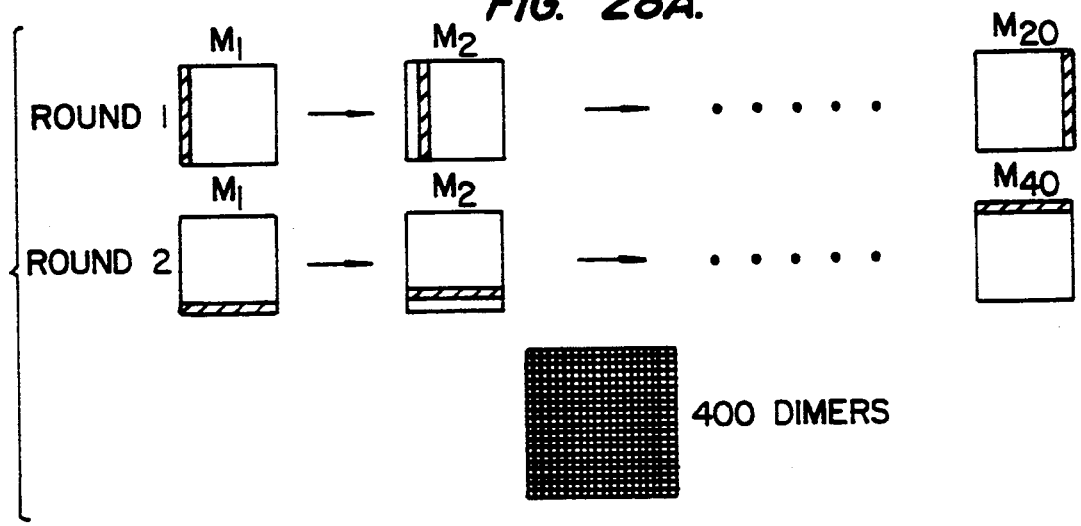
FIG. 28B schematically illustrates synthesis of peptide dimers of genetically coded amino acids.

The above masking strategy for the synthesis may be extended for all 400 dipeptides from the 20 naturally occurring amino acids as shown in FIG. 28B. The synthesis consists of two rounds, with 20 photolysis and chemical coupling cycles per round. In the first cycle of round 1, mask 1 activates 1/20th of the substrate for coupling with the first of 20 amino acids. Nineteen subsequent illumination/coupling cycles in round 1 yield a substrate consisting of 20 rectangular stripes each bearing a distinct member of the 20 amino acids. The masks of round 2 are perpendicular to round 1 masks and therefore a single illumination/coupling cycle in round 2 yields 20 dipeptides. The 20 illumination/coupling cycles of round 2 complete the synthesis of the 400 dipeptides.

6. Example

The power of the binary masking strategy can be appreciated by the outcome of a 10-step synthesis that produced 1,024 peptides. The polynomial expression for this 10-step binary synthesis was:

$$(f+\phi)(Y+\phi)(G+\phi)(A+\phi)(G+\phi)(T+\phi)$$
$$(F+\phi)(L+\phi)(S+\phi)(F+\phi)$$

Each peptide occupied a 400×400 μm square. A 32×32 peptide array (1,024 peptides, including the null peptide and 10 peptides of l=1, and a limited number of duplicates) was clearly evident in a fluorescence scan following side group deprotection and treatment with the antibody 3E7 and fluoresceinated antibody. Each synthesis site was a 400×400 μm square.

The scan showed a range of fluorescence intensities, from a background value of 3,300 counts to 22,400 counts in the brightest square (x=20, y=9). Only 15 compounds exhibited an intensity greater than 12,300 counts. The median value of the array was 4,800 counts.

Figure 29:
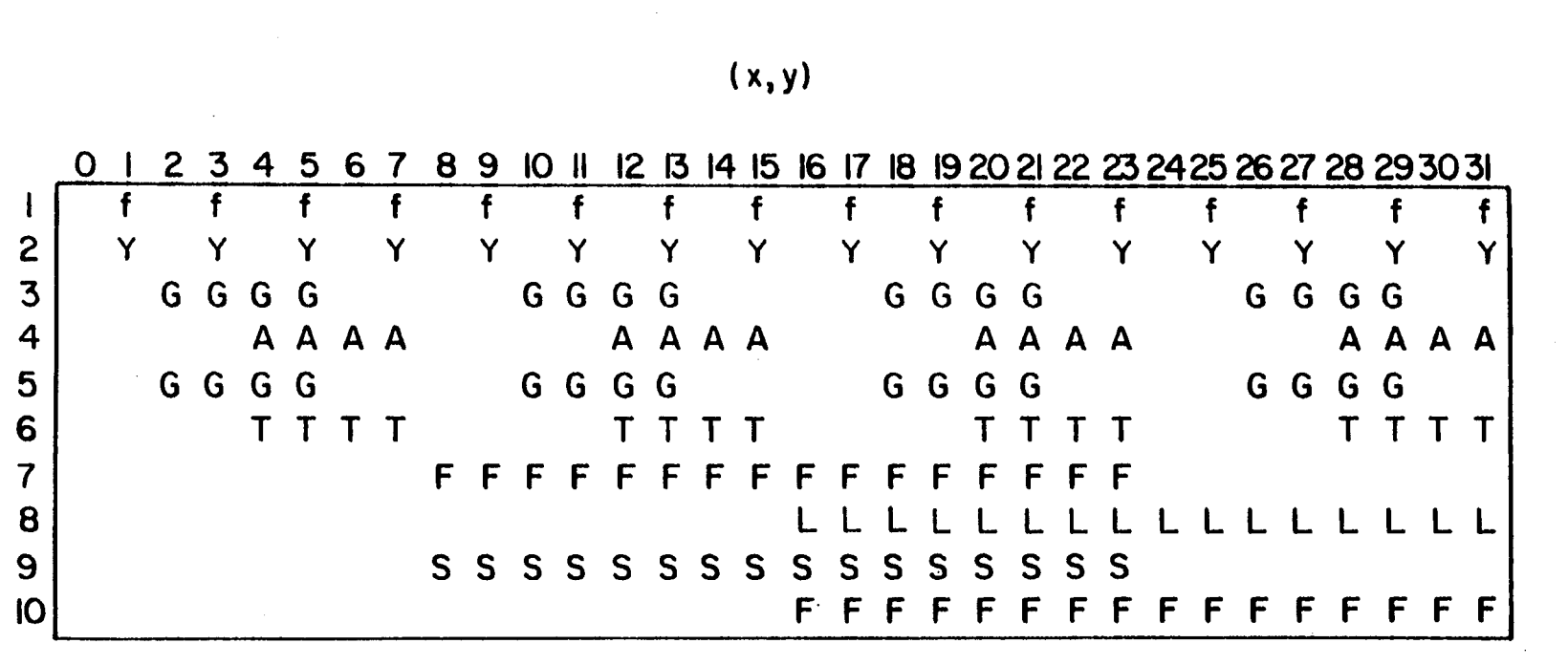

The identity of each peptide in the array could be determined from its x and y coordinates (each range from 0 to 31) and the map of FIG. 29. The chemical units at positions 2, 5, 6, 9, and 10 are specified by the y coordinate and those at positions 1, 3, 4, 7, 8 by the x coordinate. All but one of the peptides was shorter than 10 residues. For example, the peptide at x=12 and y=3 is YGAGF (SEQ ID NO:30; positions 1, 6, 8, 9, and 10 are nulls). YGAFLS (SEQ ID NO:4), the brightest element of the array, is at x=20 and y=9.

It is often desirable to deduce a binding affinity of a given peptide from the measured fluorescence intensity. Conceptually, the simplest case is one in which a single peptide binds to a univalent antibody molecule. The fluorescence scan is carried out after the slide is washed with buffer for a defined time. The order of fluorescence intensities is then a measure primarily of the relative dissociation rates of the antibody-peptide complexes. If the on-rate constants are the same (e.g., if they are diffusion-controlled), the order of fluorescence intensities will typically correspond to the order of binding affinities, However, the situation is sometimes more complex because a bivalent primary antibody and a bivalent secondary antibody are used. The density of peptides in a synthesis area corresponded to a mean separation of ~7 nm, which would allow multivalent antibody-peptide interactions. Hence, fluorescence intensities obtained according to the method herein will often be a qualitative indicator of binding affinity. For a more complete analysis of how the present invention can be extended to the binding affinity of an immobilized ligand to a receptor, see U.S. Ser. No. 796,947 filed Nov. 22, 1991 and incorporated by reference U.S. Pat. No. 5,324,633.

Another important consideration is the fidelity of synthesis. Deletions are produced by incomplete photodeprotection or incomplete coupling. The coupling yield per cycle in these experiments is typically between 85% and 95%. The contribution to the net coupling yield from photodeprotection and chemical coupling has been assessed in the following ways. The photolysis rate for NVOC-amino acids was experimentally determined and illumination conditions that ensure greater than 99% of the amino acids have been photodeprotected were chosen. The chemical coupling efficiency of selected amino acids on substrates employed in this invention has also been determined. For example, in order to determine the coupling efficiency of Leu to Leu, NVOC was first selectively photolyzed from one region of a NVOC-Leu derivitized surface. The photochemically deprotected amino groups in this region were then coupled to a FMOC-Leu-OBt. At this stage, incomplete Leu to Leu coupling would leave unreacted amino groups. A second photolysis step was then used to photolyze a different region of the substrate. Treatment of the substrate with FITC would label the free amino groups that remain from incomplete chemical coupling in the first region and free amino groups exposed by photolysis in the second region. Direct comparison of the quantitative fluorescence signal from both regions indicates the extent of chemical coupling. If the chemical coupling yield is high, the ratio of the signals of the first to the second photolysis regions is low. This technique as an has been used in order to develop the experimental conditions that maximize chemical coupling.

Implementing the switch matrix by masking is imperfect because of light diffraction, internal reflection, and scattering. Consequently, stowaways (chemical units that should not be on board) arise by unintended illumination of regions that should be dark. A binary synthesis array contains many of the controls needed to assess the fidelity of a synthesis. For example, the fluorescence signal from a synthesis area nominally containing a tetrapeptide ABCD could come from a tripeptide deletion impurity such as ACD. Such an artifact would be ruled out by the finding that the fluorescence intensity of the ACD site is less than that of the ABCD site.

The fifteen most highly fluorescent peptides in the array obtained with the synthesis of 1,024 peptides described above, were YGAFLS (SEQ ID NO:4), YGAFS (SEQ ID NO:5), YGAFL ( SEQ ID NO:6), YGGFLS (SEQ ID NO:7), YGAF (SEQ ID NO:8), YGALS (SEQ ID NO:9), YGGFS (SEQ ID NO:10), YGAL (SEQ ID NO:11), YGAFLF (SEQ ID NO:12), YGAF (SEQ ID NO:8), YGAFF (SEQ ID NO:13), YGGLS (SEQ ID NO:14), YGGFL (SEQ ID NO:1 and SEQ ID NO:15), YGAFSF (SEQ ID NO:16), and YGAFLSF (SEQ ID NO:17). A striking feature is that all fifteen begin with YG, which agrees with previous work showing that an amino-terminal tyrosine is a key determinant of binding to 3E7. Residue 3 of this set is either A or G, and residue 4 is either F or L. The exclusion of S and T from these positions is clear cut. The finding that the preferred sequence is YG (A/G) (F/L) fits nicely with the outcome of a study in which a very large library of peptides on phage generated by recombinant DNA methods was screened for binding to antibody 3E7 (see Cwirla et al., Proc. Natl. Acad. Sci. USA, (1990) 87:6378, incorporated herein by reference). Additional binary syntheses based on leads from peptides on phage experiments show that YGAFMQ (SEQ ID NO:18), YGAFM (SEQ ID NO:19), and YGAFQ (SEQ ID NO:20) give stronger fluorescence signals than does YGGFM (SEQ ID NO:21), the immunogen used to obtain antibody 3E7.

Variations on the above masking strategy will be valuable in certain circumstances. For example, if a "kernel" sequence of interest consists of PQR separated from XYZ, the aim is to synthesize peptides in which these units are separated by a variable number of different residues. The kernel can be placed in each peptide by using a mask that has 1's everywhere. The polynomial representation of a suitable synthesis is:

$$(P)\ (Q)\ (R)\ (A+\phi)\ (B+\phi)\ (C+\phi)\ (D+\phi)\ (X)\ (Y)\ (Z)$$

Sixteen peptides will be formed, ranging in length from the 6-mer PQRXYZ to the 10-mer PQRABCDXYZ.

Several other masking strategies will also find value in selected circumstances. By using a particular mask more than once, two or more reactants will appear in the same set of products. For example, suppose that the mask for an 8-step synthesis is

```
A  11110000
B  00001111
C  11001100
D  00110011
E  10101010
F  01010101
G  11110000
H  00001111
```

The products are ACEG, ACFG, ADEG, ADFG, BCEH, BCFH, BDEH, and BDFH. A and G always appear in the same product, although not necessarily next to each other, because their additions were directed by the same mask, and likewise for B and H.

7. Example

The synthesis strategies shown above are useful in many different applications. To aid in applying the present invention to any desired synthesis, the following illustrative example is provided. Assume one wishes to synthesize polymers up to 4 monomers in length. A given polymer can be designated as $Y_1\ Y_2\ Y_3\ Y_4$. If the monomer set contains 20 members, then the set (5) can be represented as follows:

$$S = \{M_1, M_2, M_3, \ldots M_{20}\},$$

where, for example, $Y_1$ may be $M_1$, $Y_2$ may be $M_{16}$, etc. Then, if one desires to synthesize all polymers in which each-position is varied through the entire set of monomers, then the synthesis can be represented as Product of Synthesis=$SY_2Y_3Y_4 = Y_1SY_3Y_4 + Y_1Y_2SY_4 + Y_1Y_2Y_3S$.

In the above polynomial, there are four terms, and each term represents 20 different compounds. If one desires to synthesize all polymers in which two positions are varied through the entire set of monomers, then the synthesis can be represented as:

Product of Synthesis = $SSY_3Y_4$ +
$SY_2SY_4 + SY_2Y_3S$ +
$Y_1SSY_4 + Y_1SY_3S$ +
$Y_1Y_2SS$ In the above polynomial, there are six terms, and each term represents 400 compounds. If one desires to synthesize all polymers in which three positions are varied through the entire set of monomers, then the synthesis can be represented as:

Product of Synthesis=$SSSy_4 + SSY_3S = Sy_2SS + Y_1SSS$

In the above polynomial, there are four terms and each term represents 8,000 compounds. If one desires to synthesize all polymers in which four positions are varied through the entire set of monomers, then the synthesis can be represented as:

Product of Synthesis=SSSS In the above polynomial, there is one term, which represents 160,000 compounds.

By modeling the synthesis as a polynomial expression, one can more easily discern the appropriate masking strategy required to effect the synthesis.

8. Example

Figure 30:
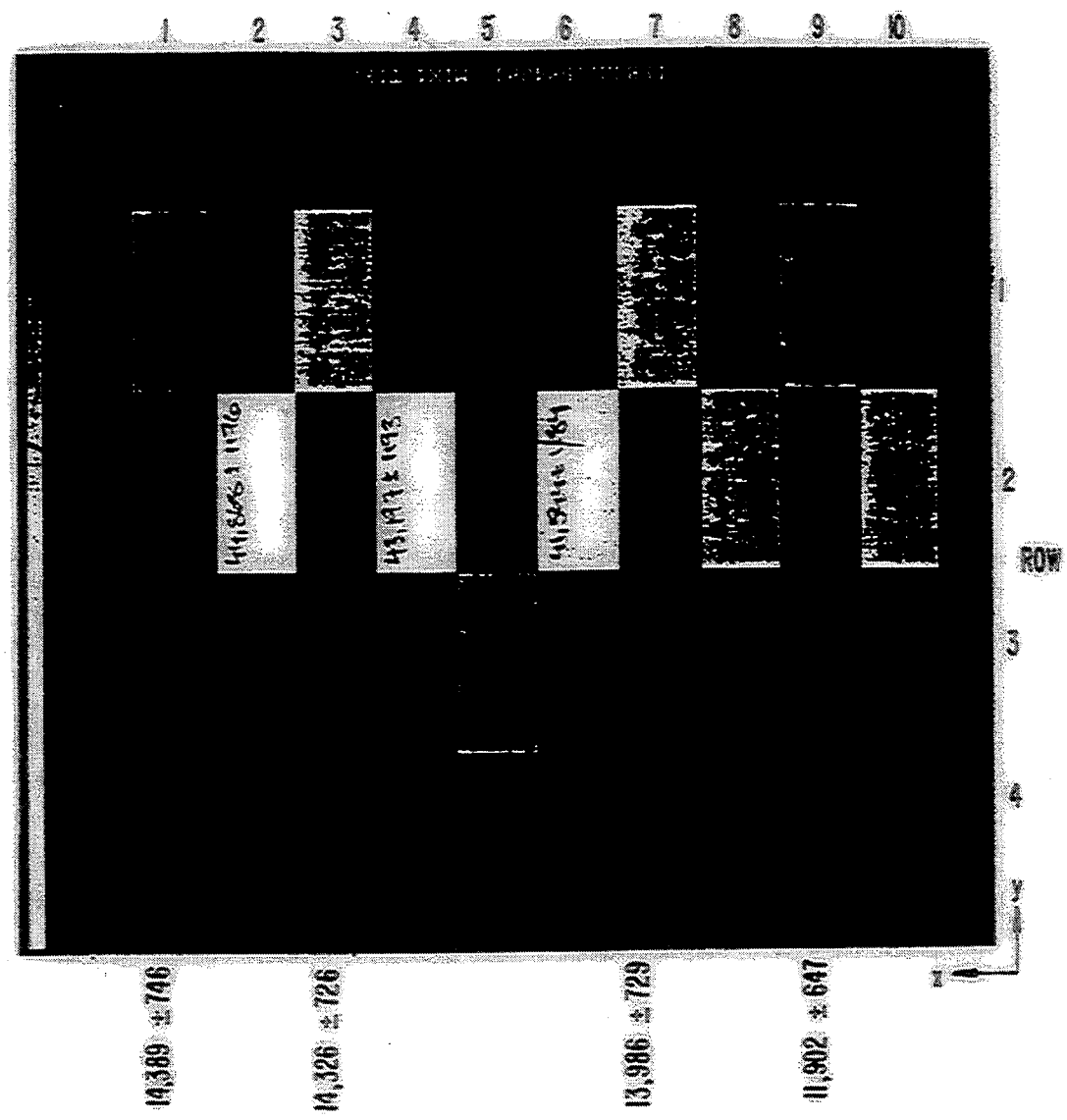
FIG. 30 is a fluorescence plot of a 4×10 array of peptides having sequences similar to dynorphin B.

One example of the power of this strategy involved the mapping of a binding epitope on dynorphin B. The sequence of this epitope was demonstrated (as shown below) to be RQFKVVT (SEQ ID NO:31). An array of peptides synthesized using the general protection-deprotection technology outlined above. Referring to FIG. 30, the following peptides were synthesized: row 1=RXFKVVT; row 2=RQXFKVVT; row 3=RQXKVVT; and row 4=RXKVVT. In each row, "X" represents a group of four amino acids, which were simultaneously added to the immobilized peptide. The particular group of amino acids used as "X" on a given block are identified by column number as follows: column 1 [G,A,R,K in a ratio 1:1:1:1], column 2 [null]; column 3 [C,M,S,T in the ratio 1:1:1:5]; column 4 [null]; column 5 [F,Y,W,H in the ratio 1:1:1:1]; column 6 [null]; column 7 [D,E,N,Q in the ratio 1:1:1:1]; column 8 [null]; column 9 [V,L,I,P in the ratio 2:1:4:1]; and column 10 [null].

After these peptides were synthesized, they were screened with an anti-dynorphin B murine monoclonal antibody and then exposed to a fluorescently labeled goat anti-mouse antibody. The brightest region (column 2, row 2) corresponds to the binding epitope, RQFKVVT. Other strongly labeled regions, include column 7, row 1 and column 5, row 3, each of which contains some peptides having the above binding epitope. It should be noted that the varying ratios of some of the amino acids within a given group were necessary to obtain roughly equal binding efficiencies among the four amino acids.

9. Example

A much larger array of compounds was prepared as shown in FIG. 31. In the first four steps, KVVT (SEQ ID NO:36) was synthesized over the entire substrate. Next, F was added over 50% of the substrate via a column mask as displayed in step 5. The next 20 steps involved addition of a row of each of the genetically-coded amino acids in a stepwise fashion down the substrate. One-twentieth of the substrate was exposed on each pass. Next, Q was added over one-half of the entire substrate as shown at step 26. Finally, R was added over the entire substrate.

Figure 32:
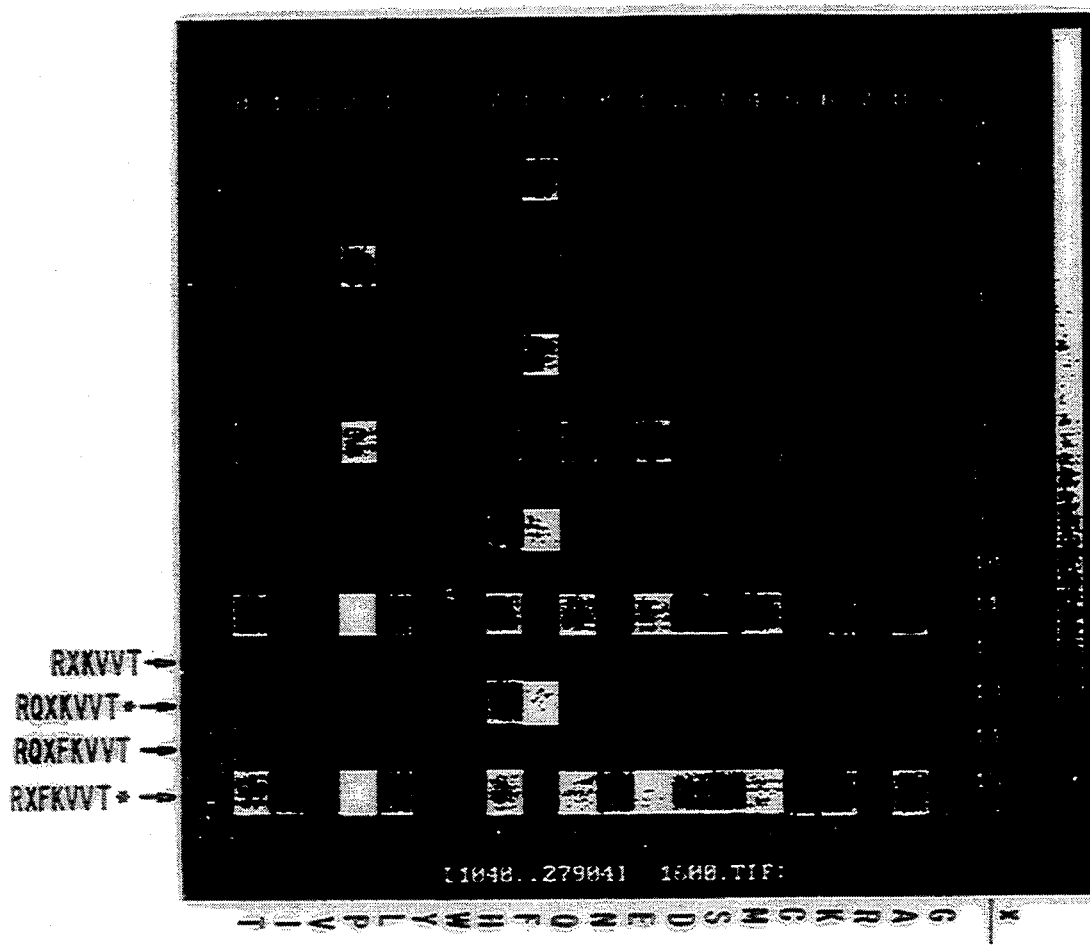
FIG. 32 is a fluorescence plot of an array of peptides produced according to the strategy illustrated in FIG. 31.

Four classes of peptide were produced: (1) RYKVVT (SEQ ID NO:32), (2) RQYKVVT (SEQ ID NO:33), (3) RQYFKVVT (SEQ ID NO:34), and (4) RYFKVVT (SEQ ID NO:35). In each case Y represents all 20 L-amino acids. FIG. 32 is an image of a fluorescence scan prepared after the final array of peptides was exposed to anti-dynorphin B mouse monoclonal antibody followed by goat anti-mouse antibody. The top one-fourth of the image was prepared according to the synthesis procedure outlined above.

10. Example

Figure 33:
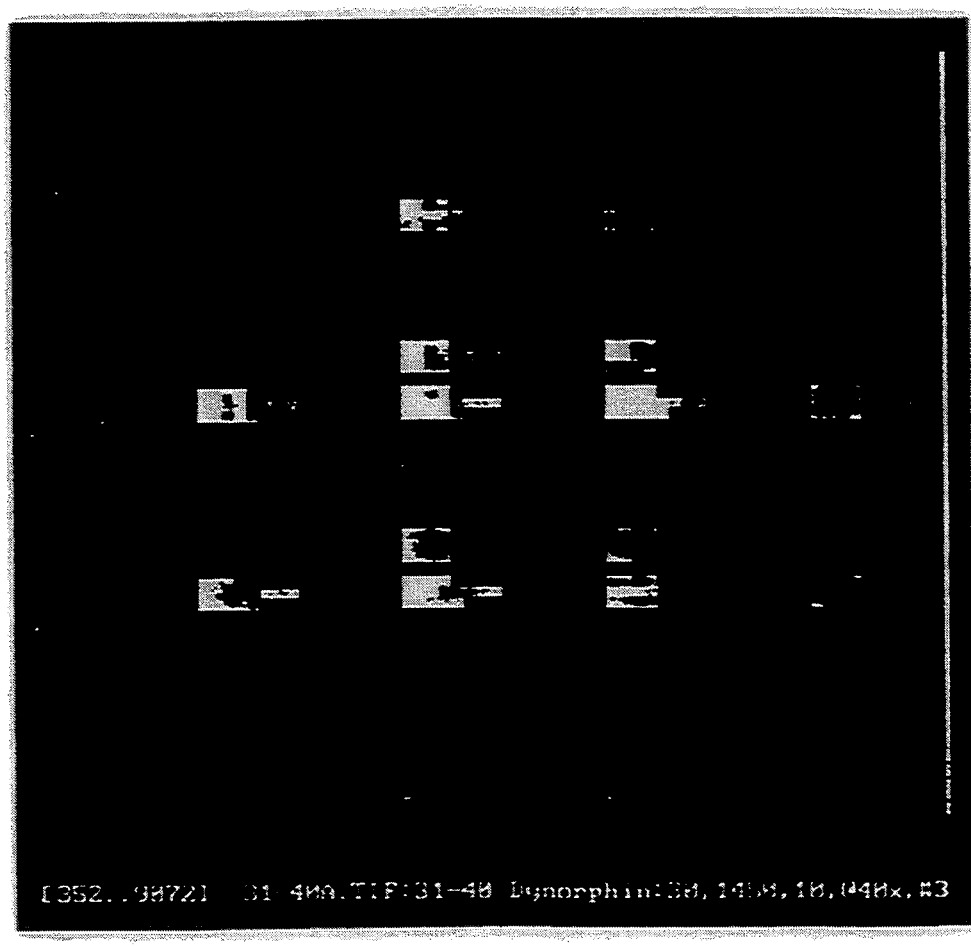
FIG. 33 is a fluorescence plot of an array of peptides containing various deletions from the dynorphin B sequence.

The binding epitope on dynorphin B for the anti-dynorphin B antibody described above was determined by deleting various amino acids and combinations of amino acids from the overall sequence of dynorphin B. The peptides containing these various deletions were prepared on a substrate by the general protection-deprotection methods described above. Then the substrate was exposed to the anti-dynorphin B monoclonal antibody and a fluorescence image was produced as shown in FIG. 33. Each quadrant of the image contained at least one site for each of the subject peptides (identified in Table 7).

From the intensity distribution contained in this plot, it was possible to determine the relative binding affinity to various of the peptides. This information is summarized in Table 7 below where N is the number of sites of which the peptide was synthesized.

TABLE 7

| SEQUENCE ADJUSTED | N | RELATIVE INTENSITY | |
|---|---|---|---|
| F | 8 | 4.9 ± 3.2 | |
| F L | 4 | 2.8 ± 2.2 | |
| F L R | 8 | 4.7 ± 2.1 | |
| F L R R | 4 | 6.0 ± 2.7 | |
| F L R R Q | 4 | 8.2 ± 2.6 | |
| F L R R Q F | 4 | 8.5 ± 3.4 | |
| F L R R Q F K | 4 | 10.2 ± 2.8 | |
| F L R R Q F K V | 8 | 13.7 ± 3.0 | |
| F L R R Q F K V V | 4 | 37.4 ± 14.6 | (30.5 ± 5.4) |
| F L R R Q F K V V T | 4 | 84.2 ± 28.2 | (98.3 ± 1.2) |
| L R R Q F K V V T | 4 | 86.9 ± 13.7 | |
| R R Q F K V V T | 4 | 98.8 ± 0.9 | |
| R Q F K V V T | 8 | 93.6 ± 10.0 | (96.2 ± 7.1) |
| Q F K V V T | 4 | 36.2 ± 16.0 | |
| F K V V T | 8 | 12.9 ± 3.7 | |
| K V V T | 4 | 10.7 ± 1.8 | |
| V V T | 4 | 8.2 ± 1.2 | |
| V T | 8 | 7.9 ± 3.0 | |
| T | 4 | 7.0 ± 3.9 | |

Figure 34:
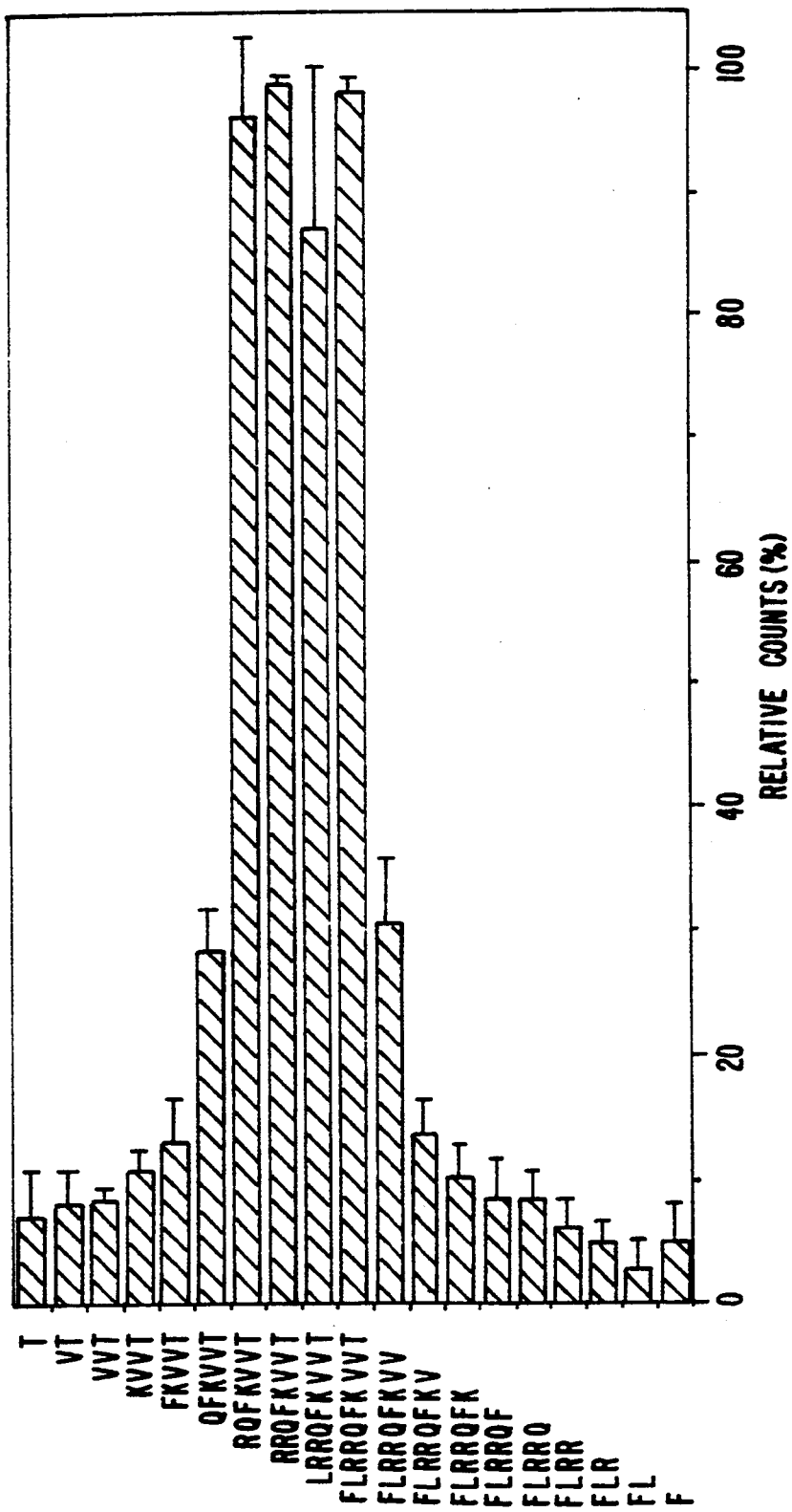
FIG. 34 is a plot of the relative binding affinities of an anti-dynorphin B monoclonal antibody to various sequences produced on the substrate shown in FIG. 33.

FIG. 34 is a bar graph showing the relative binding affinities for each of the peptides.

C. Linker selection

According to preferred embodiments the linker molecules used as an intermediary between the synthesized polymers and the substrate are selected for optimum length and/or type for improved binding interaction with a receptor. According to this aspect of the invention diverse linkers of varying length and/or type are synthesized for subsequent attachment of a ligand. Through variations in the length and type of linker, it becomes possible to optimize the binding interaction between an immobilized ligand and its receptor.

The degree of binding between a ligand (peptide, inhibitor, hapten, drug, etc.) and its receptor (enzyme, antibody, etc.) when one of the partners is immobilized onto a substrate will in some embodiments depend on the accessibility of the receptor in solution to the immobilized ligand. The accessibility in turn will depend on the length and/or type of linker molecule employed to immobilize one of the partners. Preferred embodiments of the invention therefore employ the VLSIPS TM synthesis technique described herein to generate an array of, preferably, inactive or inert linkers of varying length and/or type, using photochemical protecting groups to selectively expose different regions of the substrate and to build upon chemically-active groups.

In the simplest embodiment of this concept, the same unit is attached to the substrate in varying multiples or lengths in known locations on the substrate via VLSIPS TM synthesis techniques to generate an array of polymers of varying length. A single ligand (peptide, drug, hapten, etc.) is attached to each of them, and an assay is performed with the binding site to evaluate the degree of binding with a receptor that is known to bind to the ligand. In cases where the linker length impacts the ability of the receptor to bind to the ligand, varying levels of binding will be observed. In general, the linker which provides the highest binding will then be used to assay other ligands synthesized in accordance with the techniques herein.

According to other embodiments the binding between a single ligand/receptor pair is evaluated for linkers of diverse monomer sequence. According to these embodiments, the linkers are synthesized in an array in accordance with the techniques herein and have different monomer sequences (and, optionally, different lengths). Thereafter, all of the linker molecules are provided with a ligand known to have at least some binding affinity for a given receptor. The given receptor is then exposed to the ligand and binding affinity is deduced. Linker molecules which provide adequate binding between the ligand and receptor are then utilized in screening studies.

D. Protecting Groups

As discussed above, selectively removable protecting groups allow creation of well defined areas of substrate surface having differing reactivities. Preferably, the protecting groups are selectively removed from the surface by applying a specific activator, such as electromagnetic radiation of a specific wavelength and intensity. More preferably, the specific activator exposes selected areas of the surface to remove the protecting groups in the exposed areas.

Protecting groups of the present invention are used in conjunction with solid phase oligomer syntheses, such as peptide syntheses using natural or unnatural amino acids, nucleotide syntheses using deoxyribonucleic and ribonucleic acids, oligosaccharide syntheses, and the like. In addition to protecting the substrate surface from unwanted reaction, the protecting groups block a reactive end of the monomer to prevent self-polymerization. For instance, attachment of a protecting group to the amino terminus of an activated amino acid, such as an N-hydroxysuccinimide-activated ester of the amino acid, prevents the amino terminus of one monomer from reacting with the activated ester portion of another during peptide synthesis. Alternatively, the protecting group may be attached to the carboxyl group of an amino acid to prevent reaction at this site. Most protecting groups can be attached to either the amino or the carboxyl group of an amino acid, and the nature of the chemical synthesis will dictate which reactive group will require a protecting group. Analogously, attachment of a protecting group to the 5'-hydroxyl group of a nucleoside during synthesis using for example, phosphate-triester coupling chemistry, prevents the 5'-hydroxyl of one nucleoside from reacting with the 3'-activated phosphate-triester of another.

Regardless of the specific use, protecting groups are employed to protect a moiety on a molecule from reacting with another reagent. Protecting groups of the present invention have the following characteristics: they prevent selected reagents from modifying the group to which they are attached; they are stable (that is, they remain attached to the molecule) to the synthesis reaction conditions; they are removable under conditions that do not adversely affect the remaining structure; and once removed, they do not react appreciably with the surface or surface-bound oligomer. The selection of a suitable protecting group will depend, of course, on the chemical nature of the monomer unit and oligomer, as well as the specific reagents they are to protect against.

In a preferred embodiment, the protecting groups are photoactivatable. The properties and uses of photoreactive protecting compounds have been reviewed. See, McCray et al., *Ann. Rev. of Biophys. and Biophys. Chem.* (1989) 18:239–270, which is incorporated herein by reference. Preferably, the photosensitive protecting groups will be removable by radiation in the ultraviolet (UV) or visible portion of the electromagnetic spectrum. More preferably, the protecting groups will be removable by radiation in the near UV or visible portion of the spectrum. In some embodiments, however, activation may be performed by other methods such as localized heating, electron beam lithography, laser pumping, oxidation or reduction with microelectrodes, and the like. Sulfonyl compounds are suitable reactive groups for electron beam lithography. Oxidative or reductive removal is accomplished by exposure of the protecting group to an electric current source, preferably using microelectrodes directed to the predefined regions of the surface which are desired for activation. Other methods may be used in light of this disclosure.

Many, although not all, of the photoremovable protecting groups will be aromatic compounds that absorb near-UV and visible radiation. Suitable photoremovable protecting groups are described in, for example, McCray et al., Patchornik, *J. Amer. Chem. Soc.* (1970) 92:6333, and Amit et al., *J. Org. Chem.* (1974) 39:192, which are incorporated herein by reference.

A preferred class of photoremovable protecting groups has the general formula:

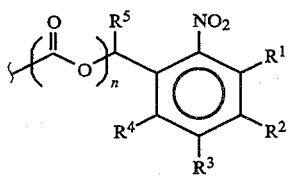

where $R^1$, $R^2$, $R^3$, and $R^4$ independently are a hydrogen atom, a lower alkyl, aryl, benzyl, halogen, hydroxyl, alkoxyl, thiol, thioether, amino, nitro, carboxyl, formate, formamido or phosphido group, or adjacent substituents (i.e., $R^1$-$R^2$, $R^2$-$R^3$, $R^3$-$R^4$) are substituted oxygen groups that together form a cyclic acetal or ketal; $R^5$ is a hydrogen atom, a alkoxyl, alkyl, halo, aryl, or alkenyl group, and n=0 or 1.

A preferred protecting group, 6-nitroveratryl (NV), which is used for protecting the carboxyl terminus of an amino acid or the hydroxyl group of a nucleotide, sugar, or carbohydrate for example, is formed when $R^2$ and $R^3$ are each a methoxy group, $R^1$, $R^4$ and $R^5$ are each a hydrogen atom, and n=0:

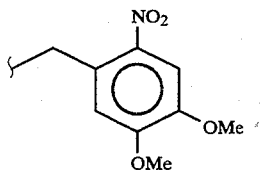

A preferred protecting group, 6-nitroveratryloxycarbonyl (NVOC), which is used to protect the amino terminus of an amino acid, or the hydroxyl group of a nucleotide, sugar, or carbohydrate for example, is formed when $R^2$ and $R^3$ are each a methoxy group, $R^1$, $R^4$ and $R^5$ are each a hydrogen atom, and n=1:

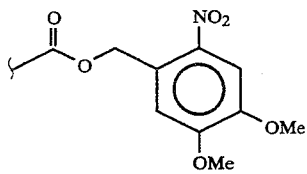

Another preferred protecting group, 6-nitropiperonyl (NP), which is used for protecting the carboxyl terminus of an amino acid or the hydroxyl group of a nucleotide, sugar, or carbohydrate for example, is formed when $R^2$ and $R^3$ together form a methylene acetal, $R^1$, $R^4$ and $R^5$ are each a hydrogen atom, and n=0:

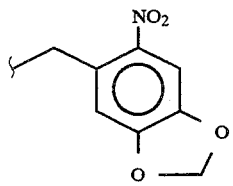

Another preferred protecting group, 6-nitropiperonyloxycarbonyl (NPOC), which is used to protect the amino terminus of an amino acid, or the hydroxyl group of a nucleotide, sugar, or carbohydrate for example, is formed when $R^2$ and $R^3$ together form a methylene acetal, $R^1$, $R^4$ and $R^5$ are each a hydrogen atom, and n=1:

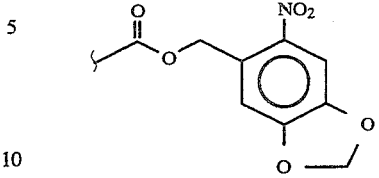

A most preferred protecting group, methyl-6-nitroveratryl (MeNV), which is used for protecting the carboxyl terminus of an amino acid or the hydroxyl group of a nucleotide, sugar or carbohydrate for example, is formed when $R^2$ and $R^3$ are each a methoxy group, $R^1$ and $R^4$ are each a hydrogen atom, $R^5$ is a methyl group, and n=0:

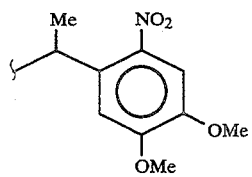

Another most preferred protecting group, methyl-6-nitroveratryloxycarbonyl (MeNVOC), which is used to protect the amino terminus of an amino acid, or the hydroxyl group of a nucleotide, sugar, or carbohydrate for example, is formed when $R^2$ and $R^3$ are each a methoxy group, $R^1$ and $R^4$ are each a hydrogen atom, $R^5$ is a methyl 5 group, and n=1:

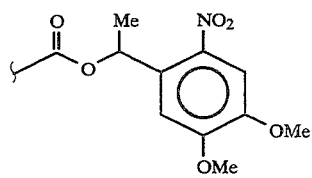

Another most preferred protecting group, methyl-6-nitropiperonyl (MeNP), which is used for protecting the carboxyl terminus of an amino acid or the hydroxyl group of a nucleotide, sugar or carbohydrate for example, is formed when $R^2$ and $R^3$ together form a methylene acetal, $R^1$ and $R^4$ are each a hydrogen atom, $R^5$ is a methyl group, and n=0:

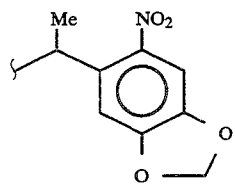

Another most preferred protecting group, methyl-6-nitropiperonyloxycarbonyl (MeNPOC), which is used to protect the amino terminus of an amino acid or to protect the 5' hydroxyl of nucleosides, nucleotides, carbohydrates, or sugars for example, is formed when $R^2$ and $R^3$ together form a methylene acetal, $R^1$ and $R^4$ are each a hydrogen atom, $R^5$ is a methyl group, and n=1:

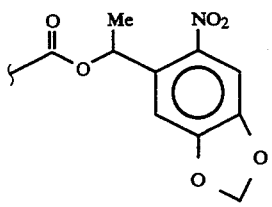

A protected amino acid having a photoactivatable oxycarbonyl protecting group, such NVOC or NPOC or their corresponding methyl derivatives, MeNVOC or MeNPOC, respectively, on the amino terminus is formed by acylating the amine of the amino acid or 5'hydroxyl of a nucleotide, sugar or carbohydrate with an activated oxycarbonyl ester of the protecting group. Examples of activated oxycarbonyl esters of NVOC and MeNVOC have the general formula:

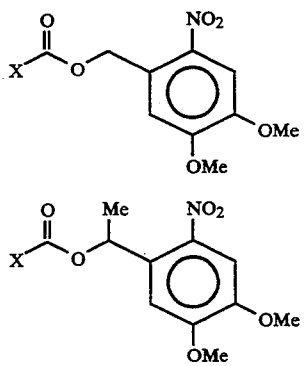

where X is halogen, mixed anhydride, phenoxy, p-nitrophenoxy, N-hydroxysuccinimide, and the like.

A protected amino acid or nucleotide having a photoactivatable protecting group, such as NV or NP or their corresponding methyl derivatives, MeNV or MeNP, respectively, on the carboxy terminus of the amino acid or 5'-hydroxy terminus of the nucleotide, is formed by acylating the carboxy terminus or 5'-OH with an activated benzyl derivative of the protecting group. Examples of activated benzyl derivatives of MeNV and MeNP have the general formula:

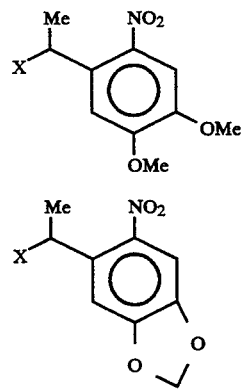

where X is halogen, hydroxyl, tosyl, mesyl, trifluoromethyl, diazo, azido, and the like.

Another method for generating protected monomers is to react the benzylic alcohol derivative of the protecting group with an activated ester of the monomer. For example, to protect the carboxyl terminus of an amino acid, an activated ester of the amino acid is reacted with the alcohol derivative of the protecting group, such as 6-nitroveratrol (NVOH). Examples of activated esters suitable for such uses include halo-formate, mixed anhydride, imidazoyl formate, acyl halide, and also include formation of the activated ester in situ the use of common reagents such as DCC and the like. See Atherton et al. for other examples of activated esters.

A further method for generating protected monomers is to react the benzylic alcohol derivative of the protecting group with an activated carbon of the monomer. For example, to protect the 5'-hydroxyl group of a nucleic acid, a derivative having a 5'-activated carbon is reacted with the alcohol derivative of the protecting group, such as methyl-6-nitropiperonol (MeNPOH). Examples of nucleotides having activating groups attached to the 5'-hydroxyl group have the general formula:

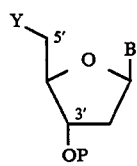

where Y is a halogen atom, a tosyl, mesyl, trifluoromethyl, azido, or diazo group, and the like.

Another class of preferred photochemical protecting groups has the formula:

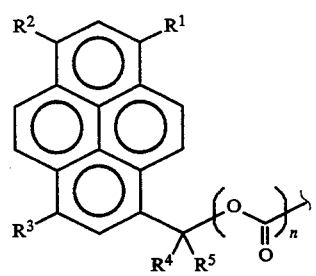

where $R^1$ $R^a$ and $R^3$ independently are a hydrogen atom, a lower alkyl, aryl, benzyl, halogen, hydroxyl, alkoxyl, thiol, thioether, amino, nitro, carboxyl, formate, formamido, sulfanates, sulfido or phosphido group, $R^4$ and $R^5$ independently are a hydrogen atom, an alkoxy, alkyl, halo, aryl, or alkenyl group, and n=0 or 1.

A preferred protecting group, 1-pyrenylmethyloxycarbonyl (PyROC), which is used to protect the amino terminus of an amino acid, or the hydroxyl group of nucleotide, sugar or carbohydrate for example, is formed when $R^1$ through $R^5$ are each a hydrogen atom and n=1:

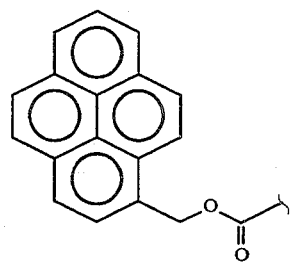

Another preferred protecting group, 1-pyrenylmethyl (PyR), which is used for protecting the carboxy terminus of an amino acid or the hydroxyl group of a nucleotide, sugar or carbohydrate for example, is formed when $R^1$ through $R^5$ are each a hydrogen atom and $n=0$:

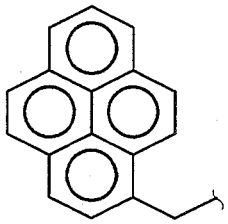

An amino acid having a pyrenylmethyloxycarbonyl protecting group on its amino terminus is formed by acylation of the free amine of amino acid with an activated oxycarbonyl ester of the pyrenyl protecting group. Examples of activated oxycarbonyl esters of PyROC have the general formula:

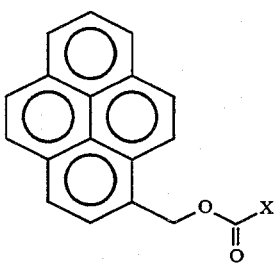

where X is halogen, or mixed anhydride, p-nitrophenoxy, or N-hydroxysuccinimide group, and the like.

A protected amino acid or nucleotide having a photoactivatable protecting group, such as PyR, on the carboxy terminus of the amino acid or 5'-hydroxy terminus of the nucleic acid, respectively, is formed by acylating the carboxy terminus or 5'-OH with an activated pyrenylmethyl derivative of the protecting group. Examples of activated pyrenylmethyl derivatives of PyROC have the general formula:

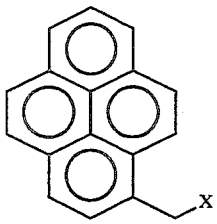

where X is a halogen atom, a hydroxyL, diazo, or azido group, and the like.

Another method of generating protected monomers is to react the pyrenylmethyl alcohol moiety of the protecting group with an activated ester of the monomer. For example, an activated ester of an amino acid can be reacted with the alcohol derivative of the protecting group, such as pyrenylmethyl alcohol (PyROH), to form the protected derivative of the carboxy terminus of the amino acid. Examples of activated esters include halo-formate, mixed anhydride, imidazoyl formate, acyl halide, and also include formation of the activated ester in situ and the use of common reagents such as DCC and the like.

Clearly, many photosensitive protecting groups are suitable for use in the present invention.

In preferred embodiments, the substrate is irradiated to remove the photoremovable protecting groups and create regions having free reactive moieties and side products resulting from the protecting group. The removal rate of the protecting groups depends on the wavelength and intensity of the incident radiation, as well as the physical and chemical properties of the protecting group itself. Preferred protecting groups are removed at a faster rate and with a lower intensity of radiation. For example, at a given set of conditions, MeNVOC and MeNPOC are photolytically removed from the N-terminus of a peptide chain faster than their unsubstituted parent compounds, NVOC and NPOC, respectively.

Removal of the protecting group is accomplished by irradiation to separate the reactive group and the degradation products derived from the protecting group. Not wishing to be bound by theory, it is believed that irradiation of an NVOC- and MeNVOC-protected oligomers occurs by the following reaction schemes:

NVOC-AA -> 3,4-dimethoxy-6-nitrosobenzaldehyde+$CO_2$+AA MeNVOC-AA->3,4-dimethoxy-6-nitrosoacetophenone +$CO_2$+AA where AA represents the N-terminus of the amino acid oligomer.

Along with the unprotected amino acid, other products are liberated into solution: carbon dioxide and a 2,3-dimethoxy-6-nitrosophenylcarbonyl compound, which can react with nucleophilic portions of the oligomer to form unwanted secondary reactions. In the case of an NVOC-protected amino acid, the degradation product is a nitrosobenzaldehyde, while the degradation product for the other is a nitrosophenyl ketone. For instance, it is believed that the product aldehyde from NVOC degradation reacts with free amines to form a Schiff base (imine) that affects the remaining polymer synthesis. Preferred photoremovable protecting groups react slowly or reversibly with the oligomer on the support.

Again not wishing to be bound by theory, it is believed that the product ketone from irradiation of a MeNVOC-protected oligomer reacts at a slower rate with nucleophiles on the oligomer than the product aldehydes from irradiation of-the same NVOC-protected oligomer. Although not unambiguously determined, it is believed that this difference in reaction rate is due to the difference in general reactivity between aldehydes and ketones towards nucleophiles due to steric and electronic effects.

The photoremovable protecting groups of the present invention are readily removed. For example, the photolysis of N-protected L-phenylalanine in solution having different photoremovable protecting groups was analyzed, and the results are presented in the following table:

TABLE 9

Photolysis of Protected L—Phe—OH

| Solvent | $t_{\frac{1}{2}}$ in seconds | | | |
|---|---|---|---|---|
| | NBOC | NVOC | MeNVOC | MeNPOC |
| Dioxane | 1288 | 110 | 24 | 19 |
| 5 mM H$_2$SO$_4$/Dioxane | 1575 | 98 | 33 | 22 |

The half life, $t_{1/2}$, is the time in seconds required to remove 50% of the starting amount of protecting group. NBOC is the 6-nitrobenzyloxycarbonyl group, NVOC is the 6-nitroveratryloxycarbonyl group, MeNVOC is the methyl-6-nitroveratryloxycarbonyl group, and MeNPOC is the methyl-6-nitropyperonylorycarbonyl group. The concentration of each protected phenylalanine was 0.10 mM.

Table 9 shows that deprotection of NVOC-, MeNVOC-, and MeNPOC-protected phenylalanine proceeded faster than the deprotection of NBOC. Furthermore, it shows that the deprotection of the two derivatives that are substituted on the benzylic carbon, MeNVOC and MeNPOC, were photolyzed at the highest rates in both dioxane and acidified dioxane.

1. Use of Photoremovable Groups During Solid-Phase Synthesis of Peptides

The formation of peptides on a solid-phase support requires the stepwise attachment of an amino acid to a substrate-bound growing chain. In order to prevent unwanted polymerization of the monomeric amino acid under the reaction conditions, protection of the amino terminus of the amino acid is required. After the monomer is coupled to the end of the peptide, the N-terminal protecting group is removed, and another amino acid is coupled to the chain. This cycle of coupling and deprotecting is continued for each amino acid in the peptide sequence. See Merrifield, *J. Am. Chemo Soc.* (1963) 85:2149, and Atherton et al , . "Solid Phase Peptide Synthesis" 1989, IRL Press, London, both incorporated herein by reference for all purposes. As described above, the use of a photoremovable protecting group allows removal of selected portions of the substrate surface, via patterned irradiation, during the deprotection cycle of the solid phase synthesis. This selectively allows spatial control of the synthesis—the next amino acid is coupled only to the irradiated areas.

In one embodiment, the photoremovable protecting groups of the present invention are attached to an activated ester of an amino acid at the amino terminus:

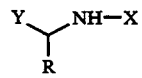

where R is the side chain of a natural or unnatural amino acid, X is a photoremovable protecting group, and Y is an activated carboxylic acid derivative. The photoremovable protecting group, X, is preferably NVOC, NPOC, PyROC, MeNVOC, MeNPOC, and the like as discussed above. The activated ester, Y, is preferably a reactive derivative having a high coupling efficiency, such as an acyl halide, mixed anhydride, N-hydroxysuccinimide ester, HOBT ester perfluorophenyl ester, or urethane protected acid, and the like. Other activated esters and reaction conditions are well known (See Atherton et al.).

2. Use of Photoremovable Protecting Groups During Solid-Phase Synthesis of Oligonucleotides The formation of oligonucleotides on a solid-phase support requires the stepwise attachment of a nucleotide to a substrate-bound growing oligomer. In order to prevent unwanted polymerization of the monomeric nucleotide under the reaction conditions, protection of the 5'-hydroxyl group of the nucleotide is required. After the monomer is coupled to the end of the oligomer, the 5'-hydroxyl protecting group is removed, and another nucleotide is coupled to the chain. This cycle of coupling and deprotecting is continued for each nucleotide in the oligomer sequence. See Gait, "Oligonucleotide Synthesis: A Practical Approach" 1984, IRL Press, London, incorporated herein by reference for all purposes. As described above, the use of a photoremovable protecting group allows removal, via patterned irradiation, of selected portions of the substrate surface during the deprotection cycle of the solid phase synthesis. This selectively allows spatial control of the synthesis-the next nucleotide is coupled only to the irradiated areas.

Oligonucleotide synthesis generally involves coupling an activated phosphorous derivative on the 3-hydroxyl group of a nucleotide with the 5'-hydroxyl group of an oligomer bound to a solid support. Two major chemical methods exist to perform this coupling: the phosphate-triester and phosphoramidite methods (See Gait). Protecting groups of the present invention are suitable for use in either method.

In a preferred embodiment, a photoremovable protecting group is attached to an activated nucleotide on the 5'-hydroxyl group:

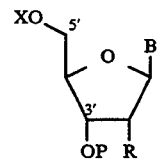

where B is the base attached to the sugar ring; R is a hydrogen atom when the sugar is deoxyribose or R is a hydroxyl group when the sugar is ribose; P represents an activated phosphorous group; and X is a photoremovable protecting group. The photoremovable protecting group, X, is preferably NV, NP, PyR, MeNV, MeNP, NVOC, NPOC, PyROC, MeNVOC, MeNPOC, and the like as described above. The activated phosphorous group, P, is preferably a reactive derivative having a high coupling efficiency, such as a phosphate-triester, phosphoramidite or the like. Other activated phosphorous derivatives, as well as reaction conditions, are well known (See Gait).

E. Amino Acid N-Carboxy Anhydrides Protected With a Photoremovable Group

During Merrifield peptide synthesis, an activated ester of one amino acid is coupled with the free amino terminus of a substrate-bound oligomer. Activated esters of amino acids suitable for the solid phase synthesis include halo-formate, mixed anhydride, imidazoyl formate, acyl halide, and also includes formation of the activated ester in situ and the use of common reagents such as DCC and the like (See Atherton et al.). A preferred protected and activated amino acid has the general formula:

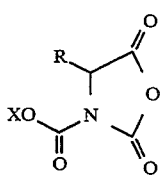

where R is the side chain of the amino acid and X is a photoremovable protecting group. This compound is a urethane-protected amino acid having a photoremovable protecting group attached to the amine. A more preferred activated amino acid is formed when the photoremovable protecting group has the general formula:

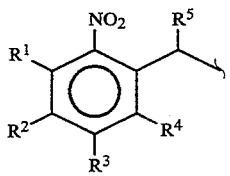

where $R^1$, $R^2$, $R^3$, and $R^4$ independently are a hydrogen atom, a lower alkyl, aryl, benzyl, halogen, hydroxyl, alkoxyl, thiol, thioether, amino, nitro, carboxyl, formate, formamido or phosphido group, or adjacent substituents (i.e., $R^1$-$R^2$, $R^2$-$R^3$, $R^3$-$R^4$) are substituted oxygen groups that together form a cyclic acetal or ketal; and $R^5$ is a hydrogen atom, alkoxyl, alkyl, halo, aryl, or alkenyl group.

A preferred activated amino acid is formed when the photoremovable protecting group is 6-nitroveratryloxycarbonyl. That is, $R^1$ and $R^4$ are each a hydrogen atom, $R^2$ and $R^3$ are each a methoxy group, and $R^3$ is a hydrogen atom. Another preferred activated amino acid is formed when the photoremovable group is 6-nitropiperonyl: $R^1$ and $R^4$ are each a hydrogen atom, $R^2$ and $R^3$ together form a methylene acetal, and $R^5$ is a hydrogen atom. Other protecting groups are possible. Another preferred activated ester is formed when the photoremovable group is methyl-6-nitroveratryl or methyl-6-nitropiperonyl.

Another preferred activated amino acid is formed when the photoremovable protecting group has the general formula:

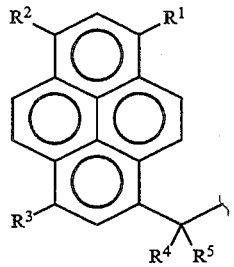

where $R^1$, $R^2$, and $R^3$ independently are a hydrogen atom, a lower alkyl, aryl, benzyl, halogen, hydroxyl, alkoxyl, thiol, thioether, amino, nitro, carboxyl, formate, formamido, sulfanate, sulfido or phosphido group, and $R^4$ and $R^3$ independently are a hydrogen atom, an alkoxy, alkyl, halo, aryl, or alkenyl group. The resulting compound is a urethane-protected amino acid having a pyrenylmethyloxycarbonyl protecting group attached to the amine. A more preferred embodiment is formed when $R^1$ through $R^5$ are each a hydrogen atom.

The urethane-protected amino acids having a photoremovable protecting group of the present invention are prepared by condensation of an N-protected amino acid with an acylating agent-such as an acyl halide, anhydride, chloroformate and the like (See Fuller et al., U.S. Pat. No. 4,946,942 and Fuller et al., *J. Amer. Chem. Soc.* (1990) 112:7414–7416, both herein incorporated by reference for all purposes).

Urethane-protected amino acids having photoremovable protecting groups are generally useful as reagents during solid-phase peptide synthesis, and because of the spatial selectivity possible with the photoremovable protecting groups, are especially useful for the spatially addressable peptide synthesis. These amino acids are difunctional: the urethane group first serves to activate the carboxy terminus for reaction with the amine bound to the surface, and, once the peptide bond is formed, the photoremovable protecting group protects the newly formed amino terminus from further reaction. These amino acids are also highly reactive to nucleophiles, such as deprotected amines on the surface of the solid support, and due to this high reactivity, the solid-phase peptide coupling times are significantly reduced, and yields are typically higher.

IV. Data Collection

A. Data Collection System

Figure 35:
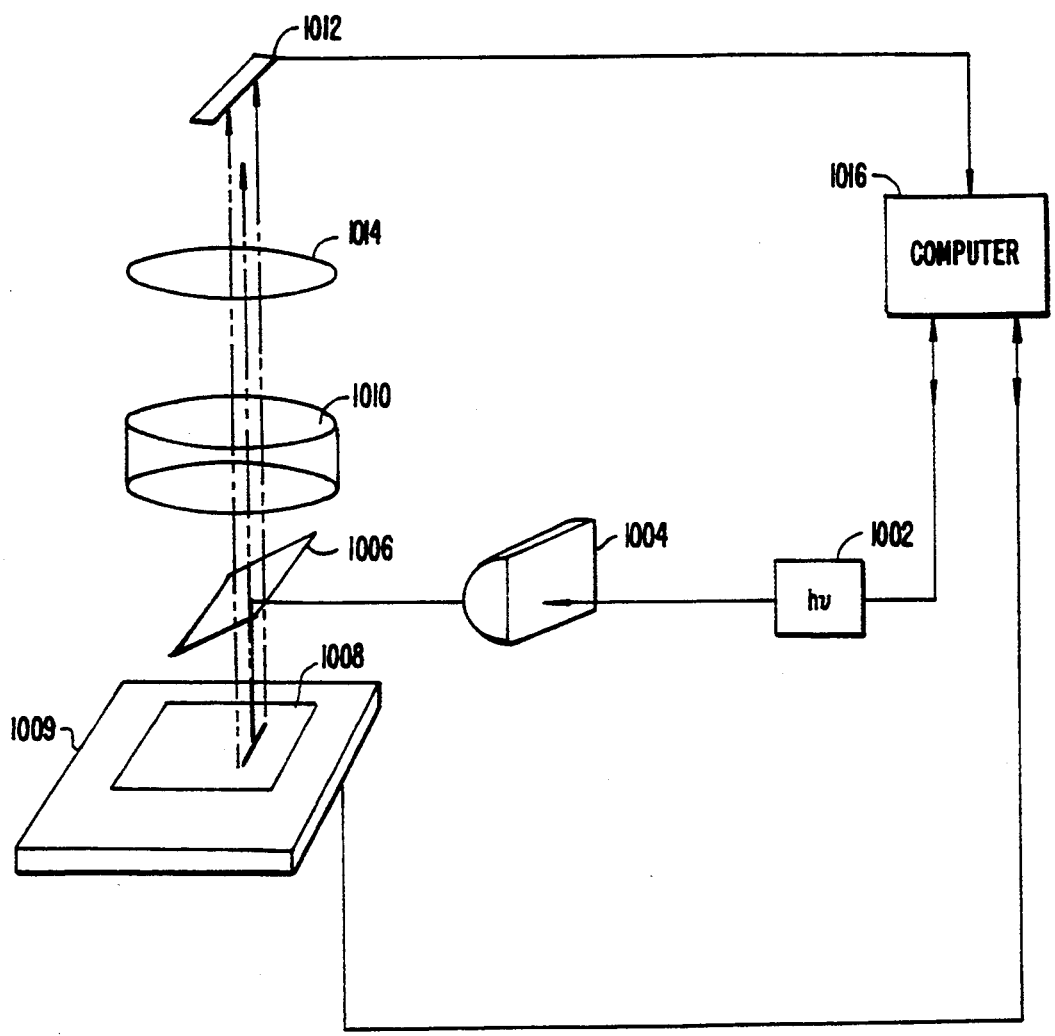
FIG. 35 schematically illustrates a data collection system.

Substrates prepared in accordance with the above description are used in one embodiment to determine which of the plurality of sequences thereon bind to a receptor of interest. FIG. 35 illustrates one embodiment of a device used to detect regions of a substrate which contain flourescent markers. This device would be used, for example, to detect the presence or absence of a fluorescently labeled receptor such as an antibody which has bound to a synthesized polymer on a substrate.

Light is directed at the substrate from a light source 1002 such as a laser light source of the type well known to those of skill in the art such as a model no. 2025 made by Spectra Physics. Light from the source is directed at a lens 1004 which is preferably a cylindrical lens of the type well known to those of skill in the art. The resulting output from the lens 1004 is a linear beam rather than a spot of light. Thus, data can be detected substantially simultaneously along a linear array of pixels rather than on a pixel-by-pixel basis. It will be understood that while a cylindrical lens is used herein as an illustration of one technique for generating a linear beam of light on a surface, other techniques could also be utilized.

The beam from the cylindrical lens is passed through a dichroic mirror or prism and directed at the surface of the suitably prepared substrate 1008. Substrate 1008 is placed on an x-y translation stage 1009 such as a model no. PM500-8 made by Newport. Certain locations on the substrate will fluoresce and fluorescence will be transmitted along the path indicated by dashed lines back through the dichroic mirror, and focused with a suitable lens 1010 such as an f/1.4 camera lens on a linear detector 1012 via a variable f stop focusing lens 1014. Through use of a linear light beam, it becomes possible to generate data over a line of pixels (such as about 1 cm) along the substrate, rather than from individual points on the substrate. In alternative embodiments, light is directed at a 2-dimensional area of the substrate and fluorescence is detected by a 2-dimensional CCD array. Linear detection is preferred because substantially higher power densities are obtained.

Detector 1012 detects the amount of fluorescence emitted from the substrate as a function of position. According to one embodiment the detector is a linear CCD array of the type commonly known to those of skill in the art. The x-y translation stage, the light source, and the detector 1012 are all operably connected to a computer 1016 such as an IBM PC-AT or equivalent for control of the device and data collection from the CCD array.

In operation, the substrate is appropriately positioned by the translation stage. The light source is then illuminated, and fluorescence intensity data are gathered with the computer via the detector.

In a preferred embodiment, the substrate and x/y translation table are placed under a microscope which includes one or more objectives. Light (488 nm) from a laser, which in some embodiments is a model no. 2020-05 argon ion laser manufactured by Spectra Physics, is directed at the substrate by a dichroic mirror which passes greater than about 520 nm light but reflects 488 nm light. The dichroic mirror may be, for example, a model no. FT510 manufactured by Carl Zeiss. Light reflected from the mirror then enters the microscope which may be, for example, a model no. Axioskop 20 manufactured by Carl Zeiss. Fluorescein-marked materials on the substrate will fluoresce >520 nm light, and the fluoresced light will be collected by the microscope and passed through the mirror. The fluorescent light from the substrate is then directed through a wavelength filter and, thereafter through an aperture plate. The wavelength filter may be, for example, a model no. OG530 manufactured by Melles Griot and the aperture plate may be, for example, a model no. 477352/477380 manufactured by Carl Zeiss.

The fluoresced light then enters a photomultiplier tube which in some embodiments is a model no. R943-02 manufactured by Hamamatsu, the signal is amplified in a preamplifier and photons are counted by a photon counter. The number of photons is recorded as a function of the location in the computer. The pre-amp may be, for example, a model no. SR445 manufactured by Stanford Research Systems and the photon counter may be a model no. SR430 manufactured by Stanford Research Systems. The substrate is then moved to a subsequent location and the process is repeated. In preferred embodiments the data are acquired every 1 to 100 μm with a data collection diameter of about 0.8 to 10 μm preferred. In embodiments with sufficiently high fluorescence, a CCD detector with broadfield illumination is utilized.

Figure 36:
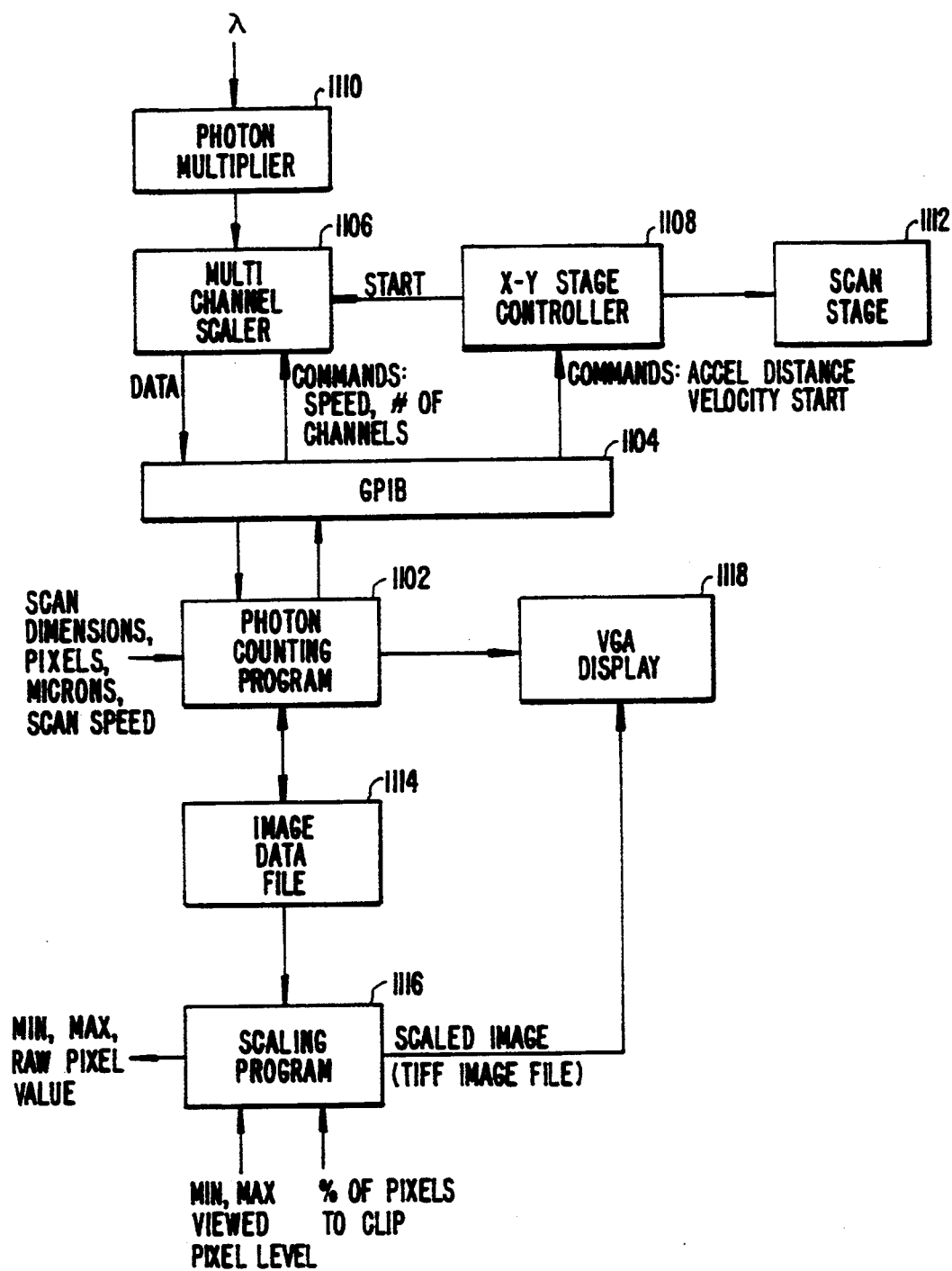
FIG. 36 is a block diagram illustrating the architecture of the data collection system.

FIG. 36 illustrates the architecture of the data collection system in greater detail. Operation of the system occurs under the direction of the photon counting program 1102. The user inputs the scan dimensions, the number of pixels or data points in a region, and the scan speed to the counting program. Via a GPIB bus 1104 the program (in an IBM PC compatible computer, for example) interfaces with a multichannel scaler 1106 such as a Stanford Research SR 430 and an x-y stage controller 1108 such as a Newport PM-500. The signal from the light from the fluorescing substrate enters a photomultiplier 1110, providing output to the scaler 1106. Data are output from the scaler indicative of the number of counts in a given region. After scanning a selected area, the stage controller is activated with commands for acceleration and velocity, which in turn drives the scan stage 1112 such as a Newport PM-500-A to another region.

Data are collected in an image data file 1114 and processed in a scaling program 1116. A scaled image is output for display on, for example, a VGA display 1118. The image is scaled based on an input of the percentage of pixels to clip and the minimum and maximum pixel levels to be viewed. The system outputs for use the min and max pixel-levels in the raw data.

B. Data Analysis

The output from the data collection system is an array of data indicative of fluorescence intensity versus location on the substrate. The data are typically taken over regions substantially smaller than the area in which synthesis of a given polymer has taken place. Merely by way of example, if polymers were synthesized in squares on the substrate having dimensions of 500 microns by 500 microns, the data may be taken over regions having dimensions of 5 microns by 5 microns. In most preferred embodiments, the regions over which florescence data are taken across the substrate are less than about ½ the area of the regions in which individual polymers are synthesized, preferably less than 1/10 the area in which a single polymer is synthesized, and most preferably less than 1/100 the area in which a single polymer is synthesized. Hence, within any area in which a given polymer has been synthesized, a large number of fluorescence data points are collected.

A plot of the number of pixels versus fluorescence intensity for a scan of a cell when it has been exposed to, for example, a labeled antibody will typically take the form of a bell curve, but spurious data are observed, particularly at higher intensities. Since it is desirable to use an average of fluorescence intensity over a given synthesis region in determining relative binding affinity, these spurious data will tend to undesirably skew the data.

Accordingly, in one embodiment of the invention the data are corrected for removal of these spurious data points, and an average of the data points is thereafter utilized in determining relative binding efficiency.

Figure 37:
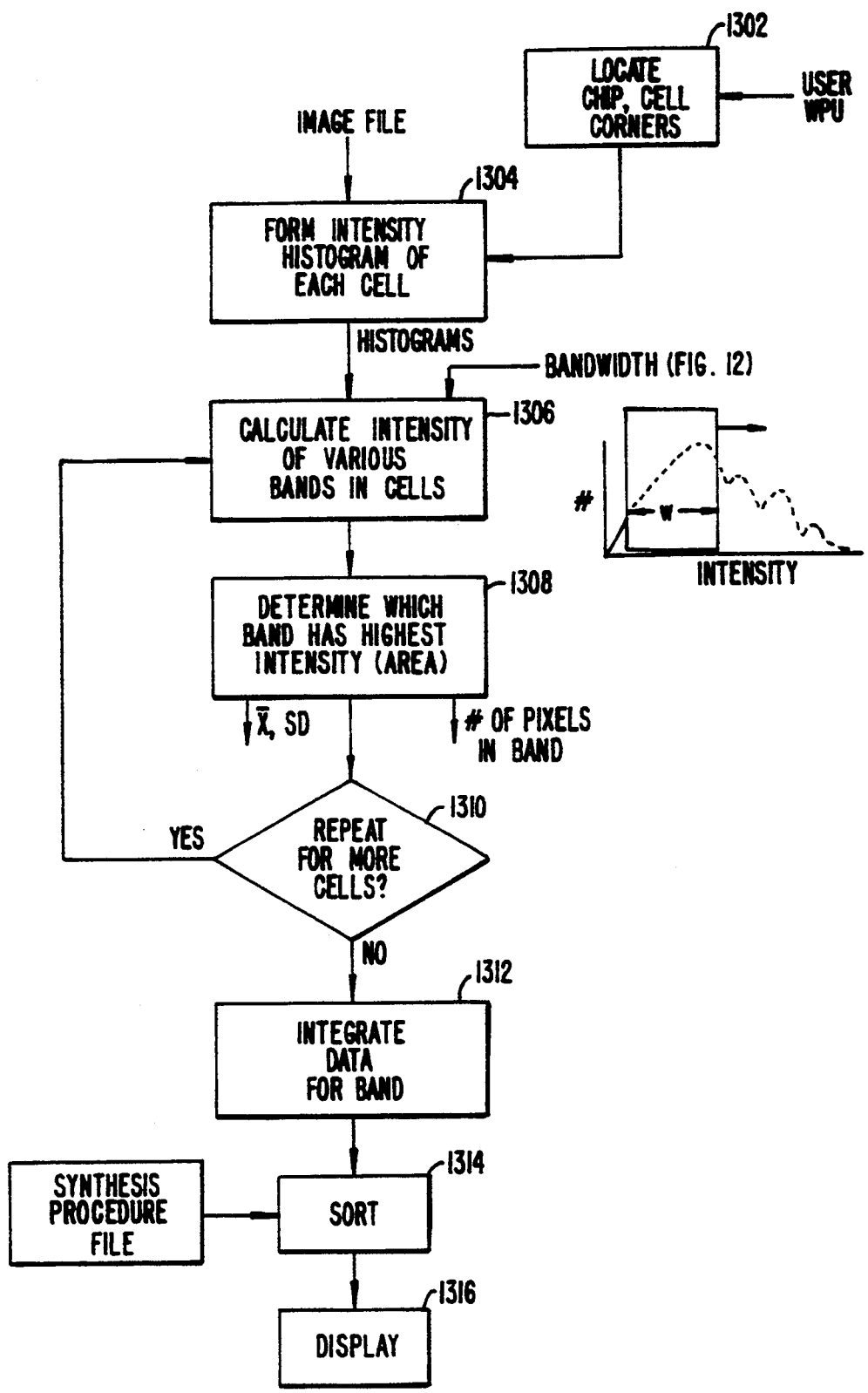
FIG. 37 is a flow chart illustrating operation of software for the data collection/analysis system.

FIG. 37 illustrates one embodiment of a system for removal of spurious data from a set of fluorescence data such as data used in affinity screening studies. A user or the system inputs data relating to the chip location and cell corners at step 1302. From this information and the image file, the system creates a computer representation of a histogram at step 1304, the histogram (at least in the form of a computer file) plotting number of data pixels versus intensity.

For each cell, a main data analysis loop is then performed. For each cell, at step 1306, the system calculates the total fluorescence intensity or number of pixels for the bandwidth centered around varying intensity levels. For example, as shown in the plot to the-right of step 1306, the system calculates the number of pixels within the band of width w. The system then "moves" this bandwidth to a higher center intensity, and again calculates the number of pixels in the bandwidth. This process is repeated until the entire range of intensities have been scanned, and at step 1308 the system determines which band has the highest total number of pixels. The data within this bandwidth are used for further analysis. Assuming the bandwidth is selected to be reasonably small, this procedure will have the effect of eliminating spurious data located at the higher intensity levels. The system then repeats at step 1310 if all cells have been evaluated, or repeats for the next cell.

At step 1312 the system then integrates the data within the bandwidth for each of the selected cells, sorts the data at step 1314 using the synthesis procedure file, and displays the data to a user on, for example, a video display or a printer.

C. Alternative Embodiments

Alternative embodiments of the detection system will be used according to some embodiments of the invention. According to one embodiment of the invention, a slit scanning fluorescence detection system is used in imaging VLSIPS TM chips. Such systems may have improved sensitivity, resolution, contrast, speed of data acquisition, etc. as compared to a pinhole system. Such systems have improved speed of data acquisition, since the image of the VLSIPS chip will be constructed of strips rather than scan lines. High resolution scans of VLSIPS TM chips can take over an hour to acquire with a pinhole system. The advantages of the slit scanning approach depends on the size of the imaged illumination slit (limited in practice by the size of the detector and the magnification of the optical system) and the sensitivity and dark noise of the linear detector used (i.e. how fast the detector is).

Better optical sectioning and hence reduction of background have been reported for a beam-scanning version of this approach. Theoretical calculations and experimental measurements for a scanning mirror/slit microscope using a divided aperture indicate that the contribution to image formation by out-of-plane light scattering/emitting elements will fall off faster with distance than in the case of a pinhole aperture system (Koester (1989), in *Handbook of Biological Confocal Microscopy*, pp 207–214, edited by J. Pawley, Plenum Press, NY, incorporated herein by reference for all purposes). Beam scanning arrangements are unlikely to be of use in near future because of the limited field of view obtained.

Slit scanning systems have been built by others (see references in *Handbook of Biological Confocal Microscopy*, Chapters 1 and 19, incorporated herein by reference).

Other improvements may be made to the system described elsewhere herein. For example, improved image contrast may be obtained by using dielectric barrier filters and a higher numerical aperture microscope objective. These combined modifications improve the detection limit by reducing background fluorescence and laser light scattering. A difficulty in using higher numerical aperture objectives is the shallow depth-of-field, which leads to out-of-focus scans if the thickness of the substrates is nonuniform. As a first step towards solving this problem, a multiple focus and extrapolated x-axis control mechanism may be utilized.

An alternative solution to this problem involves the use of a piezoelectric focusing system which moves the monitor focus (e.g. by bouncing a focused laser off the surface and detecting positional variation with a diode array), a piezoelectric control device may be used to provide real-time autofocus capability.

Alternate fluorophores would also be beneficial in some embodiments. Fluorophores should be evaluated in terms of relative quantum yield, photobleaching stability, and detection sensitivity achieved under the scan conditions we use. To optimize detection sensitivity, fluorophores with larger Stokes' shifts allow better discrimination between emitted light and scattered laser light. In addition, they are less subject to self-quenching phenomena at high packing densities and hence should provide better quantitation of the relative number of fluorophores bound to the surface. Fluorophores with other excitation parameters may also be desirable in some embodiments. For example, Pharmingen makes available of a fluorophore which can be excited with the argon-ion laser and emits above 670 nm.

According to the work of Hirschfeld (Appl. Optics (1976) 15:3135–3139, incorporated herein by reference), the integrated fluorescent emission obtained upon complete bleaching of a fluorescent tag is independent of fluorescence quantum efficiency, absorption cross-section, and illumination intensity. Hence, this approach offers high sensitivity and better quantitation (a greater number of fluorophores can be attached to an antibody or packed into a small area without loss of signal due to quenching), and measurements should be less sensitive to errors in focusing than the scanning approach. The method is probably most suitable for sequential sampling of a small number of sites on a VLSIPS TM surface, although it should also be possible to build a device with a two-dimensional detector for simultaneous readout of many sites, provided that good rejection of excitation light and background fluorescence is achieved.

Time-resolved fluorescence provides an additional approach to enhanced sensitivity through background reduction. Background fluorescence in biological samples usually decays on the time scale of nano- to microseconds. Pulsed excitation of a fluorescent tag having a long lifetime can be detected with high sensitivity by gating the detector so that emitted light is measured after the background has decayed. Immunoassays have been developed using this approach with sensitivities that are reported to approach that of radioisotopic methods (Soini and Kojola (1983) Clin. Chem. (1983) 29:65–68, incorporated herein by reference). This mode of detection is particularly attractive for two reasons. First, considerable experience with rare-earth chelates having long fluorescence lifetimes is available (on the order of 1 msec), and may be able to provide novel additional compounds. Second, this approach allows one to image the VLSIPS TM surface using a two-dimensional detector (e.g., on CCD), resulting in reduced data acquisition time and an instrument that is likely to be much easier to utilize. The use of two-dimensional detectors in our present system is precluded by the necessity of using a pinhole aperture in front of the detector to achieve the confocal condition necessary for reduced background. For example, terbium and europium chelates are typically excited in the UV (320–340 nm), and emit at much longer wavelengths (545 nm for terbium and 615 nm for europium). Thus, they offer excellent wavelength discrimination as well as time-resolved discrimination against background fluorescence. To utilize these compounds a pulsed excitation source is utilized (e.g. an acousto-optically modulated argon-ion laser, flash lamp, or pulsed laser), a gated detector, and timing instrumentation.

Chemiluminescence has been reported to provide detection sensitivities comparable to that achieved using radioisotopes, and several products that can be chemically or enzymatically triggered to emit light are commercially available. High detection sensitivity results from measurement of signals against "zero" background (i.e. there's no background excitation light). In preliminary measurements using a commercially available chemiluminescent substrate for alkaline phosphatase (Lumi-Phos 530; Boehringer-Mannheim #1275470), it was possible to detect approximately 10 pmoles of enzyme in a 600 microliter sample using the detection end of the Aminco spectrofluorimeter. The lifetime of the unstable dioxetane intermediate in those experiments appeared to be too long to permit useful imaging of a VLSIPS ™ surface in some embodiments (diffusion of the substrate would create a resolution problem if one used immobilized enzyme), but other compounds may have shorter lifetimes. Alternatively, using tethered substrate (one photon maximum released per surface site) may provide enough light if the collection efficiency were extremely high. In some embodiments, sandwiching a chemiluminescent probe-labeled VLSIPS ™ chip between a CCD detector and a mirror to maximize collection efficiency may be utilized, while a fiber optic faceplate between chip and detector may be utilized to minimize cross-talk.

Other approaches may be utilized in detection of receptor-ligand interactions in some embodiments, e.g. ChemFETS. ChemFETS are semiconductor devices in which the current flowing through the device is modulated by electrostatic interactions between ions in solution and a region of the surface called the "gate". A multiple gate device may be utilized in some embodiments in which different macromolecules (e.g. receptors or antibodies) are immobilized at each gate. Detection of ligand binding may then be possible, either directly for charged ligands, or by using an enzyme-antibody conjugate that gives rise to local pH changes, by monitoring current for each gate region. A related device has recently been commercialized by Molecular Devices.

V. Other Representative Applications

A. Oligonucleotide Synthesis

The generality of light directed spatially addressable parallel chemical synthesis is demonstrated by application to nucleic acid synthesis.

1. Example

Light activated formation of a thymidinecytidine dimer was carried out. A three dimensional representation of a fluorescence scan showing a 7 square by 4 square checkerboard pattern generated by the light-directed synthesis of a dinucleotide was produced. 5'-nitroveratryl thymidine was attached to a synthesis substrate through the 3' hydroxyl group. The nitroveratryl protecting groups were removed by illumination through a 500 μm checkerboard mask. The substrate was then treated with phosphoramidite activated 2'-deoxycytidine. In order to follow the reaction fluorometrically, the deoxycytidine had been modified with an FMOC protected aminohexyl linker attached to the exocyclic amine (5'-0-dimethoxytrityl-4-N-(6-N- fluorenylmethylcarbamoyl-hexylcarboxy)-2'-deoxycytidine). After removal of the FMOC protecting group with base, the regions which contained the dinucleotide were fluorescently label-led by treatment of the substrate with 1 mM FITC in DMF for one hour.

The three-dimensional representation of the fluorescence intensity data showing alternating squares of bright raised pixels reproduces the checkerboard illumination pattern used during photolysis of the substrate. This result demonstrates that oligonucleotides as well as peptides can be synthesized by the light-directed method.

2. Example

Figure 38:
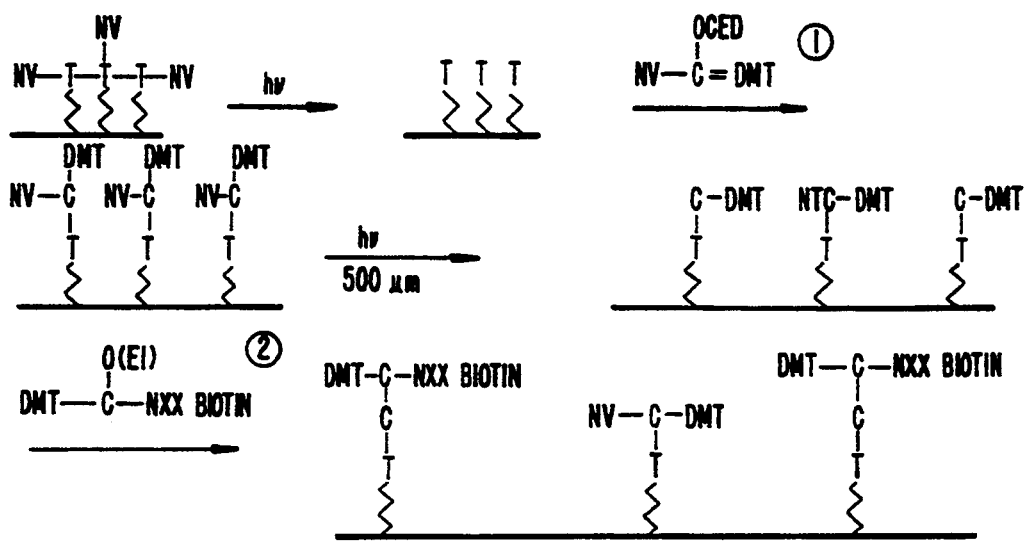
FIG. 38 schematically illustrates one example of light-directed oligonucleotide synthesis.
Figure 38:
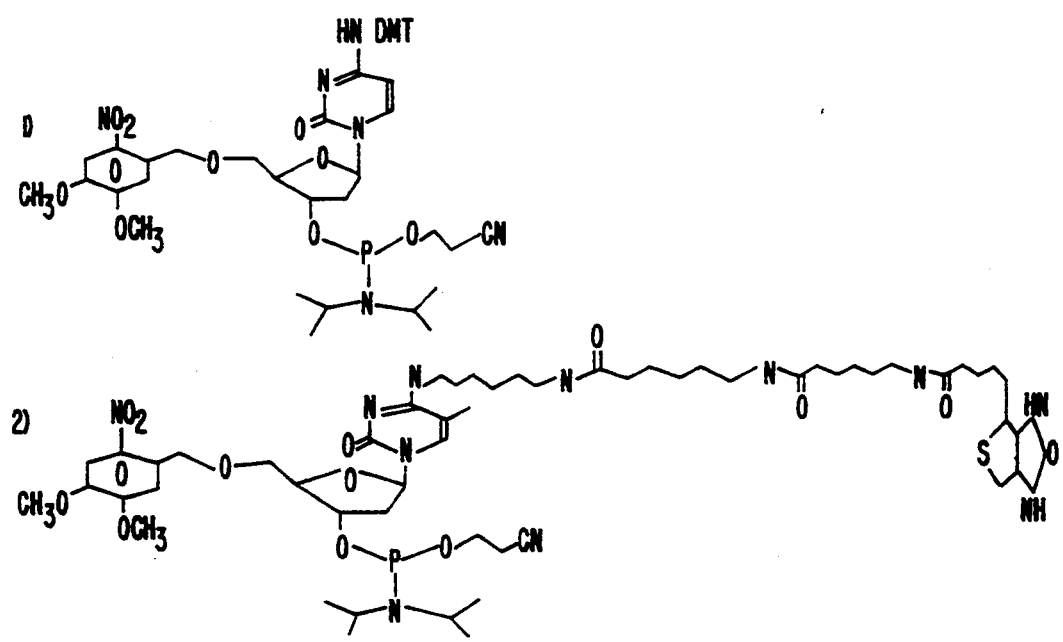

In another example the light-activated formation of thymidine-cytidine-cytidine was carried out as shown in FIG. 38. Here, as in the previous example, 5'-nitroveratryl thymidine was attached to the substrate, via phosphoramidite chemistry to a surface containing [Bis (2-hydroxyethyl)-3-aminopropylsiloxane]. The slide was then uniformly illuminated (362nm at ~14mW/cm$^2$) for 10 minutes in the presence of dioxane. After drying, the surface was then treated with N,4-dimethoxytrityl-5'- nitroveratryl-2'-deoxycytidine-3'-O-(2-cyanoethyl)-N,N-diisopropylphosphoramidite in the presence of tetrazole (standard phosphoramidite coupling chemistry). After oxidizing and drying, the plate was again illuminated as before except that a 500 μm checkerboard mask was placed between the light source and the slide. The surface was then exposed to 5'-O-(4,4'-Dimethoxy)-N-4-(6-((Biotinoyl)amino)hexanoyl)amino)hexanoyl, aminohexyl)-5-methyl-2'-deoxycytidine-3-O-(2-cyanoethyl)-N,N-diisopropylphosphoramidite with tetrazale. After oxidizing and drying, the areas which contained the trinucleotide were fluorescently labelled by treatment with FITC labeled streptavidin. A resulting representation of the fluorescence intensity data showed alternating bright and dark squares corresponding to the 500 μm and checkerboard illumination pattern used during photolysis.

3. Example

In another example, an 8 nucleotide, polyadenine oligomer was prepared and later hybridized with a poly thymidine probe. The synthesis was carried out as follows.

Ten 1×3" slides were incubated in a plastic jar filled with 1% bis(2-hydroxylethyl)aminopropyltriethoxysilane in 95% ethanol overnight at room temperature. The slides were then rinsed thoroughly with ethanol, dried with N$_2$ and baked at 110° C. for 1 hour and put in a vacuum desiccator to cool. A surface linker for coupling was prepared by mixing equal volumes of 0.2M monodimethoxytritylpentaethyleneglycol-β-cyanoethylphosphoramidite in anhydrous acetonitrile and 0.45M tetrazole/CH$_3$CN in a glass vial. 0.35 mL of this solution was then dispensed onto the surface of each slide and incubated for 3 min. The slide was rinsed briefly with CH$_3$CN and coupling was repeated with freshly prepared phosphoramidite. Next, the phosphite-triester bond was oxidized to a phosphotriester by dipping the slides into a jar filled with 0.1M iodine solution (2.6 g iodine +80 mL tetrahydrofuran +20mL 2,6-lutidine+2 mL h2O) for 1 min, followed by rinsing thoroughly with CH3CN and drying with N2. The dimethoxytrityl protecting groups were removed by dipping the slides in a staining jar filled with 3% dichloroacetic acid in methylene chloride for 30 sec followed by-rinsing with CH3CH and drying with N2. Steps C and D were then repeated with 0.2M 5'-nitroveratyl-deoxythymidine-3-$\beta$-cyanoethylphosphoramidite. The slides were then incubated for 1 hour in a staining jar filled with capping solution (75 mLs 6.5% DMAP/THF +25 mLs 40% acetic anhydride/60% 2,6-lutidine), and then rinsed thoroughly with CH3CN, dried with N2, and stored in the dark under vacuum.

Polydeoxyadenine (poly-dA12) was prepared on an ABI synthesizer using 1 $\mu$mole 3-amine-ON CPG (Glen Research) and the standard ABI 1 $\mu$mole coupling cycle having final DMT on. The CPG was transferred to a 1.5 mL plastic screw-cap vial where 1.0 mL conc. NH4OH was added. The mixture was incubated for 18 hours at 55° C. to cleave the oligomer from the resin and remove the exocyclic amine protecting groups. The crude oligomer was purified using a PolyPak cartridge (Glen Research) according to the protocol supplied with the columns. The appropriate fractions were pooled and dried by speed-vac. The oligomer was dissolved in 0.9 mL H2O, to which 0.1 mL 10X labelling buffer (1.0M NaHCO3/Na2CO3,pH 9.0) and 0.25 mL freshly prepared 100 mg/mL FITC in DMF were added. The solution was then vortexed and incubated overnight at room temperature. The reaction mixture was purified on a 1×30 cm Sephadex G-25 column using H2O as the mobile phase, and the appropriate fractions were pooled and dried by speed-vac. PAGE analysis showed that the reaction was not 100% complete. The fluoresceinylated oligomer was further purified by reverse phase HPLC (Hamilton PRP-1 semi-preparative column) using a linear gradient of 10–40% CH3CN in 0.1 M Triethylamine acetate, pH 7.6 over 45 min. at a flow rate of 2 mL/mino Fractions were analyzed by PAGE, and the appropriate fractions were pooled and dried by speed-vac. PAGE analysis of the final product showed purity of approximately 99%.

A suitably derivatized slide was placed in a four-chamber flow cell (wells approximately 1.5 cm dia. circles). One well was filled with dioxane. All other wells were covered with black electrical tape. The slide was then exposed to 365 nm light at 11.8 mW/cm$^2$ for a period of 12 min. to remove the photoprotecting groups. The flow cell was then attached to an ABI DNA synthesizer (model 392), and 5'-NV-dT-OCEP coupled to the surface using the modified cycle attached (cyc03 user). No capping step was performed due to the excess phosphoramidite used. The photolysis/synthesis cycles were repeated until poly-(dT)12-OH was synthesized in the well. The slide was removed from the flow cell, rinsed thoroughly with CH3CN and dried with N2. The slide was then incubated in 6X SSPE containing 3% BSA and 0.025% triton X-100 for 30 min. at room temperature to block non-specific binding sites. Next, the slide was transferred to a plastic container filled with 20 ng/mL 5'-HO-poly(dA) 12-fluorescein in the same buffer and incubated at room temperature for 1 hour. The slide was briefly rinsed in a 20 mM NaCl solution, dried with N2, and detected using-the confocal microscopy system previously described. Average photon counts in the well were 8-fold higher than the background producing the image shown in FIG. 39A. The slide was incubated overnight in 500 mLs 1X SSPE at 40° C. rinsed and scanned FIG. 39A shows a bright circle in the center indicating that this wash removed the signal as shown in FIG. 39B. Reprobing as before resulted in a signal with the same intensity as that originally obtained as shown in FIG. 39C.

For sample 59–8b-1, -2, and -3, the average intensities were 347+/-25, 211+/-23 and 223+/-13 respectively in the background. For samples 59-8b-1 and 59-8b-3 the signal in the well was 4545+/- 476 and 237+/-308 respectively. Therefore, for sample 1 the signal/background ratio was 13, and it was 11 for sample no. 3. The sample number 59-8b-1 refers to the first probe. The sample no. 59-8b-2 refers to the scan after incubation at 40° C. The sample 59-8b-3 is the reprobe sample.

B. Oligosaccharide Synthesis

The present invention will find application in a wide variety of additional applications including oligosaccharide synthesis.

1. Example

The potential synthesis of a C-glycoside unit that will be attached to the surface is outlined below. FIG. 40A illustrates the overall synthesis strategy.

The methyl glycoside of D-glucose is first converted through a standard protection-deprotection sequence to the diacetate. Selective esterification of the primary alcohol is then conducted, followed by etherification of the secondary alcohol with a photolabile protecting group and C-allylation, which provides the C-glycoside. Oxidation of the olefin effects conversion to the carboxylic acid which is then attached to the surface-through standard amide coupling. Photodeprotection will free a hydroxyl group on the monosaccharide for the purposes of examining glycosidic bond formation on the chip surface.

FIG. 40B illustrates formation of a simple activated building block used especially for purposes of examining chemical glycosidic bond formation. The building block is formed D-glucose.

Conversion to the 6-amino derivative is effected through fairly simple methods, such as shown in the first step of the Figure. Protection of the amino function followed by exhaustive acetylation provides the fully protected methyl glycoside. Conversion to a activated glycosyl donor is done by hydrolysis and conversion to the bromide. This material may be attached to a substrate as shown in FIG. 40C. Coupling of the activated bromide to the surface attached glycosyl acceptor will be monitored through the agency of protected 6-amino function on the donor. Photodeprotection followed by labeling with fluorescein isothiocyanate will provide a sensitive assay for the formation of the glycosidic bond.

Figure 40D:
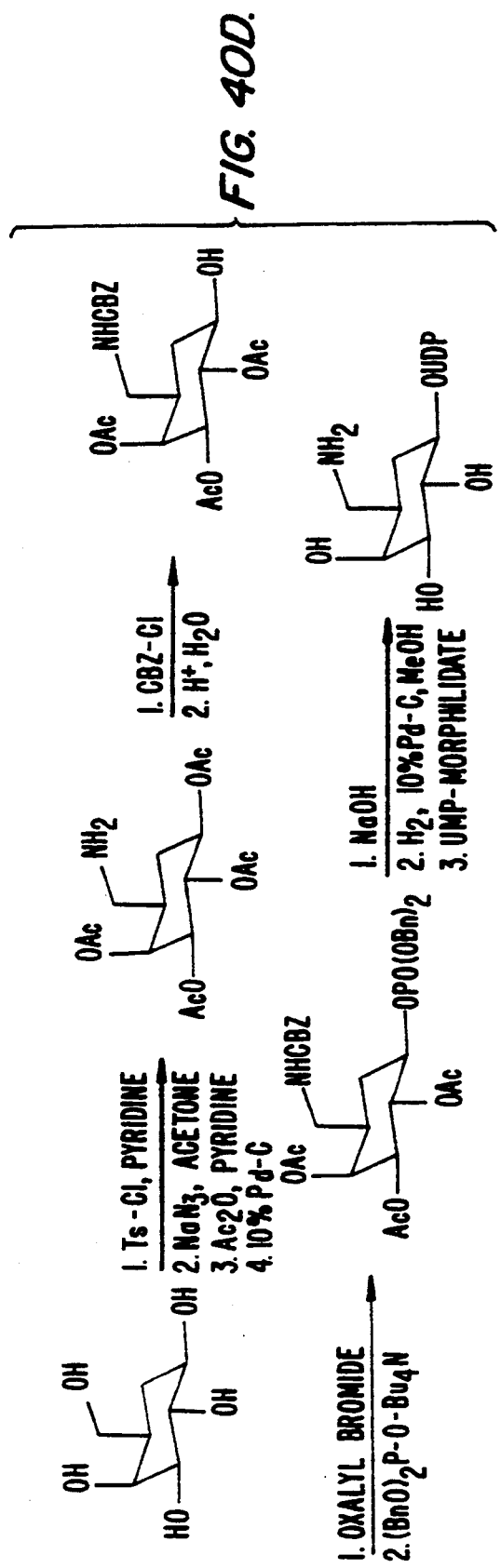
Figure 40E:
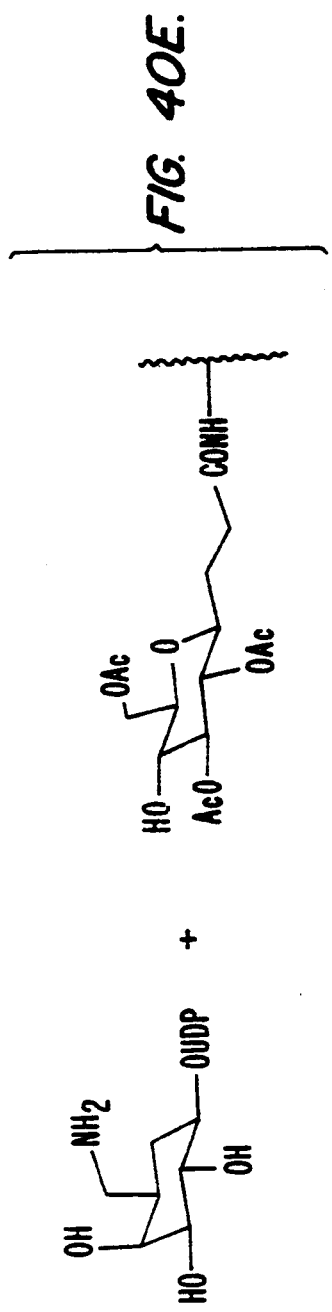

Examination of enzymatic glycosidic bond formation requires the synthesis of a nucleoside diphosphate sugar. One possible scheme is illustrated in FIG. 40D. The introduction of the amino group and exhaustive acetylation is accomplished by standard methods such as those shown in the Figure. Protection of the amine and glycoside hydrolysis leads to the free sugar which is now activated via conversion to the bromide followed by displacement to the anomeric phosphate derivative. Conversion to the uridine diphosphate (UDP) derivative is accomplished through fairly standard methodology, such as the one shown. The product may then be attached to the substrate as shown in FIG. 40E.

Formation of the glycosidic bond between the nucleotide diphosphate sugar and the immobilized saccharide on the VLSIPS ™ chip with galactosyl transferase may also be examined. Coupling of the nucleoside glycoside donor to the surface attached glycosyl acceptor will be monitored through the agency of the 6-amino function on the donor. Labeling of the free amine with fluorescein isothiocyanate will provide a sensitive assay for the formation of the glycosidic bond.

C. Caged Binding Member System

According to an alternative embodiment of the invention, the methods provide for attaching to the surface a caged binding member which in its caged form has a relatively low affinity for other potentially binding species, such as receptors and specific binding substances. Such techniques are more fully described in copending application U.S. Ser. No. 404,920, filed Sep. 8, 1989, and incorporated herein by reference for all purposes.

According to this alternative embodiment, the invention provides methods for forming predefined regions on a surface of a solid support, wherein the predefined regions are capable of immobilizing receptors. The methods make use of caged binding members attached to the surface to enable selective activation of the predefined regions. The caged binding members are liberated to act as binding members ultimately capable of binding receptors upon selective activation of the predefined regions. The activated binding members are then used to immobilize specific molecules such as receptors on the predefined region of the surface. The above procedure is repeated at the same or different sites on the surface so as to provide a surface prepared with a plurality of regions on the surface containing, for example, the same or different receptors. When receptors immobilized in this way have a differential affinity for one or more ligands, screenings and assays for the ligands can be conducted in the regions of the surface containing the receptors.

The alternative embodiment may make use of novel caged binding members attached to the substrate. Caged (unactivated) members have a relatively low affinity for receptors of substances that specifically bind to uncaged binding members when compared with the corresponding affinities of activated binding members. Thus, the binding members are protected from reaction until a suitable source of energy is applied to the regions of the surface desired to be activated. Upon application of a suitable energy source, the caging groups labilize, thereby presenting the activated binding member. A typical energy source will be light.

Once the binding members on the surface are activated they may be attached to a receptor. The receptor chosen may be a monoclonal antibody, a nucleic acid sequence, a drug receptor, etc. The receptor will usually, though not always, be prepared so as to permit attaching it, directly or indirectly, to a binding member. For example, a specific binding substance having a strong binding affinity for the binding member and a strong affinity for the receptor or a conjugate of the receptor may be used to act as a bridge between binding members and receptors if desired. The method uses a receptor prepared such that the receptor retains its activity toward a particular ligand.

Preferably, the caged binding member attached to the solid substrate will be a photoactivatable biotin complex, i.e., a biotin molecule that has been chemically modified with photoactivatable protecting groups so that it has a significantly reduced binding affinity for avidin or avidin analogs than does natural biotin. In a preferred embodiment, the protecting groups localized in a predefined region of the surface will be removed upon application of a suitable source of radiation to give binding members, that are biotin or a functionally analogous compound having substantially the same binding affinity for avidin or avidin analogs as does biotin.

In another preferred embodiment, avidin or an avidin analog is incubated with activated binding members on the surface until the avidin binds strongly to the binding members. The avidin so immobilized on predefined regions of the surface can then be incubated with a desired receptor or conjugate of a desired receptor. The receptor will preferably be biotinylated, e.g., a biotinylated antibody, when avidin is immobilized on the predefined regions of the surface. Alternatively, a preferred embodiment will present an avidin/biotinylated receptor complex, which has been previously prepared, to activated binding members on the surface.

D. Fingerprinting for Quality Control

An alternative aspect of this invention involves testing a therapeutic compound with an array of peptides or other biological polymers to determine a characteristic binding pattern. Such a characteristic binding pattern or "fingerprint" is used to monitor the "constancy" of the compound over time by repeated testing with the same array. As long as the fingerprint remains unchanged from lot-to-lot, the bioprocess is producing the same product. If the binding pattern of the therapeutic changes at any time, it would be assumed that a subtle (or not so subtle) change in the therapeutic compound had occurred. For example, changes in the glycosylation or secondary structure of the protein could be detected. This method promises to be particularly valuable with recombinant and other products produced by fermentation processes where quality control is problematic.

Preferably, the method would be performed with a very large array of biological polymers (thousands or tens of thousands of elements). A VLSIPS ™ or caged biotin chip with binding components to a very broad spectrum of polymer characteristics would be employed. The elements of the array could thus be arranged in a quasi-random manner. Alternatively, they might be organized in a rational order. For example, certain physical properties (e.g., charge or hydrophobicity) of the constituent polymers might vary gradually along a given spatial dimension. Chips having this configuration could then be used for the QC of various biological products. Custom chips specific for a single product, such as for example tissue plasminogen activator (tPA), might also be useful.

E. $\beta$-Amino Acid and D-Amino Acid Monomers

The peptide diversity available in the present invention is greatly increased by including non-natural amino acids (i.e. amino acids which are not genetically coded) among the set of building blocks. In particular, peptides containing at least one $\beta$-amino acids or D-amino acid residue may be synthesized by the methods of the present invention. In addition, L-amino or D-amino acids having modified side chains may be employed to diversify the peptide products available. Cyclic $\beta$-amino acid monomers may be employed to reduce the increased conformational mobility associated with acyclic β-amino acids. In fact, an ordered series of dihedral angles between the amido and carboxamido groups of the peptide backbone may be obtained by changing the number and constituent atoms of the cyclic β-amino acid ring. Such an ordered series of compounds may be useful in optimizing the biological activity of a peptide drug. Since D-amino acids and β-amino acids of any sort are not subject to proteolytic cleavage, incorporation of these residues into peptide drugs should to confer favorable properties of biological stability.

Amino acid monomers (D-, L- or β-) with side chains that are not found on the genetically coded amino acids may also be used in preparing peptides according to the present invention. Amino acids containing aromatic residues are of particular interest because they are commonly present in biologically active binding sites and in drugs. Although they are generally hydrophobic, aromatic side chains can adopt a variety of electronic configurations depending upon the substituents present.

Using phenylalanine as an example, a variety of modifications to the side chain are available, some of which are represented below. Each amino acid containing the groups below can be employed as a monomer without requiring side chain protecting groups often necessary for peptide synthesis.

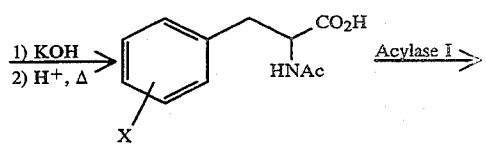

Like genetically coded L-amino acids, D-amino acids must be protected at the α-amino group during peptide synthesis. In addition, the side chain may also have to be protected against unwanted side reactions. The methods of protection set forth above for L-amino acids can also be applied to D-isomers and amino acids with modified side chains. The resulting protected monomers can then be employed to synthesize an array of peptides (or peptide analogs) using the protectiondeprotection methods outlined above.

Polymer backbones comprised of β-amino acids have several advantages. For example, they retain amide bonds, which permits hydrogen bonding in all directions normal to the main chain. The side chain density will be high for a given oligomer length so long as the side chains are placed at both α and β carbons. Considerable control over the properties of the peptide is gained by selecting appropriate substituents. For example, attaching an alkyl group to the β carbon, makes the backbone more hydrophobic than the corresponding α-amino acids. Additional control of the peptide conformation is also possible. Although extra conformational freedom is permitted by the β-carbon in straight chain β-amino acids, conformational restriction within the individual monomer units is also possible by selecting appropriate side chains and cyclic groups, as will be shown below.

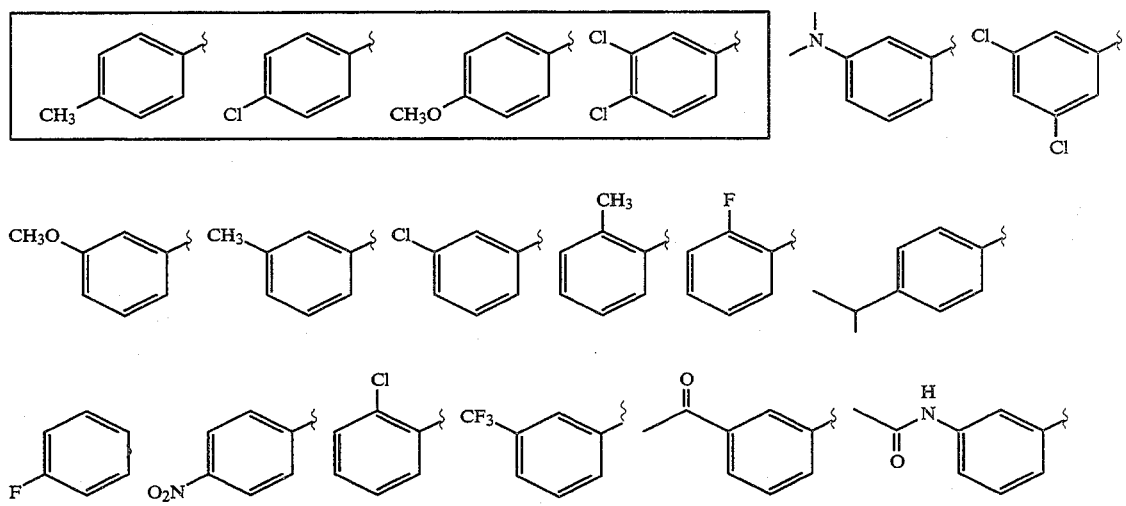

Many of these compounds are commercially available. Those that are not may be synthesized by a variety of well-known procedures. A preferred choice is alkylation of acetamidomalonate with the appropriate benzylic halide, followed by hydrolysis, decarboxylation and enzymatic resolution with *Aspergillus acylase* I as shown below and described in Chenault et al., J. Am. Chem. Soc. (1989) 111:6354–6364 which is incorporated herein by reference for all purposes.

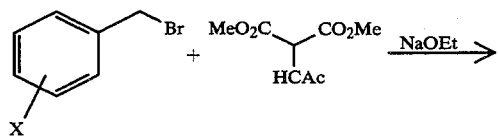

Simple β-amino acids which may be used in the present invention will have an amino acid side chain at either the α or β carbon, and a methyl group or hydrogen atom at the other (types I through IV shown below). Each of the methyl compounds (types I and II below) will include four distinct stereoisomers for each amino acid chain, representing a total of 160 compounds when all of the genetically-coded side chains are employed. Replacing the methyl group with a hydrogen atom (groups III and IV), reduces the number of stereoisomers to two for each side chain.

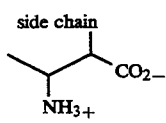 type I

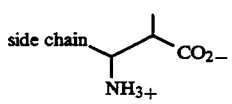 type II

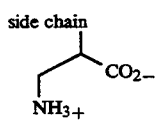 type III

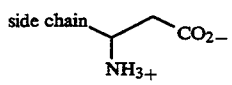 type IV

Three methods for preparing β-amino acids shown below are summarized in Griffith, Annu. Rev. Biochem. (1989) 25:855–878 which is incorporated herein by reference for all purposes. The condensation of cyanoacetic ester with carbonyl compounds or alkyl halides followed by reduction provides structures of type III. The Arndt-Eistert homologation of protected amino acids will give compounds having the structures of type IV. Conjugate addition of ammonia to α,β-unsaturated esters will produce compounds of types I–IV, depending on substituents in the ester starting material.

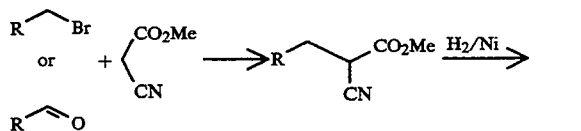

Arndt-Eistert

Conjugate addition

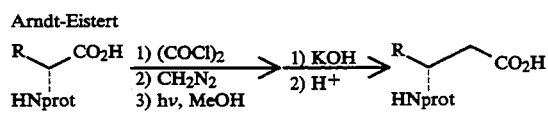

Two other synthetic routes (shown below) which may be employed to synthesize β-amino acids take advantage of the functional relation of β-lactams (which have well-known chemistries) and β-amino acids. These methods are detailed in various references, including Kamal et al., Heterocycles (1987) 26:1051–1076 and Hart et al., Chem. Rev. (1989) 89,:1447–1465, both of which are incorporated herein by reference for all purposes. The first synthetic route exploits the cycloaddition reactions of chlorosulfonyl isocyanate (CSI) with alkenes to give, after hydrolysis, β-lactams. These can then be hydrolyzed to give the corresponding the β-amino acids. Because of the polar mechanism for the CSI cycloaddition, it is not possible to use this reaction to prepare type III compounds which have no substitution on the carbon atom adjacent to the nitrogen atom. The second route employs the condensation of enolates with imines, to produce β-lactams. Optically active compounds are provided this method, but the basic reaction with diazomethane gives only type IV structures. Type II structures may be prepared if diazomethane is substituted with diazoethane and the resulting diastereomers are separated. This synthesis route has the added advantage that it may directly provide protected amino acids for peptide synthesis.

Chlorosulfonylisocyanate

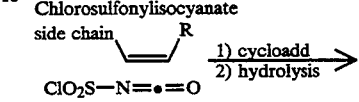

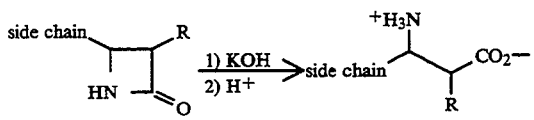

Enolate-imine

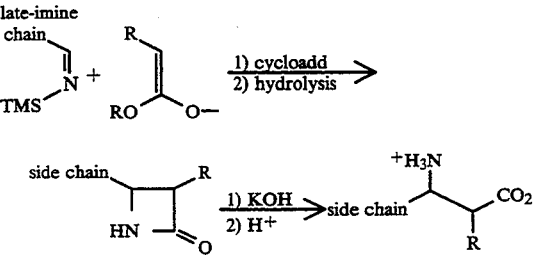

In situations where the most convenient methods do not offer the opportunity for asymmetric synthesis (all but the Arndt-Eistert and enolate-imine reactions described above), the β-amino acids must be resolved and assayed for optical purity. If the methyl-substituted compounds (types I or II above) are prepared in a non-stereoselective route, the diastereomers must also be separated. Amides of type IV β-amino acids may be enantioselectively hydrolyzed by benzylpenicillinacylase. In addition, β-lactamases may be employed to enantiospecifically hydrolyze β-lactams to β-amino acids.

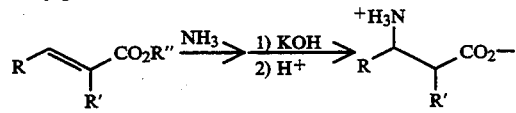

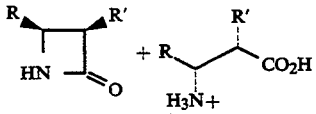

Other methods of separating the isomers will be known to those of skill in the art. In any event, analysis of the optical purity of the products can be accomplished by chirat chromatography or the Mosher method. The absolute configuration, which must be determined for each compound prepared, can be assigned by chiroptical methods.

One skilled in the art will be able to readily determine an appropriate strategy for synthesizing peptides from various β-amino acid monomers employed in the present invention. However, it should be noted that some classical methods of peptide coupling (mixed anhydride, DCC) will not work with some β-amino acids. While not wishing to-be bound by theory, it is believed that the lack of a group at the α-carbon causes increased side reactions of the activated carboxyl group. Another possible side reaction which should be avoided is formation of a dihydrooxazinone, which has been observed in some cases and which may participate in the coupling reaction.

Successful synthesis strategies for some homopolymers (e.g., poly (β-amino butyrate)) include polymerization of β-lactams. See e.g. Chen et al., Macromolecules (1974) 7:779 which is incorporated herein by reference for all purposes. Similar methods may be employed in some instances with methods of the present invention. The homopolymers so produced have been found to adopt a β-conformation analogous to the poly(β-hydroxy butyrate) polymers produced by bacteria. The α-esters of aspartic acid also have been oligomerized to form β-peptides, and they form β-sheets when containing eight or more units. Directed synthesis in solution of a tripeptide formed from β-amino butyrate has been accomplished using trichlorophenyl active esters in the presence of hexamethylphosphoramide (HMPA) as described in Drey et al., J. Chem. Soc., Perkin Trans. (1982) 1:1587–1592 which is incorporated herein by reference for all purposes. Other syntheses well-known in the art may be employed in the present invention to produce a variety of peptide oligomers.

Three dihedral angles (shown below) may be controlled in β-peptides.

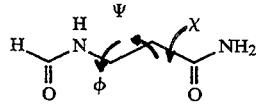

The angle depicted as Ψ above has no analogy in α-peptides and is an angle over which there is appreciable control via the α and β substituents. Considering the erythro and threo isomers of α,β-dimethyl-β-alanine, a prototype disubstituted β-peptide, empirical force field calculations suggest that, in both cases, anti orientation of the methyl groups is favored. This results in the threo isomer introducing a turn in the chain, while the anti isomer would tend to maintain an extended backbone. Certainly, other conformations are close in energy, and will also be populated. However,

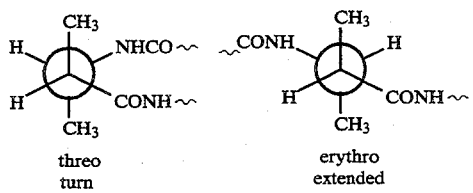

alkyl groups may be linked to a ring to control the rotation of the Ψ bond. This allows variation in the orientation of the main chain in a systematic way. A family of cyclic β-amino acids has been designed for this purpose. The size of the ring onto which the β-amino acid unit is fused and the fusion geometry limit the possibilities for the dihedral angle between the carboxy carbon and the amino group (angle Ψ). For example, the cis-cyclopropyl compound is constrained to eclipse these bonds (Ψ=0°), while the trans-cyclopropyl locks them at a 144° angle. Energy minimization of other members of this homologous series showed an orderly progression of dihedral angles for several low energy conformers.

The generic structure for the cyclic β-amino acid monomers is shown below.

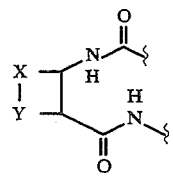

where X is carbon, silicon or the like, and Y is one or more carbon, nitrogen, oxygen, sulfur, silicon or no atom.

Depending on the enantiomeric series to be employed, the turn or extension introduced into the backbone can be either of positive or negative helicity.

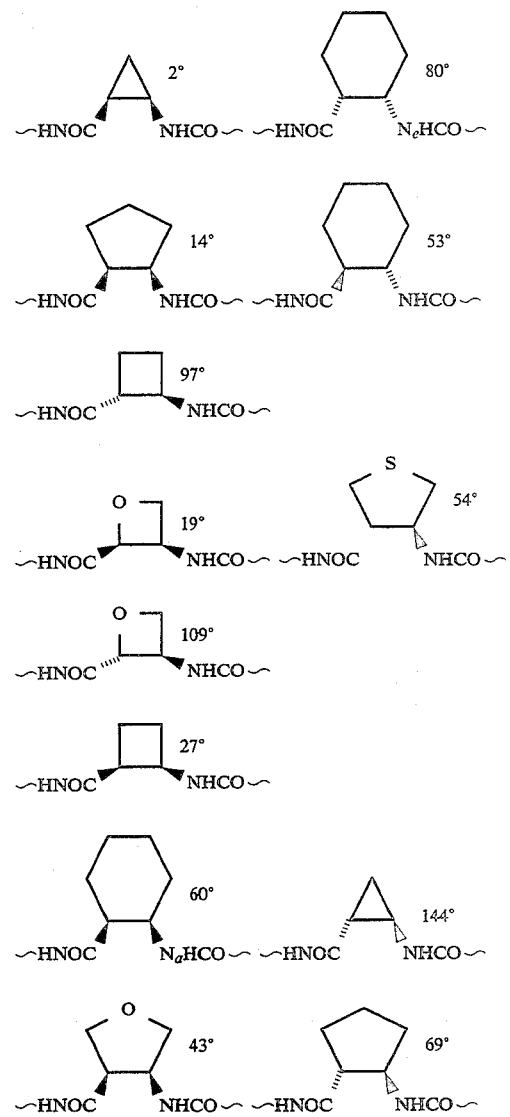

-continued

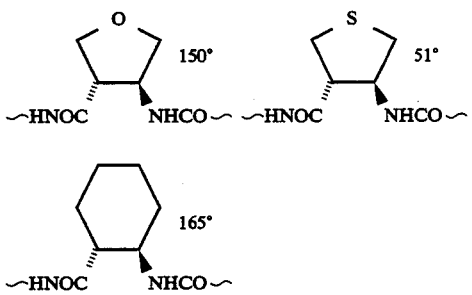

Some of the compounds (e.g., the diaxial cyclohexane system) do not have as a global minimum in the conformation shown, and further constraints may be utilized to enforce the desired stereochemical relationship. These constraints will be well-known in the art and include, by way of example, polar effects, other rings, or allylic strain.

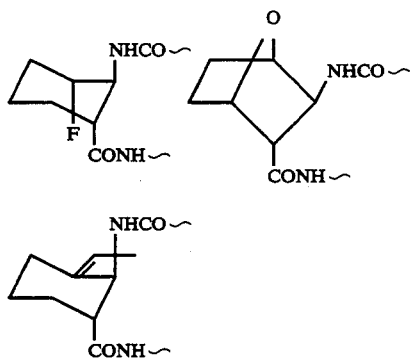

One advantage of this homologous series of compounds is that a unified synthetic approach can be employed. For example, the cycloaddition of chlorosulfonylisocyanate with cycloalkenes may be utilized. This is most applicable to cis isomers of cyclopentyl and cyclohexyl systems. Enantiomer selective enzymatic hydrolysis of the β-lactam then gives the desired β-amino acids ready for derivatization. A second route is more general, and longer. It begins with 1,2-cycloalkanedicarboxylic esters (or their derived diol acetates), which can be prepared via Diels-Alder reactions of maleates or from dianion alkylation of succinate as decribed in Garratt et al., Tetrahedron Lett. (1987) 28:351-352 which is incorporated herein by reference for all purposes. Enzymatic transformation then introduces optical activity and differentiates the carboxyl groups, which permits selective conversion of one into an amino group as described in Sabbioni et al., J. Org. Chem. (1987) 52:4565-4570 which is incorporated by reference herein for all purposes. One advantage of this stategy is that it directly provides the amino protected building block.

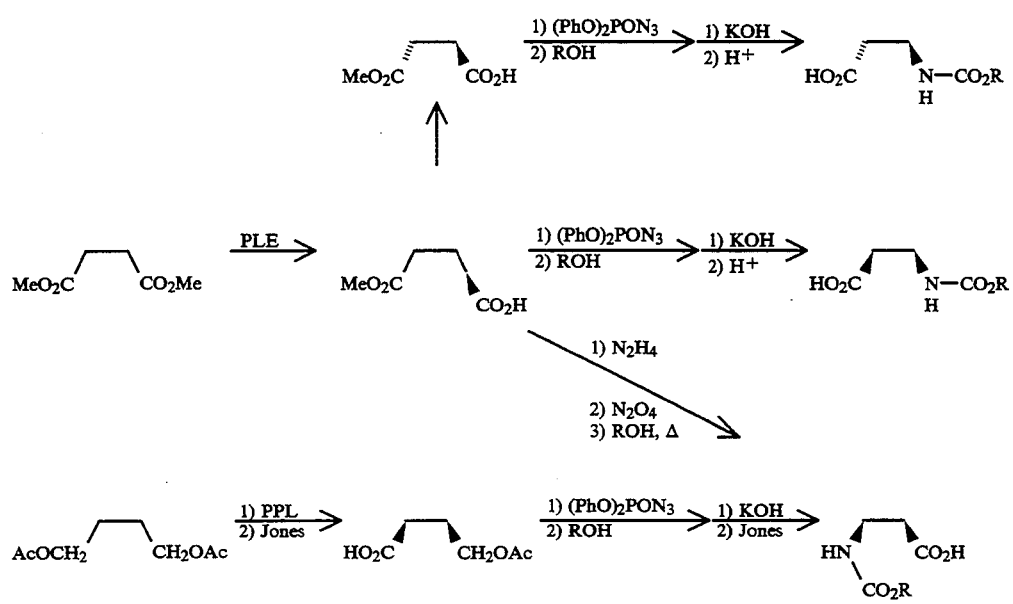

Other compounds related to the above β-amino acid analogues may be employed in peptide syntheses according to the present invention. For example, α-aminoxy acids in which the β-carbon of a β-amino acid is replaced with an oxygen may be used. These compounds are easily prepared in optically active form from the amino acids via the bromo acid. Several peptide analogues incorporating this unit have been synthesized in solution and are known to be resistant to mammalian proteases. See e.g. Briggs et al., J. Chem. Soc. Perkin Trans. (1979) 1:2138-2143 which is incorporated by reference herein for all purposes.

F. Reduced Amide Bonds

Reduced amide peptide isosteres have been incorporated into peptides by reductive alkylation to produce antagonists, enzyme inhibitors, and resistance to biodegradation. For example, in the case of a protease, one can render the scissile bond non-cleavable by introduction of the reduced amide at the cleavage site. In the case of Renin, a reduced peptide analog of the native Renin substrate (H-142) has been shown to reduce blood pressure in clinical tests.

Figure 41:
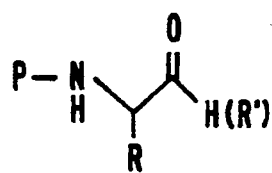
FIG. 41 illustrates the introduction of a reduced amide bond into a growing peptide.
Figure 41:
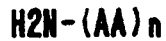
Figure 41:
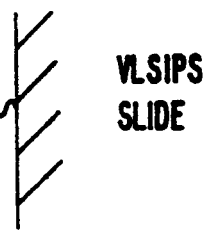
Figure 41:
Figure 41:
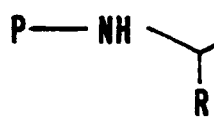
Figure 41:
Figure 41:
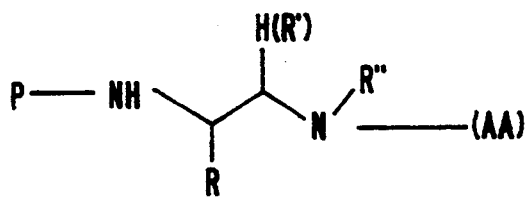
Figure 41:
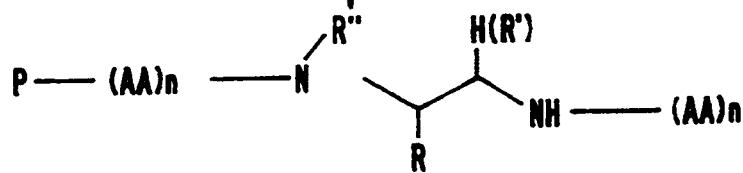
Figure 41:

According to some embodiments, the present invention provides for the introduction of a reduced amide bond into a growing peptide chain or other polymer chain on a substrate in situ, without the preformation of a dipeptide containing a reduced amide bond. FIG. 41 illustrates the introduction of a reduced amide bond into a growing peptide or other polymer. According to a first step of the process, a substrate is formed having an optional chain of amino acids (indicated by $AA_n$) and an exposed amino terminus. The substrate is reacted with an aldehyde derivative of a peptide in the presence of, for example, HCL or AcOH in DMF, providing a substrate with the chain of amino acids and a terminal imine group. The substrate is the reacted with, for example, $NaBH_4$ or $NaCNBH_3$ forming a sequence with a reduced amide bond in the growing polymer chain. The substrate is then optionally processed according to the methods described above to provide additional amino acids on the growing chain.

VI. Conclusion

The inventions herein provide a new approach for the simultaneous synthesis of a large number of compounds. The method can be applied whenever one has chemical building blocks that can be coupled in a solid-phase format, and when light can be used to generate a reactive group.

The above description is illustrative and not restrictive. Many variations of the invention will become apparent to those of skill in the art upon review of this disclosure. Merely by way of example, while the invention is illustrated primarily with regard to peptide, oligosaccharide and nucleotide synthesis, the invention is not so limited. By way of another example, while the detection apparatus has been illustrated primarily herein with regard to the detection of marked receptors, the invention will find application in other areas. For example, the detection apparatus disclosed herein could be used in the fields of catalysis, DNA or protein gel scanning, and the like. The scope of the invention should, therefore, be determined not with reference to the above description, but instead should be determined with reference to the appended claims along with their full scope of equivalents.

---

What is claimed is:

1. A method for synthesizing oligonucleotides on a solid phase comprising the steps of:
   a) providing a substrate as the solid phase, wherein said substrate comprises oligonucleotide molecules immobilized on a surface thereof, said oligonucleotide molecules coupled to a photoremovable protecting group;
   b) irradiating a first predefined region of said substrate without irradiating a second predefined region of said substrate to remove said protecting group from said oligonucleotide molecules in said first region; and
   c) contacting said substrate with a first nucleotide to couple said first nucleotide to said oligonucleotide molecules in said first predefined region, said first nucleotide having a nucleotide protecting group thereon, forming a first oligonucleotide on said substrate in said first predefined region that is different from an oligonucleotide in said second predefined region.

2. The method as recited in claim 1 wherein said step of irradiating is a step of masking a light source with a mask placed between said light source and said substrate, said mask comprising first transparent regions and second opaque regions, said transparent regions transmitting light from said source to at least said first predefined region, and said opaque regions blocking light from said source to at least said second predefined region.

3. The method as recited in claim 1 wherein said first and second regions each have total areas less than about 1 cm$^2$.

4. The method as recited in claim 1 wherein said steps of irradiating are conducted with a monochromatic light.

5. The method as recited in claim 1 wherein said steps of irradiating and contacting are repeated so as to synthesize 10$^3$ different oligonucleotides on said substrate.

6. The method as recited in claim 1 wherein the step of irradiating a first predefined region is a step of irradiating half of a region of said substrate irradiated in a prior synthesis step, and not irradiating half of said region irradiated in a prior synthesis step.

7. The method as recited in claim 1 wherein said steps a) and b) are repeated to synthesize more than 1,000 different oligonucleotides on different synthesis regions of said substrate, each of said different oligonucleotides occupying an area of less than about 10$^{-2}$ cm$^2$.

8. A method of synthesizing oligonucleotides comprising the sequential steps of:
   a) generating a pattern of light and dark areas by selectively irradiating at least a first area of a surface of a substrate, said surface comprising immobilized nucleotides on said surface, said nucleotides coupled to a photoremovable protective group, without irradiating at least a second area of said surface, to remove said protective group from said nucleotides in said first area;
   b) simultaneously contacting said first area and said second area of said surface with a first nucleotide to couple said first nucleotide to said immobilized nucleotides in said first area, and not in said second area, said first nucleotide having said photoremovable protective group;
   c) generating another pattern of light and dark areas by selectively irradiating with light at least a part of said first area of said surface and at least a part of said second area to remove said protective group in said at least a part of said first area and said at least a part of said second area;
   d) simultaneously contacting said first area and said second area of said surface with a second nucleotide to couple said second nucleotide to said immobilized nucleotides in at least a part of said first area and at least a part of said second area; and e) performing additional irradiating and nucleotide contacting and coupling steps so that a matrix array of at least 100 different oligonucleotides is formed on said surface, each different oligonucleotide synthesized in an area of less than 0.1 cm$^2$, whereby said different oligonucleotides have sequences and locations on said surface defined by the patterns of light and dark areas formed during the irradiating steps and the nucleotides coupled in said contacting steps.

9. The method as recited in claim 8 wherein said substrate is selected from the group consisting of Langmuir Blodgett film, glass, germanium, silicon, (poly)tetrafluorethylene, polystyrene, gallium arsenide, gallium phosphide, silicon oxide, silicon nitride, and combinations thereof.

10. The method as recited in claim 10 wherein said protective group is selected from the group consisting of 6-nitroveratryloxycarbonyl, 2-nitrobenzyloxy carbonyl, dimethyl dimethoxybenzyloxy carbonyl, 5-bromo-7-nitroindolinyl, o-hydroxyalpha-methyl cinnamoyl, 2-oxymethylene anthriquinone, and mixtures thereof.

11. The method as recited in claim 8 wherein each of said different oligonucleotides is contained within an area of between about 1 um$^2$ and 10,000 um$^2$.

12. The method as recited in claim 8 wherein the irradiating step c) further comprises steps of:

i) placing a mask adjacent to said substrate, said mask having substantially transparent regions and substantially opaque regions at a wavelength of light; and ii) illuminating said mask with a light source, said light source producing at least said wavelength of light, said mask permitting illumination of half of said substrate which was illuminated and half of said substrate which was not illuminated in said step a).

13. The method as recited in claim 8 wherein said additional steps are performed so as to synthesize 10$^3$ different oligonucleotides in 10$^3$ respective preselected regions on said substrate.

14. The method as recited in claim 8 wherein said additional steps are performed so as to synthesize 10$^6$ different oligonucleotides in 10$^6$ respective preselected regions on said substrate.

15. The method of claim 8 wherein said additional steps are performed so that at least 1,000 different oligonucleotides are synthesized on said surface, and each different oligonucleotide is contained within an area less than about $1 \times 10^{-3}$cm$^2$.

16. The method of claim 8 wherein said immobilized nucleotides are attached to said surface by a linker selected from the group consisting of aryl acetylene and ethylene glycol.

17. The method of claim 8 wherein said immobilized nucleotides are attached to said surface by polyethylene glycol.

* * * * *

UNITED STATES PATENT AND TRADEMARK OFFICE
CERTIFICATE OF CORRECTION

PATENT NO. : 5,424,186
DATED : June 13, 1995
INVENTOR(S) : Fodor et al.

It is certified that error appears in the above-identified patent and that said Letters Patent is hereby corrected as shown below:

In the cover page, related U.S. application data, please delete "49,246, Dec. 6, 1990" and replace with --492,462, March 7, 1990--.

Signed and Sealed this

Eighth Day of May, 2001

Attest:

NICHOLAS P. GODICI

*Attesting Officer*  *Acting Director of the United States Patent and Trademark Office*